United States Patent [19]

Payne et al.

[11] Patent Number: 4,542,244

[45] Date of Patent: Sep. 17, 1985

[54] OXABICYCLOALKANE HERBICIDES

[75] Inventors: George B. Payne; Samuel B. Soloway, both of Modesto; James E. Powell, Ripon, all of Calif.; Steven A. Roman, Fulshear, Tex.; Willy D. Kollmeyer, Modesto, Calif.

[73] Assignee: Shell Oil Company, Houston, Tex.

[21] Appl. No.: 624,552

[22] Filed: Jun. 25, 1984

Related U.S. Application Data

[60] Division of Ser. No. 416,572, Sep. 13, 1982, , which is a continuation-in-part of Ser. No. 331,094, Dec. 16, 1981, abandoned.

[51] Int. Cl.$^4$ ............................................. C07C 35/18
[52] U.S. Cl. ..................................... 568/825; 568/822
[58] Field of Search ............................... 568/822, 825

[56] References Cited

U.S. PATENT DOCUMENTS 3,609,197 9/1971 Leffingwell ......................... 568/825
4,120,877 10/1978 Coker et al. ......................... 260/348
4,256,740 3/1981 Mues et al. ......................... 548/236

FOREIGN PATENT DOCUMENTS 49-12423 11/1974 Japan .
1469921 4/1977 United Kingdom ................ 568/822

OTHER PUBLICATIONS

Garside et al., "J. Chem. Soc.", (1969), pp. 716–721.

*Primary Examiner*—Werren B. Lone

[57] ABSTRACT

Certain substituted 3-cyclohexene-1-ol are intermediates to herbicides and plant growth.

10 Claims, No Drawings

OXABICYCLOALKANE HERBICIDES

CROSS-REFERENCE TO RELATED APPLICATIONS

This is a division of application Ser. No. 416,572, filed Sept. 13, 1982, which is a continuation-in-part of Application Ser. No. 331,094, filed Dec. 16, 1981, now abandoned.

BACKGROUND OF THE INVENTION

Field of the Invention

The present invention relates to novel oxabicycloalkane derivatives, their use for controlling plant growth and as herbicides and to herbicidal and plant growth regulating compositions containing these novel derivatives.

Summary of the Invention

The present invention relates to novel oxabicycloalkanes of the formula

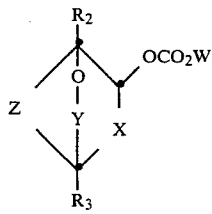

wherein
X is ($-CR_4R_4-$)$_m$ in which m is 0 or 1;
Y is ($-CR_5R_6-$)$_n$ in which n is 0, 1 or 2;
Z is ($-CR_7R_7-$)$_p$ in which p is 1, 2 or 3;
the sum of m+n+p is an integer of from 2 to 5, inclusive;
$R_1$ is a hydrogen atom or an alkyl group containing from 1 to 6 carbon atoms;
$R_2$ is a hydrogen atom or a straight-chain alkyl group containing from 1 to 6 carbon atoms; $R_3$ is a hydrogen atom or an alkyl group containing from 1 to 10 carbon atoms; a cyano group; an alkyl group substituted by: a hydroxy group, a cyano group, an alkoxy group containing from 1 to 6 carbon atoms, an aryloxy group, a $C_{1-6}$ alkylsulfonyl group, an arylsulfonyl group, an aralkylsulfonyl group, an azido group, a $C_{1-6}$-alkoxycarbonyl group, a hydroxycarbonyl group, a phosphoryl group, a phosphoryloxy group, an amine oxide, a carbamoyl, or thiocarbamoyl group in which each nitrogen is substituted by hydrogen or by 1 or 2 alkyl groups containing from 1 to 4 carbon atoms; or $R_3$ is an alkenyl or alkynyl group containing 2 to 4 carbon atoms; an aryl or aralkyl group, each containing from 6 to 11 carbon atoms including 1 to 4 carbon atoms in the alkyl portion and optionally ring substituted by one or more substituents selected from a halogen atom, each having an atomic number of from 9 to 35, inclusive, or by an alkyl or alkoxy group containing from 1 to 2 carbon atoms, each optionally substituted by one or more halogen atoms, each having an atomic number of 9 or 17; or $R_3$ is a group $-CSNH_2$, $-CO_2R_8$ or $-CON(R_8)_2$ in which $R_8$ is a hydrogen atom or an alkyl group containing from 1 to 6 carbon atoms; or $R_3$ is an acyl group containing 1 to 6 carbon atoms, an oxime or an acetal derivative of said acyl group;
each $R_4$ is independently a hydrogen atom, an alkyl group optionally substituted by up to 3 halogen atoms, a hydroxy group, or an alkoxy group containing 1 to 4 carbon atoms; or one of $R_4$ and $R_1$ together form a carbon-carbon bond;
$R_5$ and $R_6$ each independently is a hydrogen atom, or an alkyl group containing from 1 to 2 carbon atoms; or when located on a carbon atom adjacent to the ring oxygen atom then $R_5$ and $R_6$ together form an alkylene group containing 4 or 5 carbon atoms;
each $R_7$ independently is a hydrogen atom or an alkyl group containing from 1 to 4 carbon atoms optionally substituted by up to 3 halogen atoms; or when n is 0 then $R_7$ is also a chlorine atom, a bromine atom, or two of $R_7$ when located on adjacent carbon atoms together form an epoxide ring or a carbon-carbon bond; or when n is 1, then one $R_7$ on the carbon adjacent to the carbon bearing $R_2$ is a hydroxy group, a $C_{7-11}$ aralkoxy group, or an alkoxy group containing 1 or 4 carbon atoms, and the other $R_7$ is a hydrogen atom;
both of Q are hydrogen atoms or fluorine atoms;
W is an optionally-substituted unsaturated group of up to 4 carbon atoms or an aromatic or heterocyclic group containing up to 14 carbon atoms; a cycloalkyl group containing 3 to 10 carbon atoms optionally substituted by alkyl of 1 to 3 carbon atoms; or a secondary alkyl group containing 3 to 10 carbon atoms; and stereoisomer forms or mixtures thereof.

Optional substituents for W include hydroxy; cyano; halogen atoms having an atomic number of from 9 to 35, inclusive; or alkyl, haloalkyl, alkoxy, haloalkoxy, alkylthio, haloalkylthio, alkylsulfinyl, alkylsulfonyl, alkenyl or alkynyl of up to 4 carbon atoms; an aminocarboxyl, carboxyl, amino, or alkanoylamino, each of which hydrogen can be substituted for by alkyl of 1 to 4 carbon atoms; or equivalent kinds of substituents.

For example, W is an alkenyl or alkynyl group containing from 2 to 4 carbon atoms; a 4-pyrimidinyl group; a 2-pyrazinyl group; a 3-pyridazinyl group; a 2-pyridinyl group; a 2-furanyl group; a naphthyl group, or a phenyl group optionally substituted by: one or more of hydroxy; cyano, halogen; alkoxy, alkylthio or alkylsulfinyl of 1 to 3 carbon atoms, each optionally substituted by halogen; a benzyloxy group; an alkyl group containing 1 to 3 carbon atoms optionally substituted by halogen, hydroxy, amino, alkanoylamino, alkoxy or alkylthio; or amino, carboxyl or aminocarbonyl group or equivalent kinds of groups.

Preferably, W is an alkenyl or alkynyl group containing from 2 to 4 carbon atoms, a 4-pyrimidinyl group; a 2-pyrazinyl group; a 3-pyridazinyl group; a 2-pyridinyl group; a 2-furanyl group or a phenyl group optionally substituted by one or more of halogen, cyano, amino or an alkoxy or alkylthio group containing 1 to 3 carbon atoms, each optionally substituted by one or more halogen atoms having an atomic number of 9 or 17, or by an alkyl group containing 1 or 2 carbon atoms optionally substituted by one or more halogen atoms having an atomic number of 9 or 17, hydroxy, alkoxy of 1 or 2 carbon atoms or alkylthio of 1 or 2 carbon atoms, and stereoisomer forms of mixtures thereof.

Compounds that possess substantially the same plant growth regulator or herbicidal utility as those described above and can be prepared in like manner are equivalents thereof and include compounds wherein, for example, W is an optionally-substituted, unsaturated, cycloalkyl, secondary alkyl, aromatic or heterocyclic moiety or the like or equivalents thereof, including but not limited to cyano, cyclopropyl or 1-methylcyclopropyl, naphthyl, imidazolyl, triazolyl, thiadiazolyl, 2-quinolinyl, 1-isoquinolinyl, pyrrolyl, cyclohexenyl, N-methylimidazolyl, N-methylpyrazolyl, isoxazolyl, oxazolyl, isothiazolyl, thiazolyl, thienyl, 5-methyl-2-furanyl, and the like.

Non-limiting examples of species of the invention include
2-(benzyloxy)-1-methyl-4-isopropyl-7-oxabicyclo[2.2.1]heptane,
6-(benzyloxy)-1,3,3-trimethyl-2-oxabicyclo[2.2.2]octane,
6-(benzyloxy)-1,3,3-trimethyl-2-oxabicyclo[2.2.1]heptane,
7-(benzyloxy)-1,3,3-trimethyl-2-oxabicyclo[2.2.1]heptane,
2-(benzyloxy)-1-methyl-4-isopropyl-5-oxabicyclo[2.1.1]hexane,
6-(benzyloxy)-1-methyl-4-isopropyl-5-oxabicyclo[2.1.1]hexane,
5-(benzyloxy)-1,3,3-trimethyl-2-oxabicyclo[2.1.1]hexane,
7-(benzyloxy)-1-methyl-5-isopropyl-6-oxabicyclo[3.1.1]heptane,
2-(benzyloxy)-1,6,6-trimethyl-7-oxabicyclo[3.2.1]octane,
6-(benzyloxy)-1-isopropyl-5-methyl-8-oxabicyclo[3.2.1]octane,
8-(benzyloxy)-5,7,7-trimethyl-6-oxabicyclo[3.2.1]octane,
8-(benzyloxy)-1,3,3-trimethyl-2-oxabicyclo[3.2.1]octane,
7-(benzyloxy)-1,3,3-trimethyl-2-oxabicyclo[3.2.1]octane
6-(benzyloxy)-1,3,3-trimethyl-2-oxabicyclo[3.1.1]heptane,
8-(benzyloxy)-5,7,7-trimethyl-6-oxabicyclo[3.2.2.]nonane,
7-(benzyloxy)-1,3,3-trimethyl-2-oxabicyclo[3.2.2]nonane,
and the corresponding 2-methylbenzyl, 2-fluorobenzyl, 2-chlorobenzyl and 2-pyridinyl ether derivatives as well as the stereoisomer forms thereof.

The compounds of formula 1 exhibit geometrical and optical isomerism and may be prepared in geometrical and/or optically active forms, and as racemates. The various individual optical and geometrical forms and various combinations thereof of the materials of the invention usually have some differences in herbicidal properties. The present invention contemplates all the herbicidally active forms resulting from synthesis, and deliberately created mixtures.

Generally, in the compounds of formula 1, $R_1$ is preferably a hydrogen atom. $R_2$ is a hydrogen atom or straight-chain alkyl group containing from 1 to 3 carbon atoms, such as methyl, ethyl or n-propyl; A preferred subclass of the invention is when $R_2$ is a methyl group or an ethyl group. $R_3$ is preferably a hydrogen atom or an alkyl group containing from 1 to 3 carbon atoms, optionally substituted by halogen, for example, methyl, ethyl, n-propyl, isopropyl, or 1-chloro-1-methylethyl. When n is 0, then $R_3$ is preferably an isopropyl group. $R_4$ and $R_7$ are preferably each a hydrogen atom. $R_5$ and $R_6$ each is preferably a methyl group when on a ring carbon atom adjacent to the ring oxygen atom or otherwise each $R_5$ and $R_6$ is preferably a hydrogen atom. Both of Q are preferably hydrogen atoms.

W is preferably a 2-pyridinyl group or an optionally substituted phenyl group, for example, a 4-fluorophenyl, a 2-chlorophenyl, a 2-fluorophenyl, a 2-methylphenyl, a 2,6-dichlorophenyl, a phenyl group and the like. A preferred subclass of the invention is when W is 2-pyridinyl or a phenyl group substituted by one or two of a chlorine atom, a fluorine atom or a methyl group, preferably substituted in the 2- or 2,6-positions. Compounds wherein W is 2-methylphenyl are one preferred subclass, where W is 2-chlorophenyl, another preferred subclass, and where W is 2-fluorophenyl, another preferred subclass.

Compounds of formula 1 are preferably those where the sum of m+n+p is 3 or 4. Preferred subclasses of the invention are those where m is 1, n is preferably 0 or 1, and p is preferably 2.

One preferred subclass I of the invention wherein m is 1, n is 0 and p is 2 in formula 1 is directed to novel compounds of formula I

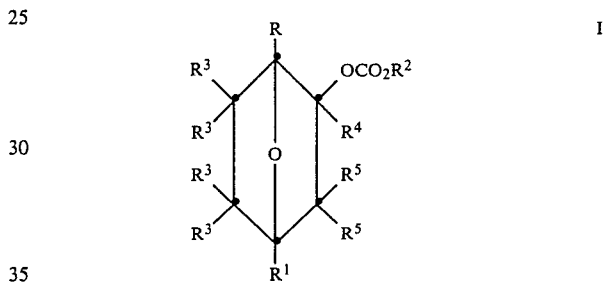

wherein
R is a hydrogen atom or a straight-chain alkyl group containing from 1 to 6 carbon atoms;
$R^1$ is a hydrogen atom; a cyano group; an alkyl group containing from 1 to 10 carbon atoms optionally substituted by up to 3 halogen atoms, each having an atomic number of from 9 to 35, inclusive, or by a hydroxy group, a cyano group, an alkoxy group containing from 1 to 6 carbon atoms, a $C_{1-6}$ alkylsulfonyl group, a $C_{6-10}$ arylsulfonyl group, a $C_{7-11}$ aralkylsulfonyl group, an azido group, a $C_{1-6}$ alkoxycarbonyl group, an hydroxycarbonyl group, a phosphoryl group, a phosphoryloxy group, an amine oxide group, a carbamoyl group, a thiocarbamoyl group in which each nitrogen is substituted by hydrogen or by 1 or 2 alkyl groups containing from 1 to 4 carbon atoms; or $R^1$ is an alkenyl or alkynyl group containing from 2 to 4 carbon atoms; or is an aryl or aralkyl group, each containing from 6 to 11 carbon atoms, and 1 to 4 carbons in the alkyl portion, each optionally ring-substituted by one or more substituents independently selected from a halogen atom, each having an atomic number of from 9 to 35, inclusive, or by an alkyl, or alkoxy group containing from 1 to 2 carbon atoms, each optionally substituted by one or more halogen atoms, each having an atomic number of from 9 or 17; or $R^1$ is a group $-CSNH_2$, $-CO_2R^6$ or $-CON(R^6)_2$ in which $R^6$ is a hydrogen atom, or an alkyl group containing from 1 to 6 carbon atoms;
$R^2$ is an alkenyl or alkynyl group containing from 2 to 4 carbon atoms; a 4-pyrimidinyl group; a 2-pyrazinyl group; a 3-pyridazinyl group; a 2-pyridinyl group; a 2-furanyl group; a naphthyl group; or a phenyl group optionally substituted by one or more substituents independently selected from a halogen atom, each having an atomic number of from 9 to 35, inclusive, cyano, or an alkoxy, alkylthio or alkylsulfinyl group containing from 1 to 3 carbon atoms, each optionally substituted by one or more halogen atoms, each having an atomic number of from 9 or 17, or by an alkyl group containing 1 or 2 carbon atoms optionally substituted by one or more halogen atoms having an atomic number of 9 or 17, hydroxy, mono- or dialkylamino- or alkanoylamino containing 1 or 2 carbon atoms in each alkyl group, alkoxy of 1 or 2 carbon atoms or alkylthio of 1 or 2 carbon atoms, or is a phenyl group substituted by mono- or dialkylamino- or alkanoylamino containing 1 or 2 carbon atoms in each alkyl group or a carboxyl group;

each $R^3$ is independently selected from a hydrogen atom; a chlorine atom; a bromine atom; or an alkyl group containing from 1 to 4 carbon atoms optionally substituted by up to 3 halogen atoms, each having an atomic number of from 9 to 35, inclusive; or two of $R^3$ when located on adjacent carbon atoms together form an epoxide ring or carbon-carbon bond;

$R^4$ is a hydrogen atom; or an alkyl group containing from 1 to 4 carbon atoms optionally substituted by up to 3 halogen atoms having an atomic number of from 9 to 35, inclusive;

each $R^5$ is independently selected from a hydrogen atom; or an alkyl group containing from 1 to 4 carbon atoms; each optionally substituted by up to 3 halogen atoms having an atomic number of from 9 to 35, inclusive, a hydroxy group, or an alkoxy group containing 1 to 4 carbon atoms; or $R^4$ and $R^5$ when taken together form a carbon-carbon bond;

both of Q are hydrogen atoms or fluorine atoms; and stereoisomeric forms or mixtures thereof.

Non-limiting examples of this subclass I of compounds of the invention include:

2-exo-(2,6-difluorobenzyloxy)-1,4-dipropyl-7-oxabicyclo[2.2.1]heptane,
2-endo-(benzyloxy)-1,4-dibutyl-7-oxabicyclo[2.2.1]heptane,
2-exo-(2-(trifluoromethyl)benzyloxy)-1,4-diethyl-7-oxabicyclo[2.2.1]heptane,
2-exo-(4-fluorobenzyloxy)-1-methyl-4-(1-cyano-1-methylethyl)-7-oxabicyclo[2.2.1]heptane,
2-endo-(2-methylbenzyloxy)-4-hexyl-7-oxabicyclo[2.2.1]heptane,
2-exo-(2,6-dimethylbenzyloxy)-1-methyl-4-(1-methoxy-1-methylethyl)-7-oxabicyclo[2.2.1]heptane,
2-exo-(2,4-dichlorobenzyloxy)-1-methyl-4-hexyl-7-oxabicyclo[2.2.1]heptane,
2-endo-(2-pyridinylmethoxy)-1-ethyl-4-isobutyl-7-oxabicyclo[2.2.1]heptane,
2-exo-(2-furanylmethoxy)-1-ethyl-4-isopropyl-7-oxabicyclo[2.2.1]heptane,
2-exo-(2-methoxybenzyloxy)-1-methyl-4-isopropyl-7-oxabicyclo[2.2.1]heptane,
2-exo-(benzyloxy)-5,6-dichloro-1,4,5,6-tetramethyl-7-oxabicyclo(2.2.1)heptane,
2-exo-(benzyloxy)-5,6-dibromo-1,4-diethyl-7-oxabicyclo[2.2.1]heptane,
2-exo-(benzyloxy)-1-methyl-4-(1-methyl-1-phenoxyethyl)-7-oxabicyclo[2.2.1]heptane,
2-endo-(benzyloxy)-1-methyl-4-benzyl-7-oxabicyclo[2.2.1]heptane,
2-exo-(2-fluorobenzyloxy)-1-methyl-4-(1-methylethenyl)-7-oxabicyclo[2.2.1]heptane,
2-exo-(2-difluoromethoxy)benzyloxy)-1-methyl-4-(1-methyl-1-(dimethylamino)ethyl)-7-oxabicyclo[2.2.1]heptane N-oxide,
2-exo-(2-propynyloxy)-1-methyl-4-isopropyl-7-oxabicyclo[2.2.1]heptane,
2-exo-(allyloxy)-1,4-dimethyl-5,6-epoxy-7-oxabicyclo[2.2.1]heptane,
2-exo-(2-fluorobenzyloxy)-1,4-dimethyl-5,6-epoxy-7-oxabicyclo[2.2.1]heptane,
2-exo-(3-fluorobenzyloxy)-1,2-dimethyl-4-isopropyl-7-oxabicyclo[2.2.1]heptane,
2-exo-(2-fluorobenzyloxy)-1,2-dimethyl-4-isopropyl-7-oxabicyclo[2.2.1]heptane,
2-endo-(2-methylthio)benzyloxy-1,3,3,4-tetramethyl-7-oxabicyclo[2.2.1]heptane,
2-exo-(2-fluorobenzyloxy)-1,3,3,4-tetramethyl-7-oxabicyclo[2.2.1]heptane,
2-exo-(3,5-difluorobenzyloxy)-1,3,3-trimethyl-4-isopropyl-7-oxabicyclo[2.2.1]heptane,
2-exo-(2-fluorobenzyloxy)-1,3,3-trimethyl-4-isopropyl-7-oxabicyclo[2.2.1]heptane,
2-exo-(2-chlorobenzyloxy)-1,3,3-trimethyl-7-oxabicyclo[2.2.1]heptane,
2-exo-(2-fluorobenzyloxy)-1,3,3-trimethyl-7-oxabicyclo[2.2.1]heptane,
2-exo-(2-pyridinylmethoxy)-1-methyl-4-(1-methylethenyl)-7-oxabicyclo[2.2.1]heptane,
2-exo-(2-fluorobenzyloxy)-1-methyl-4-(1-methylethenyl)-7-oxabicyclo[2.2.1]heptane,
2-exo-(2-furanylmethoxy)-1-methyl-4-(2-butynyl)-7-oxabicyclo[2.2.1]heptane,
2-exo-(2-fluorobenzyloxy)-1-methyl-4-(2-butynyl)-7-oxabicyclo[2.2.1]heptane,
2-exo-(2,6-dichlorobenzyloxy)-1-methyl-4-(methoxycarbonyl)-7-oxabicyclo[2.2.1]heptane,
2-exo-(2-fluorobenzyloxy)-1-methyl-4-(methoxycarbonyl)-7-oxabicyclo[2.2.1]heptane,
2-exo-(4-(difluoromethoxy)benzyloxy)-1-methyl-4-cyano-7-oxabicyclo[2.2.1]heptane,
2-exo-(2-fluorobenzyloxy)-1-methyl-4-cyano-7-oxabicyclo[2.2.1]heptane,
2-endo-(benzyloxy)-1,4-dimethyl-5-cyano-7-oxabicyclo[2.2.1]heptane,
2-exo-(2-fluorobenzyloxy)-1,4-dimethyl-5-cyano-7-oxabicyclo[2.2.1]heptane,
2-exo-(2-methyl-2-propenyloxy)-1,4-dimethyl-6-cyano-7-oxabicyclo[2.2.1]heptane,
2-exo-(2-fluorobenzyloxy)-1,4-dimethyl-6-cyano-7-oxabicyclo[2.2.1]heptane,
2-exo-(4-fluorobenzyloxy)-1,4-dimethyl-5-(ethoxycarbonyl)-7-oxabicyclo[2.1.1]heptane,
2-exo-(2-fluorobenzyloxy)-1,4-dimethyl-5-(ethoxycarbonyl)-7-oxabicyclo[2.2.1]heptane,
2-endo-(2-methylbenzyloxy)-1,4-dimethyl-6-(ethoxycarbonyl)-7-oxabicyclo[2.2.1]heptane,
2-exo-(2-fluorobenzyloxy)-1,4-dimethyl-6-(ethoxycarbonyl)-7-oxabicyclo[2.2.1]heptane,
2-exo-(5-methylfuranylmethoxy)-1-methyl-4-isopropyl-7-oxabicyclo[2.2.1]heptane,
2-exo-(2-butynyloxy)-1,4-dimethyl-7-oxabicyclo[2.2.1]heptane, 2-endo-(4-methylbenzyloxy)-1,4-dimethyl-3-methoxy-7-oxabicyclo[2.2.1]heptane,
2-exo-(2-fluorobenzyloxy)-1,4-dimethyl-3-methoxy-7-oxabicyclo[2.2.1]heptane,
2-exo-(2-methylbenzyloxy)-4-(1-carboxy-1-methylethyl)-1-methyl-7-oxabicyclo[2.2.1]heptane,
2-exo-(2-fluorobenzyloxy)-4-(1-carboxy-1-methylethyl)-1-methyl-7-oxabicyclo[2.2.1]heptane,
2-exo-(3-trifluoromethyl)benzyloxy)-b 4-(1-methoxycarbonyl-1-methylethyl)-1-methyl-7-oxabicyclo[2.2.1]heptane,
2-exo-(2-fluorobenzyloxy)-4-(1-methoxycarbonyl-1-methylethyl)-1-methyl-7-oxabicyclo[2.2.1]heptane,
2-exo-(benzyloxy)-4-(1-carbamoyl-1-methylethyl)-1-methyl-7-oxabicyclo[2.2.1]heptane,
2-exo-(2-fluorobenzyloxy)-4-(1-(N,N-dimethylcarbamoyl)-1-methylethyl)-1-methyl-7-oxabicyclo[2.2.1]heptane,
2-exo-(2-fluorobenzyloxy)-4-(1-azido-1-methylethyl)-1-methyl-7-oxabicyclo[2.2.1]heptane,
2-exo-(benzyloxy)-4-(1-bromo-1-methylethyl)-1-methyl-7-oxabicyclo[2.2.1]heptane,
2-exo-(benzyloxy)-1,2,4-trimethyl-7-oxabicyclo[2.2.1]heptane,
2-exo-(benzyloxy)-1,3,3,4-tetramethyl-7-oxabicyclo[2.2.1]heptane,
2-exo-(benzyloxy)-1,4,5,6-tetramethyl-7-oxabicyclo[2.2.1]heptane,
2-exo-(benzyloxy)-1,4,5,6-tetramethyl-5,6-epoxy-7-oxabicyclo[2.2.2]heptane,
2-exo-(benzyloxy)-1,4,5,6-tetramethyl-7-oxabicyclo[2.2.1]hept-5-ene,
2-exo-(benzyloxy)-3-chloro-1-methyl-4-isopropyl-7-oxabicyclo[2.2.1]heptane,
2-exo-(benzyloxy)-1-methyl-4-isopropyl-7-oxabicyclo[2.2.1]hept-2-ene,
2-exo-(4-pyrimidinylmethoxy)-1-methyl-4-isopropyl-7-oxabicyclo[2.2.1]heptane,
2-exo-(2-pyrazinylmethoxy)-1-methyl-4-isopropyl-7-oxabicyclo[2.2.1]heptane,
2-exo-(benzyloxy)-1-methyl-4-cyano-7-oxabicyclo[2.2.1]heptane,
2-exo-(benzyloxy)-1-methyl-4-carbamoyl-7-oxabicyclo[2.2.1]heptane,
2-exo-(benzyloxy)-1-methyl-4-(hydroxycarbonyl)-7-oxabicyclo[2.2.1]heptane,
2-exo-(2,4-dichlorobenzyloxy)-1-methyl-4-isopropyl-7-oxabicyclo[2.2.1]heptane,
2-exo-(2,5-dichlorobenzyloxy)-1-methyl-4-isopropyl-7-oxabicyclo[2.2.1]heptane,
2-exo-(2-(difluoromethoxy)benzyloxy)-1-methyl-4-isopropyl-7-oxabicyclo[2.2.1]heptane,
2-exo-(2,5-dichloro-3-aminobenzyloxy)-1-methyl-4-isopropyl-7-oxabicyclo[2.2.1]heptane,
2-exo-(2,5-dichloro-6-methoxybenzyloxy)-1-methyl-4-isopropyl-7-oxabicyclo[2.2.1]heptane,
2-exo-(2,4-dichlorobenzyloxy)-1-methyl-4-isopropyl-7-oxabicyclo[2.2.1]heptane,
2-exo-(2,5-dichlorobenzyloxy)-1-methyl-4-isopropyl-7-oxabicyclo[2.2.1]heptane,
2-exo-(2,6-dimethylbenzyloxy)-1-methyl-4-isopropyl-7-oxabicyclo[2.2.1]heptane,
2-exo-(2-trifluoromethyl)benzyloxy-1-methyl-4-isopropyl-7-oxabicyclo[2.2.1]heptane,
2-exo-(4-fluorobenzyloxy)-1-methyl-4-isopropyl-7-oxabicyclo[2.2.1]heptane,
2-exo-(2-chloro-6-fluorobenzyloxy)-1-methyl-4-isopropyl-7-oxabicyclo[2.2.1]heptane,
2-exo-(2-methyl-6-fluorobenzyloxy)-1-methyl-4-isopropyl-7-oxabicyclo[2.2.1]heptane,
2-exo-(3-pyridazinylmethoxy)-1-methoxy-4-isopropyl-7-oxabicyclo[2.2.1]heptane,
2-exo-(2-cyanobenzyloxy)-1-methyl-4-isopropyl-7-oxabicyclo[2.2.1]heptane,
2-exo-(cyanomethoxy)-1-methyl-4-isopropyl-7-oxabicyclo[2.2.1]heptane,
2-exo-(α,α-difluorobenzyloxy)-1-methyl-4-isopropyl-7-oxabicyclo[2.2.1]heptane,
2-exo-(3-chlorobenzyloxy)-1-methyl-4-isopropyl-7-oxabicyclo[2.2.1]heptane,
2-exo-(4-chlorobenzyloxy)-1-meethyl-4-isopropyl-7-oxabicyclo[2.2.1]heptane,
2-exo-(3,4-dichlorobenzyloxy)-1-methyl-4-isopropyl-7-oxabicyclo[2.2.1]heptane,
2-exo-(1-naphthylmethoxy)-1-methyl-4-isopropyl-7-oxabicyclo[2.2.1]heptane,
2-exo-(2-methylbenzyloxy)-1-methyl-4-isopropyl-7-oxabicyclo[2.2.1]heptane,
2-exo-(4-methylbenzyloxy)-1-methyl-4-isopropyl-7-oxabicyclo[2.2.1]heptane,
2-exo-(2-(methoxy)benzyloxy)-1-methyl-4-isopropyl-7-oxabicyclo[2.2.1]heptane,
2-exo-(3,5-dichlorobenzyloxy)-1-methyl-4-isopropyl-7-oxabicyclo[2.2.1]heptane,
2-exo-(4-(trifluoromethyl)benzyloxy)-1-methyl-4-isopropyl-7-oxabicyclo[2.2.1]heptane,
2-exo-(3-(methoxy)benzyloxy)-1-methyl-4-isopropyl-7-oxabicyclo[2.2.1]heptane,
2-exo-(4-(methoxy)benzyloxy)-1-methyl-4-isopropyl-7-oxabicyclo[2.2.1]heptane,
2-exo-(2-bromobenzyloxy)-1-methyl-4-isopropyl-7-oxabicyclo[2.2.1]heptane,
2-exo-(3-(trifluoromethoxy)benzyloxy)-1-methyl-4-isopropyl-7-oxabicyclo[2.2.1]heptane,
2-exo-(4-(trifluoromethoxy)benzyloxy)-1-methyl-4-isopropyl-7-oxabicyclo[2.2.1]heptane,
2-exo-(benzyloxy)-4-(1-fluoro-1-methylethyl)-1-methyl-7-oxabicyclo[2.2.1]heptane,
2-exo-(3-fluorobenzyloxy)-4-(ethoxycarbonyl)-1-methyl-7-oxabicyclo[2.2.1]heptane,
2-exo-(2-fluorobenzyloxy)-4-cyano-1-methyl-7-oxabicyclo[2.2.1]heptane,
2-exo-(2-cyanobenzyloxy)-1-methyl-4-4-isopropyl-7-oxabicyclo[2.2.1]heptane,
2-exo-(2-methyl-6-fluorobenzyloxy)-1-methyl-4-isopropyl-7-oxabicyclo[2.2.1]heptane,
2-exo-(2-methyl-4-fluorobenzyloxy)-1-methyl-4-isopropyl-7-oxabicyclo[2.2.1]heptane,
2-exo-(2-(hydroxymethyl)benzyloxy)-1-methyl-4-isopropyl-7-oxabicyclo[2.2.1]heptane,
2-exo-(2-(methoxymethyl)benzyloxy)-1-methyl-4-isopropyl-7-oxabicyclo[2.2.1]heptane,
2-exo-(4-cyanobenzyloxy)-1-methyl-4-isopropyl-7-oxabicyclo[2.2.1]heptane,
2-exo-(4-ethynylbenzyloxy)-1-methyl-4-isopropyl-7-oxabicyclo[2.2.1heptane,
2-exo-(2-ethynylbenzyloxy)-1-methyl-4-isopropyl-7-oxabicyclo[2.2.1]heptane,
2-exo-(2-iodobenzyloxy)-1,4-diethyl-7-oxabicyclo[2.2.1]heptane,
2-exo-(2-aminobenzyloxy)-1-methyl-4-isopropyl-7-oxabicyclo[2.2.1]heptane.
2-exo-(benzyloxy)-1-methyl-4-thiocarbamoyl-7-oxabicyclo[2.2.1]heptane.

Preferably, in the compounds of formula I, each Q is a hydrogen atom. R is a hydrogen atom or a straight-chain alkyl group containing from 1 to 3 carbon atoms. $R^1$ is a hydrogen atom or an alkyl group containing 1 to 3 carbon atoms optionally substituted by halogen, for example, a methyl, ethyl, n-propyl, isopropyl or 1-chloro-1-methylethyl group and the like. A further preferred subclass of the invention is when R is an alkyl group containing from 1 to 2 carbon atoms, i.e. a methyl or ethyl group and $R^1$ is an alkyl group containing from 1 to 3 carbon atoms, e.g. a methyl, ethyl, n-propyl or isopropyl group. Compounds wherein R is a methyl group and $R^1$ is an isopropyl group are one preferred subclass, compounds wherein R and $R^1$ each is an ethyl group are another preferred subclass, and compounds wherein R is a methyl group and $R^1$ is a 1-chloro-1-methylethyl group is a third preferred subclass;

$R^2$ in formula I is preferably an ethynyl group, a 2-pyridinyl group, or a phenyl group optionally substituted by 1 or 2 substituents, for example, 4-fluorophenyl, 2-chlorophenyl, 2-fluorophenyl, 2-methylphenyl, 2,6-dichlorophenyl, phenyl, and the like. A preferred subclass of the invention is when $R^2$ is 2-pyridinyl or a phenyl group substituted by one or two of a chlorine atom, a fluoride atom or a methyl group, preferably substituted in the 2-, or 2,6-positions. Compounds wherein $R^2$ is 2-methylphenyl are one preferred subclass, where $R^2$ is 2-chlorophenyl another preferred subclass, and where $R^2$ is 2-fluorophenyl, another preferred subclass.

Each $R^3$ is preferably independently a hydrogen atom; a chlorine atom; a bromine atom; or an alkyl group containing 1 to 2 carbon atoms, i.e., a methyl or ethyl group. A further preferred subclass of the invention is when each $R^3$ is a hydrogen atom;

Preferably, $R^4$ is a hydrogen atom; and

Preferably, each $R^5$ is a hydrogen atom or an alkyl group containing 1 to 2 carbon atoms, i.e., a methyl or ethyl group. A further preferred subclass is when each $R^5$ is a hydrogen atom.

Because of their properties, one especially preferred further subclass of Compounds of the Invention are compounds of the formula Ia

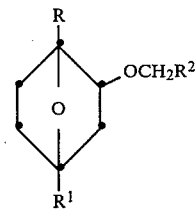

Ia wherein R is a hydrogen atom or a straight-chain alkyl group containing from 1 to 6 carbon atoms; $R^1$ is hydrogen or an alkyl group containing from 1 to 6 carbon atoms optionally substituted by up to 3 halogen atoms selected independently from fluorine, chlorine and bromine atoms or by OH, CN, an alkoxy group containing from 1 to 6 carbon atoms, a $C_{1-6}$ alkylsulfonyl group, a phenylsulfonyl group, a benzylsulfonyl group; or $R^1$ is an alkenyl or alkynyl group containing from 2 to 4 carbon atoms, or is an aryl or aralkyl group, each containing from 6 to 11 carbon atoms, and 1 or 2 carbon atoms in any alkyl portion, optionally ring-substituted by one or more substituents independently selected from a halogen atom having an atomic number of from 9 to 35, inclusive, or by an alkyl or alkoxy group containing from 1 to 2 carbon atoms, each optionally substituted by one or more halogen atoms having an atomic number of 9 or 17; and $R^2$ is an alkenyl or alkynyl group containing from 2 to 4 carbon atoms, a 2-pyridinyl group, a 2-furanyl group or a phenyl group optionally substituted by one or more substituents independently selected from a halogen atom having an atomic number of from 9 to 35, inclusive, or an alkoxy or alkylthio group containing from 1 to 2 carbon atoms, each optionally substituted by one or more halogen atoms having an atomic number of 9 or 17, or by an alkyl group containing 1 or 2 carbon atoms optionally substituted by one or more halogen atoms having an atomic number of 9 or 17, hydroxy, alkoxy of 1 or 2 carbon atoms or alkylthio of 1 or 2 carbon atoms; and stereoisomeric forms or mixtures thereof.

Preferably, in the compounds of formula Ia, R is a straight-chain alkyl group containing from 1 to 3 carbon atoms, and $R^1$ is an alkyl group containing from 1 to 3 carbon atoms optionally substituted by halogen, for example, a methyl, ethyl, isopropyl or n-propyl group and the like. A further preferred subclass of the invention is when R is an alkyl group containing from 1 to 2 carbon atoms, i.e., a methyl or ethyl group and $R^1$ is an alkyl group containing from 1 to 3 carbon atoms optionally substituted by chlorine, e.g. a methyl, ethyl, n-propyl, isopropyl or 1-chloro-1-methylethyl group. Compounds wherein R is a methyl group and $R^1$ is an isopropyl group are one preferred subclass, compounds wherein R and $R^1$ each is an ethyl group are another preferred subclass, and compounds wherein R is methyl and $R^1$ is a 1-chloro-1-methylethyl group is a third preferred subclass;

$R^2$ in formula Ia is preferably an ethynyl group, a 2-pyridinyl group or an optionally substituted phenyl group, for example, a 4-fluorophenyl, a 2-chlorophenyl, a 2-fluorophenyl, a 2-methylphenyl, a 2,6-dichlorophenyl, a phenyl group and the like. A preferred subclass of the invention is when $R^2$ is 2-pyridinyl or phenyl group substituted by one or two of a chlorine atom, a fluorine atom or a methyl group, preferably substituted in the 2- or 2,6-positions. Compounds wherein $R^2$ is 2-methylphenyl are one preferred subclass, where $R^2$ is 2-chlorophenyl another preferred subclass, and where $R^2$ is 2-fluorophenyl another preferred subclass.

The materials of formula I that have the $R^2CH_2O$ group exo (formula Ib below) with respect to the oxygen-containing bridge are usually more herbicidally active than the endo form (formula Ic below) or the exo-endo mixture and are preferred.

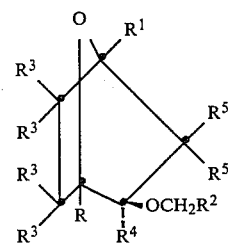

Formula Ib

1S—exo-form

Formula Ic

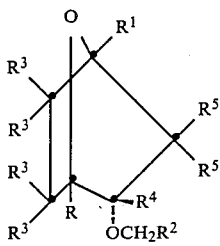

1S—endo-form

When $R^3$ is hydrogen, then the compounds of formula Ib and Ic have the 1S absolute configuration shown above. Such compounds of the subclass of formula Ib of the invention that correspond in configuration are preferred.

When an isomer or a mixture of isomers other than racemic mixtures is used substantially free of all other possible isomers, they are usually at least about 70% pure, although a purity above about 80% is preferable and a purity above about 95% is highly desirable. This invention contemplates all of the herbicidally active isomers, as well as any mixtures of isomers resulting from the synthesis methods used, and deliberately created mixtures.

While the ether compounds of this subclass I of the invention are ultimately made from simple, available, known starting materials, the immediate precursor 2-hydroxy-7-oxabicyclo[2.2.1]heptanes are, as a general class, novel compounds as are many of their precursor ketones, epoxides and 3-cyclohexen-1-ols. Thus, the present invention is also directed to (1) novel compounds of the formula Id, Ie, and If Id

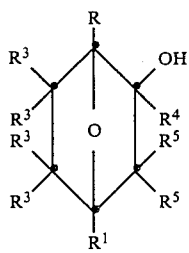

Ie

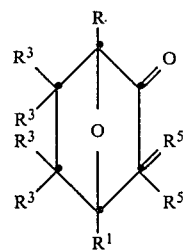

If

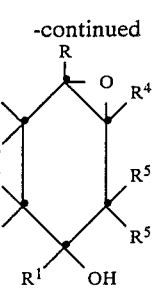

wherein

R is a hydrogen atom; or a straight-chain alkyl group containing from 1 to 6 carbon atoms;

$R^1$ is a hydrogen atom; or is an alkyl group containing from 1 to 10 carbon atoms optionally substituted by up to 3 halogen atoms, each having an atomic number of from 9 to 35, inclusive, or by a hydroxy group, a cyano group, an alkoxy group containing from 1 to 4 carbon atoms, a $C_{1-6}$ alkylsulfonyl group, a arylsulfonyl group, an aralkylsulfonyl group, an azido group, a $C_{1-6}$ alkoxycarbonyl group, a hydroxycarbonyl group, a phosphoryl group, a phosphoryloxy group, an amine oxide group, a carbamoyl group or a thiocarbamoyl group in which each nitrogen atom is substituted by hydrogen or 1 or 2 alkyl groups containing from 1 to 4 carbon atoms; or $R^1$ is an alkenyl or alkynyl group containing from 2 to 4 carbon atoms; or is an aryl or aralkyl group, each containing from 6 to 11 carbon atoms, and 1 to 4 carbons in the alkyl portion, each optionally ring-substituted by one or more substituents independently selected from a halogen atom, each having an atomic number of from 9 to 35, inclusive, or by an alkyl or alkoxy group containing from 1 to 2 carbon atoms, each optionally substituted by one or more halogen atoms, each having an atomic number of 9 or 17, inclusive, or $R^1$ is a group $-CO_2R^6$ or $-CON(R^6)_2$ in which $R^6$ is a hydrogen atom, or an alkyl group containing from 1 to 6 carbon atoms; or in formula Ic, then $R^1$ is additionally a cyano group;

each $R^3$ is independently selected from a hydrogen atom, a chlorine atom, a bromine atom, or an alkyl group containing from 1 to 4 carbon atoms or an alkoxy group containing from 1 to 4 carbon atoms, each optionally substituted by up to 3 halogen atoms, each having an atomic number of 9 or 17, or two of $R^3$ when located on adjacent carbon atoms together form an epoxide ring;

$R^4$ is a hydrogen atom or an alkyl group containing from 1 to 4 carbon atoms optionally substituted by up to 3 halogen atoms having an atomic number of from 9 to 35, inclusive;

each $R^5$ is independently selected from a hydrogen atom or an alkyl group containing from 1 to 4 carbon atoms optionally substituted by up to 3 halogen atoms having an atomic number of from 9 to 35, inclusive; or a hydroxy group;

with the proviso that R and $R^1$ are not both hydrogen and in formulas Id and If, when R is methyl and $R^3$, $R^4$, and $R^5$ all are hydrogen atoms, then $R^1$ is other than isopropyl;

and stereoisomeric forms or mixtures thereof;

and (2) novel compounds of the formula Ig

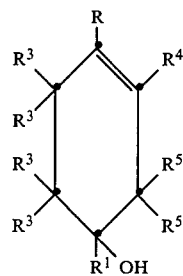

wherein

R is a hydrogen atom; or a straight-chain alkyl group containing from 1 to 6 carbon atoms;

$R^1$ is a hydrogen atom; or is an alkyl group containing from 1 to 10 carbon atoms optionally substituted by up to 3 halogen atoms, each having an atomic number of from 9 to 35, inclusive, or by a hydroxy group, a cyano group or an alkoxy group containing from 1 to 4 carbon atoms, a $C_{1-6}$ alkylthio group, a $C_{6-10}$ arylthio group, a $C_{7-11}$ aralkylthio group, an azido group, a $C_{1-6}$ alkoxycarbonyl group, a hydroxycarbonyl group, a phosphoryl group, a phosphoryloxy group, a carbamoyl group or a thiocarbamoyl group in which each nitrogen atom is substituted by hydrogen or 1 or 2 alkyl groups containing from 1 to 4 carbon atoms; or is an aryl or aralkyl group, each containing from 6 to 11 carbon atoms, and 1 to 4 carbons in the alkyl portion, each optionally ring-substituted by one or more substituents independently selected from a halogen atom, each having an atomic number of from 9 to 35, inclusive, or by an alkyl or alkoxy group containing from 1 to 2 carbon atoms each optionally substituted by one or more halogen atoms, each having an atomic number of 9 or 17, or $R^1$ is a group —$CO_2R^6$ or —$CON(R^6)_2$ in which $R^6$ is a hydrogen atom, or an alkyl group containing from 1 to 6 carbon atoms;

each $R^3$ is independently selected from a hydrogen atom; a chlorine atom; a bromine atom; or an alkyl group containing from 1 to 4 carbon atoms, optionally substituted by up to 3 halogen atoms, each having an atomic number of from 9 to 35, inclusive; or two of $R^3$ when located on adjacent carbon atoms together form an epoxide ring;

$R^4$ is a hydrogen atom; or an alkyl group containing from 1 to 4 carbon atoms optionally substituted by up to 3 halogen atoms having an atomic number of from 9 to 35, inclusive;

each $R^5$ is independently selected from a hydrogen atom; or an alkyl group containing from 1 to 4 carbon atoms optionally substituted by up to 3 halogen atoms having an atomic number of from 9 to 35, inclusive; or a hydroxy group;

with the proviso that R and $R^1$ are not both H and when R is methyl and $R^3$, $R^4$ and $R^5$ all are hydrogen atoms, then $R^1$ is other than isopropyl, and stereoisomeric forms or mixtures thereof.

Non-limiting examples of the materials of formulas Id, Ie, If and Ig are set forth below as Ih, Ii, Ij and Ik:

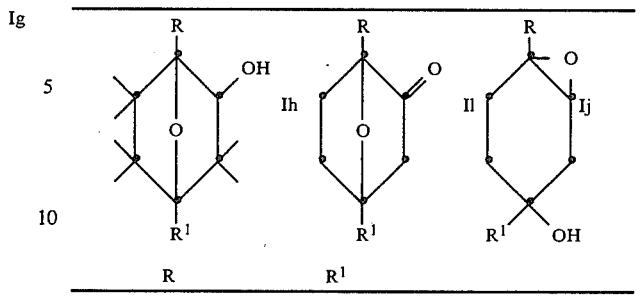

| R | $R^1$ |
|---|---|
| H | $C_2H_5$ |
| $CH_3$ | $C_6H_5$ |
| $CH_3$ | $C_2H_5$ |
| $CH_3$ | $n-C_4H_9$ |
| $C_2H_5$ | $CH_3$ |
| $C_2H_5$ | $C_2H_5$ |
| $n-C_3H_7$ | $CH_3$ |
| $CH_3$ | $CH_3$ |
| $CH_3$ | —$C(CH_3)_2Cl$ |
| $CH_3$ | —$C(CH_3)_2OCH_3$ |
| $CH_3$ | —$C(CH_3)_2OC_2H_5$ |
| $CH_3$ | —$C(CH_3)_2O$—$i-C_3H_7$ |
| $CH_3$ | —$C(CH_3)_2OH$ |
| $CH_3$ | —$C(CH_3)_2CN$ |
| $CH_3$ | —$C(CH_3)_2SO_2C_6H_5$ |
| $CH_3$ | —$C(CH_3)_2SO_2CH_3$ |
| $CH_3$ | H |
| $i-C_3H_7$ | $CH_3$ |
| $C_6H_5$ | $CH_3$ |
| $CH_3$ | $CH_2C(O)OC_2H_5$ |
| $CH_3$ | $C(CH_3)=CH_2$ |

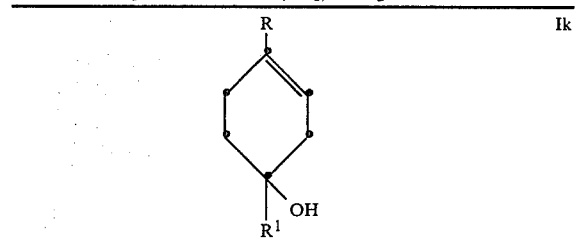

| R | $R^1$ |
|---|---|
| H | $C_2H_5$ |
| $CH_3$ | $CH_3$ |
| $C_2H_5$ | $CH_3$ |
| $C_2H_5$ | $C_2H_5$ |
| $CH_3$ | $C_2H_5$ |
| $CH_3$ | $n-C_4H_9$ |
| $n-C_3H_7$ | $CH_3$ |
| $CH_3$ | $C_6H_5$ |
| $CH_3$ | —$C(CH_3)_2OCH_2$ |
| $CH_3$ | —$C(CH_3)_2OC_2H_5$ |
| $CH_3$ | —$C(CH_3)_2O$—$iC_3H_7$ |
| $CH_3$ | —$C(CH_3)_2SC_6H_5$ |
| $CH_3$ | —$C(CH_3)_2CN$ |
| $CH_3$ | —$C(CH_3)_2OH$ |
| $CH_3$ | —$C(CH_3)_2Cl$ |
| $CH_3$ | —$C(CH_3)_2SCH_3$ |
| $CH_3$ | H |

Subject to any proviso stated above in the general description of Id through Ik, preferably, in the novel compounds of Formulas Id through Ik, R and $R^1$ each independently is a hydrogen atom or an alkyl group containing from 1 to 3 carbon atoms, for example, a methyl, ethyl or n-propyl group, and also isopropyl in formula Ig when novel. A further preferred subclass of the invention is when R is an alkyl group containing from 1 to 2 carbon atoms, i.e. a methyl or ethyl group and $R^1$ is an alkyl group containing from 1 to 3 carbon atoms, e.g. a methyl, ethyl, n-propyl or isopropyl group. Subject to any proviso stated above, novel compounds wherein R is a methyl group and $R^1$ is an isopropyl group are one preferred subclass, and compounds wherein R and $R^1$ each is an ethyl group are another preferred subclass;

each $R^3$ is preferably independently a hydrogen atom; a chlorine atom; a bromine atom; or an alkyl group containing 1 to 2 carbon atoms, i.e. a methyl or ethyl group. A further preferred subclass of the invention is when each $R^3$ is a hydrogen atom.

Preferably, $R^4$ is a hydrogen atom,

Preferably, each $R^5$ is a hydrogen atom or an alkyl group containing 1 or 2 carbon atoms, i.e. a methyl or ethyl group. A further preferred subclass is when each $R^5$ is a hydrogen atom.

A second preferred subclass of the invention is directed to novel compounds of formula II wherein m is 1, n is 1 and p is 2 in formula 1

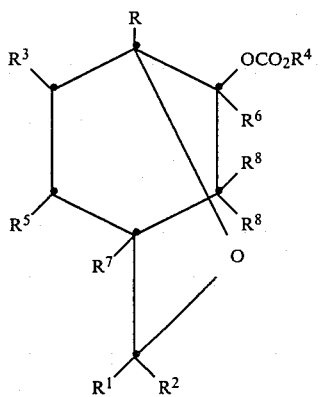

wherein both of Q are hydrogen atoms or fluorine atoms; R is a hydrogen atom, or a straight-chain alkyl group containing from 1 to 6 carbon atoms; $R^1$ and $R^2$ each independently is a hydrogen atom; or an alkyl group containing 1 or 2 carbon atoms; or $R^1$ and $R^2$ taken together form an alkylene group containing 4 or 5 carbon atoms; $R^3$ is a hydrogen atom; a hydroxy group; a benzyloxy group; or an alkoxy group containing 1 or 2 carbon atoms; $R^4$ is an alkenyl or alkynyl group containing from 2 to 4 carbon atoms; a 2-pyridinyl group; a 2-furanyl group; or a phenyl group optionally substituted by one or more substituents independently selected from a halogen atom, each having an atomic number of from 9 to 35, inclusive; or an alkoxy or alkylthio group containing from 1 to 3 carbon atoms, each optionally substituted by one or more halogen atoms, each having an atomic number of 9 or 17, or by an alkyl group containing 1 or 2 carbon atoms optionally substituted by one or more halogen atoms having an atomic number of 9 or 17, hydroxy, alkoxy of 1 or 2 carbon atoms or alkylthio of 1 or 2 carbon atoms; $R^5$, $R^6$, $R^7$ and $R^8$ each independently is a hydrogen atom; or an alkyl group containing from 1 to 4 carbon atoms.

Non-limiting examples of this subclass II of compounds of the invention include:
6-(2,6-difluorobenzyloxy)-1,3,3-trimethyl-2-oxabicyclo[2.2.2]octane,
6-(benzyloxy)-1-ethyl-3,3-dimethyl-2-oxabicyclo[2.2.2]octane,
6-(2-(trifluoromethyl)benzyloxy)-1-ethyl-3,3-dimethyl-2-oxabicyclo[2.2.2]octane,
6-(2-bromobenzyloxy)-1-methyl-3,3-diethyl-2-oxabicyclo[2.2.2]octane,
6-(2,6-dimethylbenzyloxy)-1,3,3-trimethyl-2-oxabicyclo[2.2.2]octane,
6-(2,4-dichlorobenzyloxy)-1,3,3-triethyl-2-oxabicyclo[2.2.2]octane,
6-(2-(trifluoromethyl)benzyloxy)-1-methyl-3,3-diethyl-7-(syn and anti)hydroxy-2-oxabicyclo[2.2.2]octane,
6-(benzyloxy)-1,3,3-trimethyl-7-(syn and anti)chloro-2-oxabicyclo[2.2.2]octane,
6-(2,6-dichlorobenzyloxy)-1-ethyl-3,3-dimethyl-7-(syn and anti)bromo-2-oxabicyclo[2.2.2]octane,
6-(4-fluorobenzyloxy)-1,3,3-trimethyl-7-(syn and anti)-methoxy-2-oxabicyclo[2.2.2]octane,
6-(2-methylbenzyloxy)-1-methyl-3,3-diethyl-7-(syn and anti)ethoxy-2-oxabicyclo[2.2.2]octane,
6-(2-furanyloxy)-1,3,3-trimethyl-2-oxabicyclo[2.2.2]octane,
6-(benzyloxy)-1,3,3,8-tetramethyl-2-oxabicyclo[2.2.2]octane,
6-(2-propenyloxy)-1,3,3,4-tetramethyl-2-oxabicyclo[2.2.2]octane,
6-(2-fluorobenzyloxy)-1,3,3,4-tetramethyl-2-oxabicyclo[2.2.2]octane,
6-(2-butynyloxy)-1,3,3,6-tetramethyl-2-oxabicyclo[2.2.2]octane,
6-(2-fluorobenzyloxy)-1,3,3,6-tetramethyl-2-oxabicyclo[2.2.2]octane,
6-(3-(trifluoromethyl)benzyloxy)-1,3,3,5-tetramethyl-2-oxabicyclo[2.2.2]octane,
6-(2-fluorobenzyloxy)-1,3,3,5-tetramethyl-2-oxabicyclo[2.2.2]octane,
6-(2,6-dimethoxybenzyloxy)-1,3,3,5,5-pentamethyl-2-oxabicyclo[2.2.2]octane,
6-(2-fluorobenzyloxy)-1,3,3,5,5-pentamethyl-2-oxabicyclo[2.2.2]octane,
6-(2-chlorobenzyloxy)-1,3,3,8-tetramethyl-2-oxabicyclo[2.2.2]octane,
6-(2-methylbenzyloxy)-1,4-dimethyl-2-oxabicyclo[2.2.2]octane,
6-(2,6-dichlorobenzyloxy)-1,3,4-trimethyl-2-oxabicyclo[2.2.2]octane,
6-(benzyloxy)-1,3-dimethyl-2-oxabicyclo[2.2.2]octane,
and the 6-endo and the 1S-6-endo forms of the above compounds.

In the compounds of formula II, preferably, R is a hydrogen atom or an alkyl group containing 1 or 2 carbon atoms, especially a methyl or ethyl group. A preferred subclass of the invention is directed to compounds wherein R is a methyl group.

Preferably, $R^1$ and $R^2$ each independently is a hydrogen atom, an alkyl group containing 1 or 2 carbon atoms, such as methyl or ethyl, or when taken together is a tetramethylene or pentamethylene or pentamethylene group. A preferred subclass of the invention is directed to compounds wherein $R^1$ and $R^2$ both are methyl or ethyl groups.

Preferably, all of Q and $R^3$, $R^5$, $R^6$, $R^7$ and $R^8$ are hydrogen atoms.

Preferably, $R^4$ is an ethynyl group, a 2-pyridinyl group, a phenyl group or an optionally substituted phenyl group, for example, a 4-fluorophenyl, a 2-chlorophenyl, a 2-fluorophenyl, a 2,6-dichlorophenyl, a 2,6-difluorophenyl, a 2-methylphenyl, a phenyl group or the like, and especially compounds wherein $R^4$ is a phenyl group substituted at the 2-, or 2- and 6-position by a chlorine atom, a fluorine atom or a methyl group. One preferred subclass of the invention is directed to compounds wherein $R^4$ is a 2-methylphenyl group.

Another preferred subclass of the invention is directed to compounds wherein $R^4$ is a 2-fluorophenyl group.

The materials of formula II that have the $R^4CH_2O$ group endo (formula IIa below) are usually more herbicidally active than the exo form (formula IIb below) or the endo-exo mixture and are preferred.

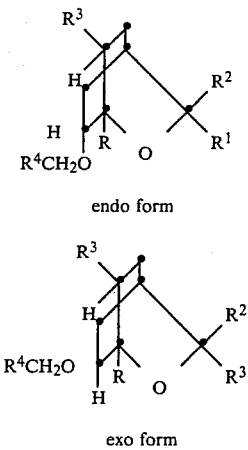

Formula IIa
endo form

Formula IIb
exo form

When $R^3$ is hydrogen, then the compounds of formula IIa and IIb have the 1S absolute configuration shown above. Such compounds of the subclass of formula IIa of the invention that correspond in configuration are preferred. When an isomer or a mixture of isomers other than a racemic mixture is used substantially free of all other possible isomers, they are usually about 70% pure, although a purity above about 80% is preferable and a purity above about 95% is highly desirable. This invention contemplates all of the herbicidally active isomers, as well as any mixture resulting from the synthesis methods used, and deliberately created mixtures.

Because of their properties, an especially preferred further subclass of the invention is directed to compounds of formula IIc

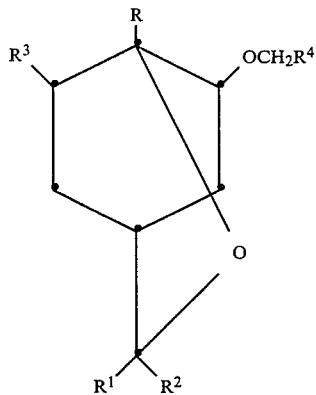

IIc wherein R is a hydrogen atom or a straight chain alkyl group containing from 1 to 4 carbon atoms; $R^1$ and $R^2$ each independently is a hydrogen atom or an alkyl group containing from 1 to 2 carbon atoms optionally substituted by up to 4 halogen atoms having an atomic number of 9 or 17, inclusive, or $R^1$ and $R^2$ when taken together form an alkylene group containing 4 or 5 carbon atoms; $R^3$ is a hydrogen atom, a hydroxy group or an alkoxy group containing 1 or 2 carbon atoms; and $R^4$ is an ethynyl group, a 2-pyridinyl group, a 2-furanyl group or a phenyl group optionally substituted by one or more substituents independently selected from a halogen atom having an atomic number of from 9 to 35, inclusive, or by an alkoxy or alkylthio group containing from 1 to 2 carbon atoms each optionally substituted by one or more halogen atoms having an atomic number of 9 or 17, or by an alkyl group containing 1 or 2 carbon atoms optionally substituted by one or more halogen atoms having an atomic number of 9 or 17, hydroxy, alkoxy of 1 or 2 carbon atom or alkylthio of 1 or 2 carbon atoms.

Because of their herbicidal activity, preferably R is a methyl group and $R^1$ and $R^2$ each independently is a methyl group or an ethyl group $R^1$ and $R^2$ when taken together is a tetramethylene or pentamethylene group. A further preferred subclass of the invention is when $R^1$ and $R^2$ are both methyl or ethyl groups. $R^3$ is preferably a hydrogen atom. $R^4$ is preferably an ethynyl group, a 2-pyridinyl group, a phenyl group, or an optionally substituted phenyl group, for example, a 4-fluorophenyl, a 2-chlorophenyl, a 2-fluorophenyl, a 2-methylphenyl, a 2,6-dichlorophenyl group or the like. A preferred subclass of the invention is directed to compounds wherein $R^4$ is a phenyl group substituted at the 2-, or 2- and 6-positions by a chlorine atom, a fluorine atom or a methyl group. One preferred subclass of the invention is directed to compounds wherein $R^4$ is a 2-methylphenyl group. Another preferred subclass of the invention is directed to compounds wherein $R^4$ is a 2-fluorophenyl group.

The Compounds of the Invention described by formula 1 are prepared by treating the appropriately substituted oxabicycloalkanol with a compound of the formula $WCQ_2X$ in which X is a halogen atom, such as bromine, chlorine, or iodine, or is a mesyloxy, tosyloxy group or the like, preferably in the presence of a strong base and an inert diluent, and preferably in the presence of a catalyst. The strong base is suitably an alkali metal hydride, hydroxide or carbonate, including, for example, sodium hydride, sodium hydroxide, potassium carbonate and the like. Inert diluents are suitably organic solvents, such as ethers, aromatic hydrocarbons, chlorinated hydrocarbons and the like, including, for example, diethyl ether, tetrahydrofuran, dimethyl sulfoxide, toluene, methylene chloride and the like. Suitable catalysts are organic bases, such as tertiary amines and ammonium compounds, for example, triethylamine, and the like. The reaction is usually carried out under normal pressures and ambient temperatures. Suitable temperatures for the reaction are from about 0° to 120° C., preferably from about 20° to about 100° C. The product ethers are recovered and isolated by conventional techniques. In some cases, the ethers may be formed prior to the ring closure to the oxabicycloalkane system.

The oxabicycloalkanol reactants are obtained generally by one or more of the following routes: directly by (a) epoxidation-cyclization of unsaturated cyclic alcohols, with or without isolation of epoxy alcohol intermediates; and indirectly by (b) photochemical ring closure of unsaturated ketones; (c) ring contraction of diazo ketones; (d) Diels-Alder reactions of furans with dienophiles.

Detailed routes are described below for the different ring systems.

In (a), the epoxidation-cyclization of unsaturated cyclic alcohols involves treatment by an oxidizing agent followed by an acid. The alcohols are either (i) cycloalk-3-en-1-ols, or (ii) cycloalk-3-ene-1-methanols. The cycloalk-3-en-1-ols are prepared from cycloalk-3-en-1-yl dialkyloxiranes: by reduction; by addition of HX, in which X is OH, Cl, OR, SR, $NR_2$ in which R is H, alkyl, aryl or aralkyl as appropriate for the definition of $R_3$ in Formula 1, $N_3$, or $P(O)OR_2$, to cycloalk-3-en-1-yl dialkyloxiranes; by rearrangement of cycloalk-3-en-1-yl dialkyloxiranes; by reduction of cycloalk-3-en-1-ones; by treatment of cycloalk-3-en-1-ones with a Grignard reagent; by dealkylating or hydrolyzing, respectively, Diels-Alder adducts of vinyl ethers are esters prepared from dienes, such as isoprene, and vinyl ether or ester dienophiles in which the alpha-position of the vinyl group is substituted by alkyl, $CO_2R^8$, or $CON(R^8)_2$, by ring contraction of certain other oxabicyclo-alkanols of the invention using conventional chemistry of from known cycloalkenoic acids, with or without homologation using conventional chemistry. The acids are known in the art or are prepared by known homologation procedures from known acids. The cycloalk-3ene-1-methanols are (1) α-terpineol; (2) Diels-Alder adducts of allylic alcohols; or (3) products obtained from Diels-Alder adducts of alpha-beta unsaturated carbonyl compounds, such as acrylates, crotonates, aldehydes or ketones, by reduction or treatment with a Grignard reagent.

In (b), the photochemical ring closure is accomplished by application of conventional techniques on unsaturated ketones, such as described in Furth, et al., *Tetrahedron Letters*, No. 48, pages 4259–62 (1975) for unsaturated ketones.

In (d), the Diels-Alder type adducts of furans with dienophiles may require vigorous reaction conditions, including high pressure and low temperature, for example, as described in Dauben, W. G. et al., *J. Amer. Chem. Soc.*, 102, page 6894 (1980). When the dienophile is nitroethylene, the resulting product is hydrogenated, then oxidized to the ketone and reduced to the corresponding alcohol, e.g. by treatment with a hydride or metal. When this alcohol has the endo form, it can be epimerized with base or aluminum isopropoxide in the presence of a ketone to the corresponding exo alcohol.

Endo- and exo-oxabicycloalkanol intermediates can be separated by conventional methods, such as crystallization, chromatography and the like, and the geometrics forms can be resolved by classical resolution methods to give a substantially pure single isomer.

Non-limiting illustrations of the preparation of representative Compounds of the Invention follow.

(I) When m is 1, n is 0 and p is 2, the ring is a 7-oxabicyclo[2.2.1]heptane. For example, a compound of subclass I of the formula Ip, below

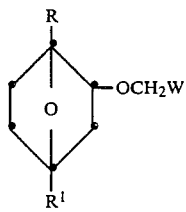

Ip in which R and $R^1$ in formula Ip correspond with $R_2$ and $R_3$ in formula 1 and in which R is methyl and $R^1$ is isopropyl, can be prepared by aralkylation of 7-oxabicyclo[2.2.1]heptan-2-ols (Id) obtained from (1) cyclohex-3-en-1-ols (Ig), by epoxidation-cyclization, or (2) Diels-Alder adducts of furans, such as 2,5-dimethylfuran, with dienophiles, such as nitroethylene, as described below.

The epoxidation of cyclohex-3-en-1-ols into the corresponding cis-epoxy-alcohol is effected by action of an oxidizing agent, particularly, a peroxide, such as m-chloroperbenzoic acid, peracetic acid, tert-butyl hydroperoxide (TBHP) or equivalent peroxide reagents. Preferably, the oxidation with TBHP is conducted in the presence of an appropriate transition metal catalyst. Suitable transition metal catalyst are complexes of metals of atomic numbers 22–31, 40–49 and 72–81. Preferably, the complex is an organic complex, for example, with beta-diketones, o-hydroxybenzaldehydes or o-hydroxybenzophenones and particularly with acetylacetone. While any of these transition metal catalysts can be used, those of vanadium or molybdenum are preferred; for example, vanadium(VI) bis(2,4-pentanedionate) oxide is preferred. The reaction is suitably conducted in the presence of an inert solvent such as chlorinated hydrocarbons, ethers, hydrocarbons or the like. Suitable chlorinated hydrocarbons contain from 1 to 4 chlorine atoms in combination with an alkane chain containing from 1 to 4 carbon atoms or a benzene ring, for example, carbon tetrachloride, chloroform, dichloromethane, chlorobenzene and 1,2- or 1,3-dichlorobenzene and the like. Ethers are generally those containing from 4 to 6 carbon, for example, diethyl ether, methyl tert-butyl ether and diisopropyl ether. Tetra-hydrofuran and dioxane are also useful. Suitable alkanes contain from 5 to 10 carbon atoms, for example, n-pentane, n-hexane, n-heptane, n-octane, n-nonane, n-decane and their isomers. Petroleum fractions rich in alkanes are also suitable. Petroleum ether is also suitable. Cyclohexane and methylcyclohexane are examples of useful cycloalkane solvents containing from 6 to 8 carbon atoms. Suitable aromatic hydrocarbon solvents contain from 6 to 10 carbon atoms, for example, benzene, toluene, o-, m-, and p-xylene, the trimethylbenzenes, p-ethyltoluene and the like. The reaction is conducted at temperatures conveniently in the range of from about −10° C. to about 50° C. or slightly above. Generally, the temperature is from about −5° C. to about 40° C., preferably from about 10° C. to about 30° C. The molar ratio of reactants can vary. Generally, a molar ratio of cyclohex-3-en-1-ol to oxidizing agent is from about 0.8 to about 1.0. The reaction is usually conducted by forming a mixture of the alcohol and oxidizing agent, preferably while agitating the reaction mixture, e.g. by stirring, and maintaining the desired reaction temperature. The resulting product epoxy-alcohol may be purified or converted without isolation into the 2-exo-hydroxy-7-oxabicyclo[2.2.1]heptane by cyclization as described below.

The cyclization (ring closure) step surprisingly gave a high yield of product having the exo-hydroxy configuration in the resulting 7-oxabicyclo[2.2.1]heptan-2-ol. Many acids will catalyze this reaction, but a relatively strong acid such as sulfuric or sulfonic acids are suitable. Preferably, the acid is methanesulfonic aicd or any arylsulfonic acid, such as p-toluenesulfonic, benzenesulfonic acids, or the like. Of these, p-toluenesulfonic acid is preferred. The reaction is suitably conducted by adding the acid to the epoxy-alcohol contained in a solvent of the type previously described for use in the preparation of the epoxy-alcohol. The reaction is conducted at a temperature conveniently in the range of from about 0° C. to about 50° C. or slightly above. Generally, the temperature is from about 5° C. to about 40° C., preferably from about 10° C. to about 30° C. The molar ratio of reactants can vary. Generally, the molar ratio of acid to epoxy-alcohol is from about 0.01 to about 0.10, and preferably from about 0.02 to about 0.04.

Thus, a 1,4-disubstituted-3-cyclohexen-1-ol is converted mainly to 2-exo-hydroxy-1,4-disubstituted-7-oxabicyclo[2.2.1]heptane by treating it with an oxidizing agent, such as tert-butyl hydroperoxide, or m-chloroperbenzoic acid, and then a strong acid, such as p-toluene-sulfonic acid. Especially useful for obtaining a 2-exo-hydroxy-1,4-disubstituted-7-oxabicyclo[2.2.1]heptane is treatment of the corresponding 3-cyclohexen-1-ol with tert-butyl hydroperoxide and vanadium-(IV) bis(2,4-pentanedionate) oxide as catalyst in methylene chloride followed by treatment of the intermediate epoxide, preferably in situ, with a sulfonic acid, particularly p-toluenesulfonic acid. Also, acid present during the epoxidation step produces the desired product. The epoxidation-cyclization is disclosed and claimed in co-pending U.S. patent application Ser. No. 331,095, filed Dec. 16, 1981.

In situations where the endo form is desired, it can be obtained by oxidation of the 2-exo-hydroxy compound to the corresponding ketone followed by reduction of the ketone with sodium borohydride.

The 3-cyclohexen-1-ols (Ig), useful for the preparation of Compound Ip can be synthesized as described below or obtained from natural sources (which offer the advantage of optically-active materials).

(a) where R is methyl and $R^1$ is isopropyl and the remaining R's are hydrogen, the compound is terpinen-4-ol, which occurs naturally. Terpinen-4-ol is converted to 2-exo-hydroxy-1-methyl-4-isopropyl-7-oxabicyclo[2.2.1]heptane by treatment with an oxidizing agent, for example, a peroxide such as m-chloroperbenzoic acid, peracetic acid or tert-butyl hydroperoxide. The optical configuration of terpinen-4-ol is retained in the reaction. Thus, ($\pm$), ($-$) or ($+$) 2-exo-hydroxy-1-methyl-4-isopropyl-7-oxabicyclo[2.2.1]heptane can be obtained. 2-endo-Hydroxy-1-methyl-4-isopropyl-7-oxabicyclo[2.2.1]heptane is known from Garside et al., J. Chem. Soc., page 716–721 (1969). 2-exo- and endo-Hydroxy-1-methyl-4-isopropyl-7-oxabicyclo[2.2.1]heptanes are converted to the ethers of the invention as described above. Although terpinen-4-ol occurs in nature in optically active and racemic forms, it can also be prepared by epoxidation of terpinolene, e.g. with peracetic acid in methylene chloride, followed by reduction of the epoxide, e.g. with sodium diethylaluminum hydride in tetrahydrofuran.

(b) Substituted-1-oxaspiro(2.5)oct-5-enes are useful for preparing 3-cyclohexen-1-ols where $R^1$ is substituted by OH, OR, SR, $NR_2$, $N_3$, $P(O)(OR)_2$. Treatment of a 1-oxaspiro(2.5)oct-5-ene with water or an alcohol in the presence of a strong acid affords the corresponding 3-cyclohexen-1-ol substituted in the 1-position by a hydroxymethyl or alkoxymethyl group. Treatment of 1-oxaspiro(2.5)oct-5-ene with thiophenol, or an alkyl, $C_{6-11}$ aryl, or $C_{7-11}$ aralkyl mercaptan, in the presence of a catalyst, such as sodium hydride, and a suitable solvent, produces correspondingly a thio-substituted 3-cyclohexen-1-ol that can be converted to the corresponding sulfonyl derivative in the course of the oxidation process described above. Where $R^1$ is halo-substituted, the haloalkyl-substituted-3-cyclohexen-1-ol is prepared by treating a spiro compound as defined above with an ethereal hydrohalogenic acid, e.g. hydrochloric acid. The resulting halo-substituted-3-cyclohexen-1-ol is converted to the desired ether of the invention as described above. The (chloroalkyl)-substituted ethers of the invention made by treatment of the spiro compound with HX in which X is halogen can then be dehydrochlorinated to yield the corresponding 4-alkenyl-substituted ethers of the invention (where $R^1$ is alkenyl) with the use of a base. Compounds where $R^1$ is alkenyl are also made by rearrangement of the spiro compounds upon treatment with protic or Lewis acids. Where $R^1$ is substituted by an amine oxide group, a spiro compound as defined above is treated with the appropriate dialkylamine in the presence of a catalyst such as triethylaluminum; the subsequent epoxidation step produces the amine oxide. Where $R^1$ is dialkoxyphosphonylalkyl, the compounds may be prepared by treatment of a 1-oxaspiro[2.5]oct-5-ene with the appropriate phosphite ester.

(c) Preparation of 3-cyclohexen-1-ols can be effected from p-substituted phenols in which the substituent group corresponds to R in the formula I of the invention by procedures of the literature for the Birch-type reduction of derivatives of benzene, many of which are detailed in Rodd's Chemistry of Carbon Compounds, Second Edition, Vol. II, Part B, pages 1–4 (1968). In an example, a p-substituted phenol is first methylated to protect the hydroxy group yielding the corresponding p-alkylanisole. This p-alkylanisole is treated with a reducing agent such as lithium-ammonia or sodium-ammonia and the resulting product is hydrolyzed to yield the corresponding 4-substituted-3-cyclohexen-1-one. Treatment of this ketone with an appropriate organometallic (Grignard) reagent, $R^1MgBr$ or $R^1Li$ in which $R^1$ corresponds to that in the formula I of the invention and is alkyl or alkenyl, e.g. at 20°–60° C. in the presence of anhydrous ethers, yields the desired 1,4-disubstituted-3-cyclohexen-1-ol intermediate. The 4-substituted-3-cyclohexen-1-one can also be reduced, e.g. by hydrides, to the corresponding 3-cyclohexen-1-ol unsubstituted in position-4. When $R^1$ is alkenyl, this double bond can be treated (after ring closure) with HX or $X_2$ in which X is chlorine or bromine, or with RSH in which R is $C_{1-6}$ alkyl, phenyl or benzyl to give differently substituted products.

Where $R^1$ is substituted by CN, a 4-substituted-3-cyclohexen-1-one is treated with an alpha-bromoalkanenitrile in the presence of zinc dust. The resulting 1-hydroxy-alpha,alpha,4-trisubstituted-3-cyclohexenacetonitrile is cyclized and converted to the desired ether of the invention as described above.

Where $R^1$ is $-CO_2R^6$, $-CON(R^6)_2$, $-CN$, $-CSNH_2$, as well as alkyl, the 3-cyclohexen-1-ols can be prepared starting from suitable Diels-Alder adducts. For example, methyl pyruvate is converted by known procedures to its enol acetate and the latter is treated with isoprene to produce a Diels-Alder adduct. Hydrolysis of the acetaate function affords 1-hydroxy-4-methyl-3-cyclohexene-1-carboxylic acid methyl ester, which can be converted to compounds of the invention by the epoxidation-cyclization and aralkylation procedures described above. Treatment of compounds of the invention where $R^1$ in I is methoxycarbonyl with ammonia gives the $-CON(R^6)_2$ compound where $R^6=H$, and dehydration of the latter with thionyl chloride affords the compound of the invention where $R^1$ is cyano. Treatment of the latter with hydrogen sulfide affords the corresponding $CSNH_2$ compound. The compounds where $R^1$ is acetyl are prepared by treating the 4-isopropenyl compound, e.g. with osmium tetroxide in t-butanol followed by sodium metaperiodate. The compounds wherein $R^1$ is an oxime group are prepared by treating the 4-acetyl compound with a hydroxylamine or an alkoxyl- or alkenoxylamine. The compounds wherein $R^1$ is an acetal group are prepared by treating the 4-acetyl compound with an anhydrous alcohol and mineral acid.

The 2-hydroxy-7-oxabicyclo[2.2.1]heptanes useful as precursors of compounds of the invention can also be prepared from Diels-Alder adducts of suitably-substituted furans, as dienes, and dienophiles. For example, 2,5-dimethylfuran adds readily to nitroethylene to give 1,4-dimethyl-2-nitrobicyclo[2.2.1]hept-5-ene. Similar adducts can be prepared from 2,5-dialkylfurans and dienophiles such as acrolein and acrylate esters.

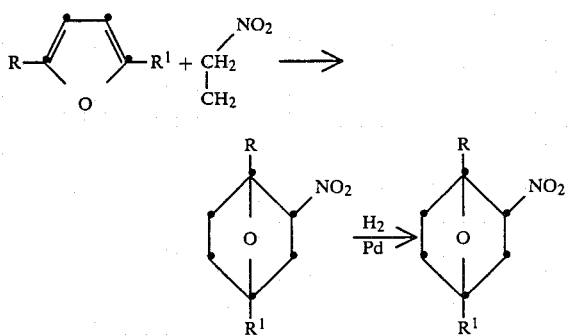

Severe reaction conditions including low temperature and high pressure may be required for some Diels-Alder reactions of substituted furans, for example, as described in Dauben, W. G. et al., *J. Am. Chem. Soc.*, 102, page 6894 (1980). Hydrogenation and treatment of the nitro compound with a strong base such as potassium hydroxide, followed by an oxidizing agent, such as potassium permanganate, singlet oxygen, aqueous $TiCl_3$, tert-butyl hydroperoxide in the presence of vanadium(IV) bis(2,4-pentanedionate)oxide or the like, affords the 1,4-disubstituted bicyclo[2.2.1]heptan-2-one. Reduction with a hydride or metal converts the ketone to the desired 2-hydroxybicyclo[2.2.1]heptane useful for preparation of compounds of the invention by aralkylation. Where the hydroxy group is in the endo orientation, epimerization to the more desirable 2-exo-hydroxy stereoisomer can be effected by treatment with a base, such as sodium hydroxide, or aluminum alkoxide in the presence of a ketone, preferably the corresponding ketone.

(2) When m is 1, n is 1 and p is 2, the ring is an oxabicyclo[2.2.2octane. For example, compounds of subclass II of the formula IIp

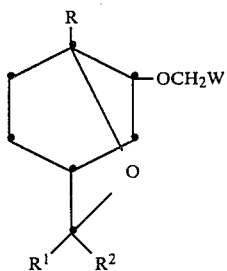

(in which R, $R^1$ and $R^2$ are methyl in formula 1), can be prepared by aralkylation of 2-oxabicyclo[2.2.2]heptan-6-ols made from (1) terpenes, such as alpha-terpineol or (2) Diels-Alder adducts of suitably substituted butadienes and dienophiles containing an oxygen function, as illustrated below.

(1) Compounds wherein R, $R^1$ and $R^2$ are methyl are obtained from naturally occuring terpenes. Most elementarily, alpha-pinene is treated with aqueous acid to form alpha-terpineol, itself a naturally occuring material. alpha-Terpineol, either in racemic form or completely or partially optically active form, is oxidized, for example, with a peroxide such as hydrogen peroxide or m-chloroperbenzoic acid in a suitable solvent like methylene chloride, to yield a major amount of 1,3,3-trimethyl-2-oxabicyclo[2.2.2]octan-6-exo-ol. Oxidation of this alcohol, e.g. with N-bromoacetamide in aqueous acetone at 5° C., gives 1,3,3-trimethyl-2-oxabicyclo[2.2.2]octane-6-one. Subsequent reduction of this ketone, for example with sodium borohydride in tert-butanol, yields a mixture of alcohols predominant in the endo isomer. Conversion to the ether of formula II of the Invention follows the earlier described procedures with retention of configuration.

(2) Diels-Alder adducts are formed from suitable, readily available dienophiles including an acrylate ester, acrolein, methacrolein, methyl vinyl ketone, allyl alcohol, a crotonate ester and the like. The diene component is isoprene, 2,3-dimethylbutadiene and the like. For example, the Diels-Alder adducts IId are prepared by treating an R-alkyl-substituted diene component (isoprene; R=methyl) corresponding to the portion of the compound of formula IId above the dotted line

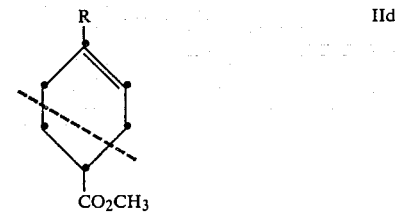

with a dienophile (methyl acrylate) corresponding to the portion of the compound of formula IId below the dotted line. Many such reactions are detailed in Rodd's Chemistry of Carbon Compounds, Second Edition, *Vol II, Part B*, pages 5–6 (1968). Treatment of IId with the appropriate Grignard reagent (e.g. methyl magnesium bromide, ethyl magnesium bromide or the like) gives an alpha,alpha,4-trialkyl-cyclohexene-1-methanol of formula IIe below.

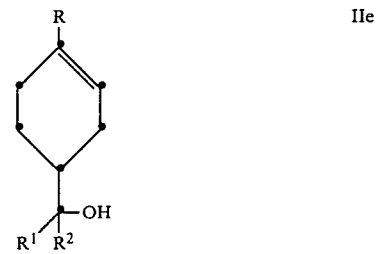

Alcohol IIe is oxidized, for example, with a peroxide, such as hydrogen peroxide or m-chloroperbenzoic acid, in a suitable solvent, such as methylene chloride, preferably in the presence of a strong acid, to yield a major amount of 1,3,3-trialkyl-2-oxabicyclo[2.2.2]octan-6-exool. This exo form can be converted, if desired, into an endo-rich or substantially pure endo form. First, oxidation to the corresponding ketone, 1,3,3-trialkyl-2-oxabicyclo[2.2.2]octan-6-one, is effected with a suitable oxidizing agent. For example, the exo form is combined with oxalyl chloride and dimethyl sulfoxide in methylene chloride followed by addition of triethylamine. Then, the resulting ketone is converted into the endo-alcohol by reduction. For example, the ketone in a mixture of dimethoxyethane and tert-butanol is treated with sodium borohydride. Classical resolution can be applied to the 1,3,3-trialkyl-2-oxabicyclo[2.2.2]octan-6-ols to give substantially pure individual optical forms.

The 1,3,3-trialkyl-2-oxabicyclo[2.2.2]octan-6-ols are converted into the desired ethers of the Invention, with retention of configuration, by treatment with a halide $R^4CH_2X$ in which X is a halogen atom, such as chlorine, and $R^4$ corresponds to a group as defined in formula II of the invention. This reaction is carried out, preferably in the presence of a base, such as sodium hydride, and, if desired, an inert solvent, such as N,N-dimethylacetamide, N,N-dimethylformamide, benzene, toluene or the like. The compounds of the invention can be recovered and purified by conventional techniques.

In accordance with the above teachings, other ethers of the invention are similarly made. Non-limiting illustrations of such procedures include the following techniques in which for simplicity most of the various R groups and Q in formula 1 are shown as hydrogen atoms.

(III) When m is 1, n is 1 and p is 1 in formula 1, IIIp represents another subclass of compounds of the invention.

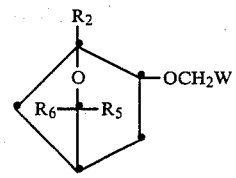

For example, compounds IIIp in which $R_2$, $R_5$ and $R_6$ are methyl can be prepared by condensation of 1,4-dibromo-2-methyl-2-butene with an alkyl acetoacetate, in the presence of base, followed by thermolysis of the isopropenyl acetal cyclopropanecarboxylate intermediate to a cyclopentene carboxylate, which is hydrolyzed and decarboxylated to the corresponding ketone. Treatment of the ketone with a Grignard reagent, methyl magnesium bromide, yields the corresponding alcohol derivative. This alcohol is epoxidized and cyclized to an exo-2-oxabicyclo[2.2.1]heptan-6-ol. This exo-alcohol can be oxidized to the corresponding ketone followed by reduction to a corresponding endo-2-oxabicyclo[2.2.1]heptan-6-ol as described for the compounds of formula IIp above. The alcohol is treated with $WCH_2X$ in which X is halogen to yield the desired ether IIIp. An example of one alternative method is the condensation of a 1,4-dibromo-2-methyl-2-butene with a malonic acid dialkyl ester, again using base, followed by thermolysis. The resulting cyclopentene derivative is treated with, e.g., sodium chloride in dimethyl sulfoxide to eliminate one of the ester functional groups. Treatment of the resulting mono ester with the Grignard reagent, methyl magnesium bromide, yields the alcohol derivative previously described in the first methodology. See, also, Spurlock et al., *Chemical Abstracts*, 76:153024e (1972) for preparation of a 2-oxabicyclo[2.2.1]heptan-6-ol.

(IV) When m is 0, n is 1 and p is 2 in formula 1, IVp represents another subclass of compounds of the invention. For example, Compounds of formula IVp

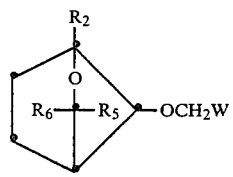

in which $R_2$, $R_5$ and $R_6$ are methyl can be prepared from a 2-oxabicyclo[2.2.2]octan-6-ol corresponding to formula IIp as follows. The octanol is treated with oxalyl chloride in dimethyl sulfoxide, and the resulting ketone is treated successively with (1) potassium tert-butoxide, and butyl nitrite and then (2) sodium hypochlorite, aqueous sodium hydroxide and concentrated ammonium hydroxide or is converted to a formylketone (analogous to the method of C. Ainsworth, *Organic Syntheses, IV,* page 536 (1963)), which in turn is converted to a diazoketone analogous to the method of M. Regitz et al., *Organic Syntheses,* 51, page 86 (1971). The resulting diazo derivative is irradiated. The resulting ring-contracted carboxylic acid is treated successively with thionyl chloride, m-chloroperbenzoic acid and sodium hydroxide to yield a 2-oxabicyclo[2.2.1]heptan-7-ol, which is treated with $WCH_2X$ in which X is halogen to yield the desired ether IVp. Alternatively, compounds of formula IVp, in which $R_2$, $R_5$ and $R_6$ are methyl, can be prepared by treatment of methyl 3-methyl-cyclopent-2-enecarboxylate, obtained by the procedure described by C. A. Bunnell and P. L. Fuchs, *J. Am. Chem. Soc.,* 99, 5184 (1977), with methyl magnesium bromide to introduce the $R_5$ and $R_6$ substituents. The resulting alcohol is epoxidized and cyclized to yield a 2-oxabicyclo[2.2.1]heptan-7-ol.

(V) When m is 1, n is 0 and p is 1 in formula 1, the ring system is subclass V of the formula Vp below. For example, the Compound Vp

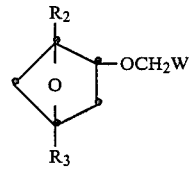

in which $R_2$ is methyl and $R_3$ is isopropyl in formula 1 can be prepared by photochemical ring closure of $(CH_3)_2CHC(O)CH_2CH(OCH_2C_6H_5)C(CH_3)=CH_2$ by techniques such as in the earlier mentioned Furth et al. reference to yield a 5-oxabicyclo[2.1.1]hexan-2-ol ether Vp, in which W in the above formula is phenyl.

(VI) When m is 0, n is 0 and p is 2 the ring system is a 5-oxabicyclo[2.1.1]hexane and represents another subclass of this invention. For example, compound VIp below

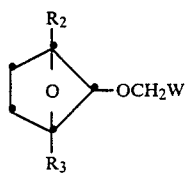 VIp

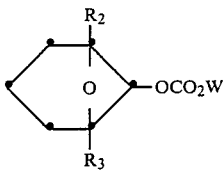 VIIIp in which $R_2$ is methyl and $R_3$ is isopropyl can be prepared by photochemical ring closure of $(CH_3)_2CHC(O)CH_2CH_2C(CH_3)=CHOCH_2C_6H_5$ by techniques such as the earlier mentioned Furth et al. reference to yield the 6-benzyloxy-5-oxabicyclo[2.1.1.-]hexane in which W in the above formula is phenyl.

Alternatively, a 7-oxabicyclo[2.2.1]heptane-2-one is treated either (1) successively with potassium tert-butoxide and butyl nitrite and then with an aqueous mixture of sodium hypochlorite, sodium hydroxide and concentrated ammonium hydroxide, or (2) is converted to the alpha-formyl ketone, which in turn is converted to the corresponding diazoketone analogously to the method described in IV. The diazoketone is irradiated in methanol. The resulting ring contracted carboxylate ester is saponified with one equivalent of lithium hydroxide, and the dry lithium carboxylate is treated with methyl lithium in tetrahydrofuran. The resultant methyl ketone is subjected to Baeyer-Villiger oxidation with m-chloroperbenzoic acid followed by hydrolysis with sodium hydroxide to yield the corresponding 5-oxabicyclo[2.1.1]hexan-6-ol, which is treated with $WCH_2X$ in which X is halogen to yield the desired VIp.

(VII) When m is 0, n is 1 and p is 1, the ring system is a 2-oxabicyclo[2.1.1]hexane, another subclass of this invention. For example, compound VIIp below

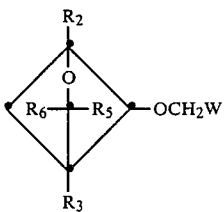 VIIp in which $R_2$, $R_3$, $R_5$ and $R_6$ are methyl can be prepared by photocycloaddition of methyl (meth)acrylate or methyl vinyl ketone to isopropenyl phenyl sulfide to form a cyclobutane derivative. Oxidation of this cyclic adduct followed by thermolysis removes the phenylthio moiety. Treatment of the resulting cyclobutene ester with methyl magnesium bromide introduces the $R_5$ and $R_6$ substituents. The resulting alcohol is epoxidized and cyclized to yield a 2-oxabicyclo[2.1.1]hexan-5-ol, which is treated with $WCH_2X$ in which X is halogen to yield the desired ether, VIIp. Alternatively, (isopropenylthio)benzene is photocyclized with methyl vinyl ketone or methyl acrylate, oxidized to a sulfoxide, heated, and then treated with methyl Grignard to yield the corresponding substituted-cyclobutene-alcohol. Epoxidation and cyclization of the above alcohol yields the desired 2-oxabicyclo[2.1.1]hexan-5-ol.

(VIII) When m is 0, n is 0 and p is 3, the ring system is a 6-oxabicyclo[3.1.1]heptane, another subclass of this invention. For example, a compound within subclass VIII of formula VIIIp below in which $R_2$ is methyl and $R_3$ is isopropyl in formula 1 can be prepared by photochemical ring closure of $(CH_3)_2CHC(O)CH_2CH_2CH_2C(CH_3)=CHOCH_2C_6H_5$ by techniques such as in the earlier mentioned Furth et al. reference to yield the 7-benzyloxy-6-oxabicyclo[3.1.1]hexane in which W in the above formula is phenyl. Alternatively, a compound within subclass VIII of formula VIIIp in which $R_2$ and $R_3$ are methyl can be prepared by oxidation of 2,5-dimethyl-8-oxabicyclo[3.2.1]octan-6-ol, as obtained by the method described for subclass X below, to the corresponding ketone, and subjecting the resulting ketone to a photochemical ring contraction and subsequent modification by the method previously outlined under case VIp to give a 6-oxabicyclo[3.1.1]heptan-7-ol which is treated with $WCH_2X$ to yield the desired ether.

(IX) When m is 0, n is 1 and p is 3, the ring system is a 6-oxabicyclo[3.2.1]octane, another subclass of this invention. For example, a compound IXp

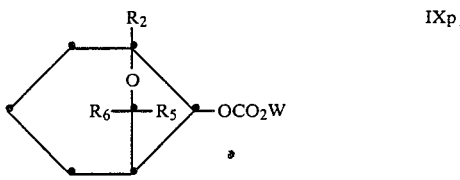 IXp in which $R_2$, $R_5$ and $R_6$ are methyl in formula 1 can be prepared from 3-methyl-2-cyclohexen-1-one by reduction, tosylation, followed by treatment with KCN or NaCN in the presence of a catalyst, such as a crown ether, and then subjecting the resulting nitrile to treatment with methyl Grignard to yield the corresponding methylated alcohol. Epoxidation and cyclization of the resulting alcohol yields the desired 6-oxabicyclo[3.2.1]octan-8-ol, which is treated with $WCH_2X$ in which X is halogen to yield the desired ether, IXp. One alternative method involves treatment of methyl 3-methylcyclohex-2-ene-1-carboxylate, obtained by a procedure described in Bunnell et al., *J. Amer. Chem. Soc.*, 99, page 5184 (1977), with methyl Grignard followed by epoxidation and cyclization of the resulting alcohol to yield 6-oxabicyclo[3.2.1]octan-8-ol.

(X) When m is 1, n is 0 and p is 3, the ring system is an 8-oxabicyclo[3.2.1]octane, another subclass of this invention. For example, compound Xp

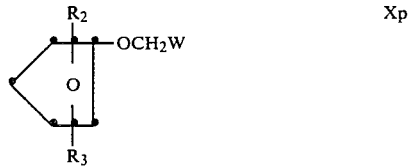 Xp in which $R_2$ and $R_3$ are methyl can be prepared by condensation of a substituted furan, e.g. 2,5-dimethylfuran, with 1,1,3,3-tetrabromo-2-propanone, followed by treatment of the adduct with zinc/silver couple to form an 8-oxabicyclo[3.2.1]oct-6-ene-3-one derivative, as described by Noyori, R., et al., *J. Org. Chem.*, 40, 806-7 (1975). Lithium aluminum hydride reduction of the ketone followed by treatment of this product with, e.g. tosyl chloride and then lithium triethylborohydride, yields the corresponding 8-oxabicyclo[3.2.1]oct-6-ene derivative. Successive treatment of this product with, e.g., boron hydride (borane) in tetrahydrofuran, hydrogen peroxide in the presence of base, and $WCH_2X$ in which X is halogen yields the desired ether, Xp.

(XI) When m is 0, n is 2 and p is 2, the ring system is a 2-oxabicyclo[3.2.1]octane, another subclass of this invention. For example, compound XIp,

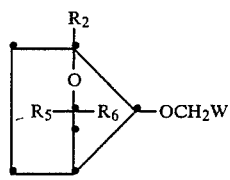

XIp in which $R_2$, $R_5$ and $R_6$ are methyl, can be prepared by conversion of 3-methylcyclopent-2-ene-1-carboxylic acid described in IV to the corresponding acid chloride with thionyl chloride. The resulting carboxylic acid chloride is subjected to a modified Arndt-Eistert homologation, as described by G. P. Kugatova-Sheinyakina and R. A. Poskiene, *Zh. Organ. Khim.*, 2(5), 844 (1966) (CA 65 10504c) to produce 3-methyl-2-cyclopentene-1-acetic acid, which is treated similarly to the acid of Subclass IX to yield the desired 2-oxabicyclo[3.2.1]octan-8-ol. The octanol is treated with $WCH_2X$ in which X is halogen to yield the desired ether, XIp.

(XII) When m is 1, n is 2 and p is 1, the ring syste is a 2-oxabicyclo[3.2.1]octane, another subclass of this invention. For example, compound XIIp

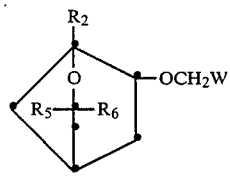

XIIp in which $R_2$, $R_5$ and $R_6$ are methyl, can be prepared by saponification and decarboxylation of diethyl 1-methylcyclopent-1-ene-4,4-dicarboxylate, prepared by the procedure of E. E. Schweiger and G. J. O'Neill, *J. Org. Chem.*, 30, 2082 (1965), to provide 1-methylcyclopent-1-ene-4-carboxylic acid. The resulting carboxylic acid is homologated in the manner proscribed for the compounds XIp, and subsequently treated similarly to the acid of subclass IX.

(XIII) When m is 0, n is 2 and p is 1, the ring system is a 2-oxabicyclo[3.1.1]heptane, another subclass of this invention. For example, compound XIIIp

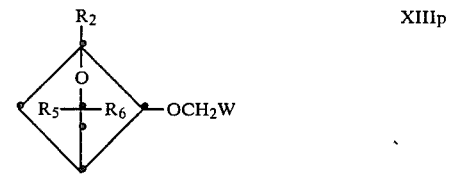

XIIIp in which $R_2$, $R_5$ and $R_6$ are methyl can be prepared from 3-methyl-2-cyclobuten-1-one by procedures similar to those described for subclass XII.

(XIV) When m is 1, n is 1 and p is 3, the ring is a 6-oxabicyclo[3.2.2]nonane. For example, a compund of subclass XIV of formula XIVp below

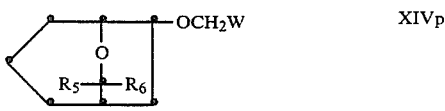

XIVp in which $R_2$, $R_5$ and $R_6$ are methyl can be prepared from 1-methylcyclohept-1-ene-4-carboxylic acid (obtained by the method of G. L. Buchanan et al., *Tetrahedron*, 23, 4729 (1967)) by treatment in the manner of the acid of subclass IX.

(XV) When m is 1, n is 2 and p is 2, the ring system is a 2-oxabicyclo[3.2.2]nonane, another subclass of this invention. For example, compound XVp

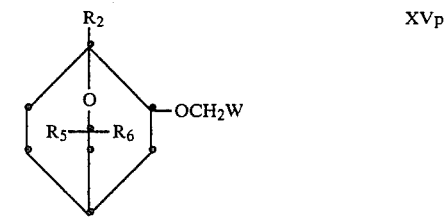

XVp in which $R_2$, $R_5$ and $R_6$ are methyl can be prepared by treating a Diels-Alder adduct of acrolein and isoprene with $Ph_3P=C(CH_3)OCH_3$, hydrolyzing the resulting enol ether, treating the resulting ketone derivative with methyl magnesium bromide, and subjecting the resulting alcohol to epoxidation-cyclization to yield a 2-oxabicyclo[3.2.2]nonan-7-ol, which is treated with $WCH_2X$ in which X is a halogen atom to yield the desired ether, XVp. Alternatively, 4-methyl-3-cyclohexene-1-acetic acid, as obtained by the method of Kugatova-Shemyakina et al., *Chemical Abstracts*, 65:10504c (1966) is treated with methyl Grignard followed by epoxidation-cyclization of the resulting alcohol to yield a 2-oxabicyclo[3.2.2]nonan-7-ol.

(XVI) When m is 0, n is 2 or p is 3, the ring system is a 2-oxabicyclo[3.3.1]nonane, another subclass of the invention. For example, a compound of subclass XVI of formula XVIp below

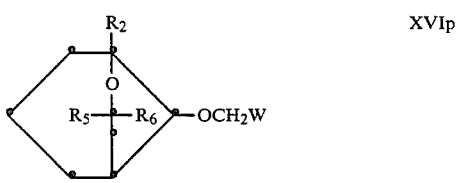

XVIp in which $R_2$, $R_5$ and $R_6$ are methyl in formula 1 can be prepared by treating 3-methyl-3-acetoxycyclohex-1-ene with a malonic ester in the presence of palladium(II), the resulting cyclohexene diester is hydrolyzed, decarboxylated, and treated with methyl Grignard reagent. The resulting cyclohexenylalkanol is epoxidized and cyclized to yield the 2-oxabicyclo[3.3.1]nonan-9-ol, which is treated with $WCH_2X$ in which X is halogen to yield the desired ether XVIp. Alternatively, 3-methyl-2-cyclohexen-1-carboxylic acid is converted to 3-methyl-2-cyclohexen-1-acetic acid by methods analogous to those of the literature and described for compounds of formula XIp, the resulting acid is treated with methyl Grignard, and the resulting alcohol is subjected to epoxidation-cyclization to yield 2-oxabicyclo[3.3.1]nonan-9-ol.

Besides their utility as intermediates to the ethers of formula 1, the oxabicycloalkanols and their corresponding ketones of formulas 1a and 1b below are useful as odor-modifying agents for the manufacture of perfumed products, such as soaps, detergents, household materials and cosmetic preparations.

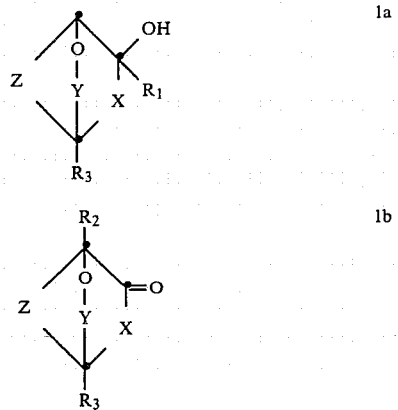

in which $R_1$, $R_2$, $R_3$, X, Y and Z are the same as for the compounds of formula 1.

The ethers of the formula 1 of the invention are useful as antioxidants because they react with ozone, as solvents or dispersing agents for pigments, paints, polymers and synthetic fibers, and plasticizers for vinyl resins.

The compounds of the Invention have been found useful for influencing plant growth and controlling the growth of unwanted plants, being particularly active with respect to grassy weeds and some broadleafed plants. For example, the compounds can change plant morphology; depress the growth of plants, such as broadleafed weeds; inhibit germination; or totally or selectively kill plants depending on the amount used. As herbicides, they appear to be more effective when applied preemergence or pre-plant incorporated (applied to the soil before the seeds have sprouted) than when applied postemergence (applied to the foliage).

At the dosages that effectively control unwanted plants (weeds, such as yellow nutsedge, grasses generally, and velvetleaf), the Compounds of the Invention have shown selectivity to one or more crops such as cotton, soybeans, peanuts, wheat, rice and the like.

Protection of a locus or area from undesirable plants is effected by applying a Compound of the Invention, ordinarily a composition of one of the aforementioned types, to the soil in which the plant is growing or in which the seeds are present or to plant and foliage. The Compounds of the Invention, of course, are applied in amounts sufficient to exert the desired action.

The amounts of the Compounds of the Invention to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from about 0.05 to 10.0 kilograms per hectare of the area will be satisfactory for practicl applications, preferably from about 0.1 to about 5 kilograms per hectare.

Particularly preferred compounds of the invention because of their herbicidal properties are:

($\pm$)-2-exo-(2-fluorobenzyloxy)-1-methyl-4-isopropyl-7-oxabicyclo[2.2.1]heptane, ($\pm$)-2-exo-(2-methylbenzyloxy)-1-methyl-4-isopropyl-7-oxabicyclo[2.2.1]heptane, ($\pm$)-2-exo-(2-fluorobenzyloxy)-4-(1-chloro-1-methylethyl)-1-methyl-7-oxabicyclo[2.2.1]heptane, ($\pm$)-2-exo-(2-methylbenzyloxy)-4-(1-chloro-1-methylethyl)-1-methyl-7-oxabicyclo[2.2.1]heptane, ($-$)-2-exo-(2-fluorobenzyloxy)-1-methyl-4-isopropyl-7-oxabicyclo[2.2.1]heptane, and ($-$)-2-exo-(2-methylbenzyloxy)-1-methyl-4-isopropyl-7-oxabicyclo[2.2.1]heptane.

For application to the locus to be treated, e.g. herbicidal application, the compounds of the invention preferably are formulated with an inert carrier, or a surface-active material, or both.

By "carrier" is meant a solid or a fluid material, which may be inorganic or organic and of synthetic or natural origin, with which the compound of the invention is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as, for example, isopropanol, glycols; ketones such as, for example, acetone, methyl ethyl ketone, methyl isobutyl ketone and cyclohexanone; ethers such as, for example, tetrahydrofuran; aromatic hdyrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, chorobenzene including liquified normally vaporous gaseous compounds. Mixtures of different liquids are often suitable. The surface-active agent may be an emulsifying agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols and alkylphenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions may be formulated as wettable powders, dusts, granules, solutions, emulsifiable concentrates, emulsions, suspension concentrates and aerosols. Wettable powders are usually compounded to contain 25, 50 and 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of toxicant. Granules are usually prepared to have a size between 10 and 100 BS mesh (1.676–0.152 mm), and may be manufactured by agglomeration or impregnation techniques. Generally, granules will contain 0.5–25% by weight toxicant and 0–1% by weight of additives such as stabilizers, slow-release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight toxicant, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate with water, also are suitable. The said emulsions may be of the water-in-oil or of the oil-in-water type, and may have a thick mayonnaise-like consistency.

The compositions may also contain other ingredients, for example, other compounds possessing pesticidal, especially insecticidal, acaricidal, herbicidal or fungicidal properties.

ILLUSTRATIVE EMBODIMENTS

The invention is illustrated by the following embodiments which describe the preparation of typical species of the invention. The embodiments are presented for the purpose of illustration only, and should not be regarded as limiting the invention in any way. The identity of the products, including intermediates, was confirmed by elemental, infrared and nuclear magnetic resonance spectral (NMR) analyses as necessary.

EMBODIMENT 1

($\pm$)-2-exo-Hydroxy-1-methyl-4-isopropyl-7-oxabicyclo[2.2.1]heptane

To a solution of 22.3 g of 85% m-chloroperbenzoic acid in 150 ml of methylene chloride was added over 40 minutes a solution of 15.4 g of ($\pm$)-terpinen-4-ol in 30 ml methylene chloride at a temperature of about 0° C. The reaction mixture was stirred for 20 hours at room temperature, then cooled to 5° C. A solid was filtered and rinsed with cold methylene chloride. The combined filtrates were washed successively with one-eighth saturated potassium carbonate, saturated sodium sulfite, and then water, dried and Claisen distilled to yield 8.9 of product, b.p. 109°–113° C. at 8 mm. Recrystallization of the solidified distillate from pentane gave 5.5 g of the desired product, m.p. 42°–58° C.

EMBODIMENT 2

($\pm$)-2-exo-Hydroxy-1-methyl-4-isopropyl-7-oxabicyclo[2.2.1]heptane

To a solution of 30.8 g of ($\pm$)-terpinen-4-ol and 0.8 g of vanadium(IV) bis(2,4-pentanedionate)oxide in 300 ml of methylene chloride was added 22.0 g of 90% tert-butyl hydroperoxide. The resulting reaction, initially mildly exothermic, was held at reflux for 2 hours, to obtain the epoxide, then 0.8 g of p-toluenesulfonic acid in 10 ml of glyme was added. The resulting reaction mixture was refluxed for 1.5 hours, and cooled, and 0.8 g of anhydrous sodium acetate was added with stirring. After filtration, the filtrate was concentrated and Claisen distilled to give 28.4 g of the desired product, b.p. 80°–95° (2 mm).

EMBODIMENT 3

($\pm$)-2-exo-(Benzyloxy)-1-methyl-4-isopropyl-7-oxabicyclo[2.2.1]heptane

To a solution of 1.7 g of ($\pm$)-2-exo-hydroxy-1-methyl-4-isopropyl-7-oxabicyclo[2.2.1]heptane in 15 ml of dimethylformamide was added at room temperature 0.5 g of 50% sodium hydride. The resulting mixture was stirred overnight at room temperature, heated for one-half hour at 50° C., cooled to room temperature, and after 1.5 g of benzyl chloride was added in one portion, stirred at room temperature for three hours, heated to 50° C. for one hour, cooled, poured into 50 ml of water, and extracted with one 50 ml and two 25 ml portions of methylene chloride. The combined methylene chloride extracts was washed with 100 ml of water, dried and evaporated to give an orange oil. Claisen distillation yielded 1.5 g of the desired product, b.p. 103° C. at 0.08 mm.

EMBODIMENT 4

4-Ethyl-3-cyclohexen-1-one

To a stirred refluxing mixture of 600 ml. of dry ether and 1600 ml of liquid ammonia was added 136 g of p-ethylanisole. After 15 minutes, there was added portionwise, at −35° to −32° C., 26.4 g of lithium ribbon over 0.5–1 hour. After an additional 15 minutes, 193 g of dry ethanol was added dropwise at −35° to −32° C. Stirring was continued until the blue color disappeared, and the ammonia was allowed to evaporate on standing overnight. The residue was poured into 1 l of ice water and extracted twice with ether. The combined ether extracts concentrated to a volume of about 300 ml was stirred with 250 ml of water containing 46 g of oxalic acid overnight at ambient temperature. This mixture was diluted with 1 liter of water and extracted twice with ether. The combined ether extracts was washed with 5% sodium bicarbonate and then with water. After drying, the ether solution was vacuum-concentrated to a residue of 104.4 g of desired product; it was 94% pure by GLC analysis and used without distillation.

EMBODIMENT 5

1,4-Diethyl-3-cyclohexen-1-ol

To a stirred solution of 35 ml of 3.2M ethereal ethyl magnesium bromide (Aldrich) in 75 ml of dry ether was added dropwise at gentle reflux a solution of 10.0 g of 4-ethyl-3-cyclohexen-1-one in 25 ml of ether. After one hour longer at reflux, the mixture was cooled and treated dropwise with 80 ml of water. The aqueous layer was extracted with ether and the combined ether layers was dried, concentrated, and Claisen-distilled to give 7.3 g of the desired product, b.p. 82°–86° C. (5 mm.).

EMBODIMENT 6

(±)-2-exo-Hydroxy-1,4-diethyl-7-oxabicyclo[2.2.1]heptane

To a stirred solution of 15.4 g of 1,4-diethyl-3-cyclohexen-1-ol and 0.4 g of vanadium(IV) bis(2,4-pentanedionate)oxide in 125 ml of methylene chloride was added dropwise at gentle reflux 11.0 g of 90% tert-butyl hydroperoxide. After an additional 2 hrs. reflux, the mixture was cooled slightly, treated with 7.2 ml of glyme containing 0.58 g of p-toluenesulfonic acid, and refluxed for 2 hrs. longer. The cooled mixture was stirred for 0.5 hr. with 1.0 g of anhydrous sodium acetate and filtered through filter aid. The filtrate was concentrated and Claisen-distilled to give 14.4 g of product, b.p. 65°–78° C. (1 mm).

EMBODIMENT 7

(±)-2-exo-Benzyloxy-1,4-diethyl-7-oxabicyclo[2.2.1]heptane

A stirred mixture of 3.8 g of crude (±)-2-exo-hydroxy-1,4-diethyl-7-oxabicyclo[2.2.1]heptane, 50 ml. of N,N-dimethylacetamide and 1.0 g of sodium hydride (washed with n-hexane) was warmed slowly to 80° C. to complete hydrogen evolution. The cooled mixture was treated with 3.0 g of benzyl chloride, again warmed to 80° C., and after ½ hour, poured into ice water, and extracted twice with methylene chloride. The combined organic extracts was washed, dried, concentrated and Claisen-distilled to give 2.6 g of the desired product, b.p. 105°–110° (0.1 mm).

EMBODIMENTS

By procedures similar to those in Embodiments 1–7, the following compounds of the invention in Table I below were prepared.

TABLE I

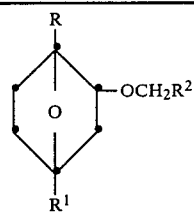

| Embodiment | R | R$^1$ | R$^2$ | Rotation and Configuration | Boiling Point °C. (mm) |
|---|---|---|---|---|---|
| 8 | CH$_3$ | i-C$_3$H$_7$ | phenyl | (−) exo | 100–110 (0.05) |
| 9 | CH$_3$ | i-C$_3$H$_7$ | 2-methylphenyl | (±) exo | 110–113 (0.1) |
| 10 | CH$_3$ | i-C$_3$H$_7$ | 2-methylphenyl | (−) exo | 114–116 (0.1) |
| 11 | CH$_3$ | i-C$_3$H$_7$ | 2-pyridinyl | (±) exo | 108–112 (0.05) |
| 12 | CH$_3$ | i-C$_3$H$_7$ | 2-pyridinyl | (−) exo | 114 (0.1) |
| 13 | CH$_3$ | i-C$_3$H$_7$ | 2-chlorophenyl | (±) exo | 114–115 (0.05) |
| 14 | CH$_3$ | i-C$_3$H$_7$ | 2-fluorophenyl | (±) exo | 105–112 (0.05) |
| 15 | CH$_3$ | i-C$_3$H$_7$ | 2-fluorophenyl | (−) exo | 103–105 (0.1) |
| 16 | CH$_3$ | i-C$_3$H$_7$ | 2,6-dichlorophenyl | (±) exo | 12–127 (0.05) |
| 17 | C$_2$H$_5$ | CH$_3$ | phenyl | (±) exo | 95–98 (0.05) |
| 18 | C$_2$H$_5$ | C$_2$H$_5$ | 2-methylphenyl | (±) exo | 110–112 (0.1) |
| 19 | C$_2$H$_5$ | C$_2$H$_5$ | 2-fluorophenyl | (±) exo | 101–103 (0.1) |
| 20 | C$_2$H$_5$ | C$_2$H$_5$ | 2-chlorophenyl | (±) exo | 118–120 (0.1) |
| 21 | C$_2$H$_5$ | C$_2$H$_5$ | 2-pyridinyl | (±) exo | 110–111 (0.1) |
| 22 | CH$_3$ | C$_2$H$_5$ | phenyl | (±) exo | 98–99 (0.05) |
| 23 | CH$_3$ | C$_2$H$_5$ | 2-methylphenyl | (±) exo | 115 (0.3) |
| 24 | C$_2$H$_5$ | CH$_3$ | 2-methylphenyl | (±) exo | 110–112 (0.15) |
| 25 | CH$_3$ | C$_2$H$_5$ | 2-chlorophenyl | (±) exo | 113–114 (0.1) |
| 26 | C$_2$H$_5$ | CH$_3$ | 2-chlorophenyl | (±) exo | 112–115 (0.05) |
| 27 | CH$_3$ | C$_2$H$_5$ | 2,6-dichlorophenyl | (±) exo | 128–130 (0.1) |
| 28 | C$_2$H$_5$ | CH$_3$ | 2,6-dichlorophenyl | (±) exo | 130–132 (0.05) |
| 29 | CH$_3$ | i-C$_3$H$_7$ | 2-chlorophenyl | (−) exo | 112 (0.05) |
| 30 | CH$_3$ | CH$_3$ | phenyl | (±) exo | 93 (0.05) |
| 31 | CH$_3$ | CH$_3$ | 1-methylphenyl | (±) exo | 102–104 (0.05) |
| 32 | C$_2$H$_5$ | C$_2$H$_5$ | 2,6-dichlorophenyl | (±) exo | 134–138 (0.2) |
| 33 | CH$_3$ | i-C$_3$H$_7$ | 2,6-dichlorophenyl | (±) exo | 145–147 (<1) |
| 34 | CH$_3$ | CH$_3$ | 2,6-dichlorophenyl | (±) exo | 119–120 (0.05) |
| 35 | CH$_3$ | i-C$_3$H$_7$ | phenyl | (+) exo | 107 (0.2) |
| 36 | CH$_3$ | i-C$_3$H$_7$ | 2-fluorophenyl | (±) endo | 105–108 (0.2) |
| 37 | CH$_3$ | i-C$_3$H$_7$ | 2-methylphenyl | (+) exo | (109–112 0.1 |
| 38 | CH$_3$ | i-C$_3$H$_7$ | 2-pyridinyl | (+) exo | 118–120 (0.1) |

TABLE I-continued

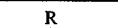

| Embodiment | R | R¹ | R² | Rotation and Configuration | Boiling Point °C. (mm) |
|---|---|---|---|---|---|
| 39 | CH₃ | i-C₃H₇ | 2-fluorophenyl | (+) exo | 118 (<1) |
| 40 | CH₃ | i-C₃H₇ | 2,5-dimethylphenyl | (+) exo | 120-125 (0.1) |
| 41 | CH₃ | n-C₄H₉ | phenyl | (±) exo | 115-116 (0.1) |
| 42 | n-C₃H₇ | CH₃ | phenyl | (±) exo | 107-110 (0.2) |
| 43 | CH₃ | phenyl | phenyl | (±) exo | 155 (0.15) |
| 44 | CH₃ | i-C₃H₇ | 2-methylphenyl | (±) endo* | 115-118 (0.2) |

*See Embodiments 118-119 for preparation of (±) endo alcohol.

EMBODIMENT 45

4-Methyl-1-(1-methyl-1-(phenylthio)ethyl)-3-cyclohexen-1-ol

To a stirred solution of 76 g of 2,2,6-trimethyl-1-oxaspiro(2.5)oct-5-ene in 300 ml of n-pentanol were added 2.0 g of 60% sodium hydride and 60 g of thiophenol. After 18 hours reflux, the mixture was vacuum concentrated at 90°-95° C. The residue was dissolved in methylene chloride and washed twice with 2N sodium hydroxide. The dried solution was Claisen-distilled to give 106 g of crude product, b.p. 120°-125° C. (0.1 mm). Recrystallization from 250 ml of hexane gave 69.1 g of the desired product, m.p. 73°-74° C.

EMBODIMENT 46

(±)-2-exo-Hydroxy-1-methyl-4-(1-methyl-1-(phenylsulfonyl)ethyl)-7-oxabicyclo[2.2.1]heptane To a stirred solution of 13.1 g of (±)-4-methyl-1-(1-methyl-1-(phenylthio)ethyl)-3-cyclohexen-1-ol and 0.27 g of vanadium(IV) bis(2,4-pentanedionate)oxide in 130 ml of methylene chloride was added dropwise at reflux 20.0 g of 90% tert-butyl hydroperoxide in 10 minutes. The mixture was refluxed for one hour longer, and after cooling, washed, dried and vacuum-concentrated at 50°-55° C. To the resulting residue of about 18 g., 5 ml of glyme containing 0.4 g of p-toluenesulfonic acid was added. The mixture was stirred overnight at 5°-25° C. Since an insoluble oil had formed, 100 ml of chloroform was added and the ether and pentane were removed by vacuum-concentration. The residual chloroform solution was washed with potassium carbonate, dried and concentrated to a residue of 14.9 g. This residue was purified by dry column chromatography using a 30:220:500 mixture of tetrahydrofuran:ethyl acetate:hexane as eluent. This column was divided into 12 equal parts; fraction 10 gave 5 g of product. Recrystallization of fraction 10 from diethyl ether gave 3.0 g of the desired product, m.p. 108°-110° C.

EMBODIMENT 47

(±)-2-exo-Benzyloxy-1-methyl-4-(1-methyl-1-phenylsulfonyl)ethyl)-7-oxabicyclo[2.2.1]heptane Following procedures similar to those described in Embodiments 3 and 7, (±)-2-exo-hydroxy-1-methyl-4-(1-methyl-1-phenylsulfonyl)ethyl)-7-oxabicyclo[2.2.1-]heptane was treated with benzyl chloride to yield the desired product as a solid, m.p. 94°-96° C.

EMBODIMENT 48

(±)-4-Methyl-1-(1-methyl-1-(methylthio)ethyl)-3-cyclohexen-1-ol

To a stirred solution of 15.2 g of 2,2,6-trimethyl-1-oxaspiro(2.5)oct-5-ene in 100 ml of N,N-dimethylacetamide was added 4.4 g of 60% sodium hydride. The mixture was cooled to 5°-10° C. and saturated with methyl mercaptan. Stirring was continued while heating the reaction mixture to 100° C. over a two and one-half hour period. After an additional hour at 100° C., the reaction mixture was poured into water and extracted twice with p-pentane. The combined extracts was washed with water, dried and Claisen-distilled to give 15.8 g of the desired product, b.p. 83°-85° C. (0.2 mm).

EMBODIMENT 49

(±)-2-exo-(Benzyloxy)-1-methyl-4-(1-methyl-1-(methylsulfonyl)ethyl)-7-oxabicyclo[2.2.1]heptane Following procedures similar to those described in Embodiment 46, (±)-4-methyl-(1-methyl-1-(methylthio)ethyl)-3-cyclohexen-1-ol was treated with vanadium-(IV) bis(2,4-pentanedionate)oxide and tert-butyl hydroperoxide followed by p-toluenesulfonic acid to obtain (±)-2-exo-hydroxy-1-methyl-4-(1-methyl-1-(methylsulfonyl)ethyl)-7-oxabicyclo[2.2.1]heptane. This intermediate product was treated with benzyl chloride by procedures similar to those described in Embodiments 3 and 7 to yield the desired product as an amber oil.

EMBODIMENT 50

(±)-4-Methyl-1-(1-chloro-1-methylethyl)-3-cyclohexen-1-ol

To a stirred solution of 15.2 g of 2,2,6-trimethyl-1-oxaspiro(2.5)oct-5-ene in 200 ml of diethyl ether held at −10° C. was added dropwise 32 ml of 3.8N ethereal hydrogen chloride. After one hour at 0°-5° C., the mixture was washed with three 50 ml portions of water, dried and distilled to give 14.5 g of the desired product, b.p. 70°-75° C. (0.4 mm).

EMBODIMENT 51

(±)-2-exo-(Benzyloxy)-4-(1-chloro-1-methylethyl)-1-methyl-7-oxabicyclo[2.2.1]heptane Following procedures similar to those described in Embodiments 6 and 46, (±)-4-methyl-1-(1-chloro-1-methylethyl))-3-cyclohexen-1-ol was treated with vanadium(IV) bis(2,4-pentanedionate)oxide and tert-butyl hydroperoxide followed by p-toluenesulfonic acid to obtain (±)-2-exo-hydroxy-4-(1-chloro-1-methylethyl)-1-methyl-7-oxabicyclo[2.2.1]heptane. This intermediate product was treated with benzyl chloride by procedures similar to those described in Embodiments 3 and 7 to yield the desired product, b.p. 120°-122° C. (0.15 mm).

EMBODIMENT 52

(±)-1-Hydroxy-alpha,alpha,4-trimethyl-3-cyclohexane-1-acetonitrile

To a stirred mixture of 7.0 g of zinc dust (washed twice with 10% hydrochloric acid, then successively with water, acetone and diethyl ether, and dried overnight at 60° C. in a vacuum oven), 0.45 g of mercuric chloride and 4 ml of tetrahydrofuran was added dropwise over 45 minutes at 20°–25° C. a mixture of 9.7 g of 4-methyl-3-cyclohexen-1-one, 13.7 g of alpha-bromoisobutyronitrile and 25 ml of tetrahydrofuran. After an additional hour at 25° C., the reaction mixture was cooled to 5°–10° C. and treated dropwise with 50 ml of cold 10% sulfuric acid. To this was added 100 ml of methylene chloride, and the mixture was filtered. The filtrate was diluted with 100 ml of water and extracted twice with 100 ml portions of methylene chloride. The combined methylene chloride extracts was washed with bicarbonate, dried and Claisen-distilled to give 11.3 g of the desired product, b.p. 92°–102° C. (0.25 mm).

EMBODIMENT 53

(±)-2-exo-(Benzyloxy)-4-(1-cyano-1-methylethyl)-1-methyl-7-oxabicyclo[2.2.1]heptane By procedures similar to those described in Embodiments 6 and 46, (±)-1-hydroxy-alpha,alpha, 4-trimethyl-3-cyclohexene-1-acetonitrile was treated with vanadium(IV) bis(2,4-pentanedionate)oxide and tert-butyl hydroperoxide followed by p-toluenesulfonic acid to obtain (±)-2-exo-hydroxy-1-methyl-4-(1-cyano-1-methylethyl)-7-oxabicyclo[2.2.1]heptane. This intermediate product was treated with benzyl chloride by procedures similar to those described in Embodiments 3 and 7 to yield the desired product, b.p. 139°–140° C. (0.1 mm).

EMBODIMENT 54

(±)-2-exo-(2,6-Dichlorobenzyloxy)-4-(1-cyano-1-methylethyl)-1-methyl-7-oxabicyclo[2.2.1]heptane By procedures similar to those described in Embodiments 6 and 46, 1-hydroxy-alpha,alpha,4-trimethyl-3-cyclohexene-1-acetonitrile was treated with vanadium(IV) bis(2,4-pentanedionate) oxide and tert-butyl hydroperoxide followed by p-toluenesulfonic acid to obtain (±)-2-exo-hydroxy-4-(1-cyano-1-methylethyl)-1-methyl-7-oxabicyclo[2.2.1]heptane. This intermediate product was treated with 2,6-dichlorobenzyl chloride by procedures similar to those described in Embodiments 3 and 7 to yield the desired product, b.p. 162°–165° C. (0.15 mm).

EMBODIMENT 55

(±)-1-(1-hydroxy-1-methylethyl)-4-methyl-3-cyclohexen-1-ol

A mixture of 26.0 g of 2,2,6-trimethyl-1-oxaspiro(2.5)oct-5-ene and 250 ml of 1% sulfuric acid was stirred magnetically for 20 hours, then extracted with four 100 ml portions of methylene chloride. The combined methylene chloride extracts was washed, dried, concentrated and Claisen-distilled to give 22.4 g of the desired product, b.p. 78°–81° C. (0.15 mm).

EMBODIMENT 56

(±)-2-exo-(Benzyloxy)-4-(1-hydroxy-1-methylethyl)-1-methyl-7-oxabicyclo[2.2.1]heptane By procedures similar to those described in Embodiment 6, (±)-1-(1-hydroxy-1-methylethyl)-4-methyl-3-cyclohexen-1-ol was treated with vanadium(IV) bis(2,4-pentanedionate)oxide and tert-butyl hydroperoxide followed by p-toluenesulfonic acid to obtain (±)-2-exo-hydroxy-4-(1-hydroxy-1-methylethyl)-1-methyl-7-oxabicyclo[2.2.1]heptane. This intermediate product was treated with benzyl chloride by procedures similar to those described in Embodiments 3 and 7 to yield the desired product, b.p. 114°–115° C. (0.1 mm).

EMBODIMENT 57

(±)-4-Methyl-1-(1-methoxy-1-methylethyl)-3-cyclohexen-1-ol

To a stirred solution of 0.8 g of p-toluenesulfonic acid in 125 ml of methanol held at 3°–5° C. was added dropwise over 0.5 hour a solution of 15.2 g of 2,2,6-trimethyl-1-oxaspiro(2.5)oct-5-ene in 25 ml of methanol. After an additional 2 hours at 5° C. and 2 hours at 5°–20° C., the mixture was treated with 2 ml of 15% sodium hydroxide and concentrated at a water pump at below 60° C. The residue was dissolved in methylene chloride, washed, dried and Claisen-distilled to give 15.6 g of the desired product, b.p. 70° C. (0.2 mm).

EMBODIMENT 58

(±)-2-exo-(Benzyloxy)-4-(1-methoxy-1-methylethyl)-1-methyl-7-oxabicyclo[2.2.1]heptane By procedures similar to those described in Embodiment 6, 1-(1-methoxy-1-methylethyl)-4-methyl-3-cyclohexen-1-ol was treated with vanadium(IV) bis(2,4-pentandionate)oxide and tert-butyl hydroperoxide followed by p-toluenesulfonic acid to obtain (±)-2-exo-hydroxy-4-(1-methoxy-1-methylethyl)-1-methyl-7-oxabicyclo[2.2.1]heptane. This intermediate was treated with benzyl chloride by procedures similar to those described in Embodiments 3 and 7 to yield the desired product, b.p. 110°–115° C. (0.1 mm).

EMBODIMENT 59

(±)-2-exo-(Benzyloxy)-4-(1-ethoxy-1-methylethyl)-1-methyl-7-oxabicyclo[2.2.1]heptane By procedures similar to those described in Embodiments 57 and 58, 2,2,6-trimethyl-1-oxaspiro(2.5)oct-5-ene was treated with ethanol in the presence of p-toluenesulfonic acid to obtain 1-(1-ethoxy-1-methylethyl)-4-methyl-3-cyclohexen-1-ol. This alcohol was treated with vanadium(IV) bis(2,4-pentanedionate)oxide and tert-butyl hydroperoxide followed by p-toluenesulfonic acid to obtain (±)-2-exo-hydroxy-4-(1-ethoxy-1-methylethyl)-1-methyl-7-oxabicyclo[2.2.1]heptane. This intermediate was treated with benzyl chloride to yield the desired product, b.p. 120°–125° C. (0.2 mm).

EMBODIMENT 60

(±)-2-exo-(Benzyloxy)-4-(1-isopropoxy-1-methylethyl)-1-methyl-7-oxabicyclo[2.2.1]heptane By procedures similar to those described in Embodiments 57 and 58, 2,2,6-trimethyl-1-oxaspiro(2.5)oct-5-ene was treated with isopropyl alcohol in the presence of p-toluenesulfonic acid to obtain 1-(1-isopropoxy-1-methylethyl)-4-methyl-3-cyclohexen-1-ol. This alcohol was treated with vanadium(IV) bis(2,4-pentanedionate)oxide and tert-butyl hydroperoxide followed by p-toluenesulfonic acid to obtain (±)-2-exo-hydroxy-4-(1-isopropoxy-1-methylethyl)-1-methyl-7-oxabicyclo[2.2.1]heptane. This intermediate was treated with benzyl chloride to yield the desired product, b.p. 120°–130° C. (0.2 mm).

EMBODIMENT 61

(±)-2-exo-(Propargyloxy)-4-isopropyl-1-methyl-7-oxabicyclo[2.2.1]heptane

By procedures similar to those described in Embodiment 3, (±)-2-exo-hydroxy-4-isopropyl-1-methyl-7-oxabicyclo[2.2.1]heptane was treated with propargyl chloride to yield the desired product, b.p. 100°–105° C. (4 mm).

EMBODIMENT 62

(±)-2-exo-(4-Fluorobenzyloxy)-4-isopropyl-1-methyl-7-oxabicyclo[2.2.1]heptane

By procedures similar to those described in Embodiment 3, (±)-2-exo-hydroxy-4-isopropyl-1-methyl-7-oxabicyclo[2.2.1]heptane was treated with 4-fluorobenzyl chloride to yield the desired product, b.p. 102°–105° C. (0.1 mm).

EMBODIMENT 63

(±)-2-exo-(2-Chlorobenzyloxy)-4-(1-chloro-1-methylethyl)-1-methyl-7-oxabicyclo[2.2.1]heptane By procedures similar to those described in Embodiments 50 and 51, (±)-2-exo-hydroxy-4-(1-chloro-1-methylethyl)-1-methyl-7-oxabicyclo[2.2.1]heptane was treated with 2-chlorobenzyl chloride to yield the desired product as an oil.

EMBODIMENT 64

(±)-2-exo-(Benzyloxy)-1-methyl-4-benzyl-7-oxabicyclo[2.2.1]heptane

By procedures similar to those described in Embodiments 1–7, (±)-2-exo-hydroxy-1-methyl-4-benzyl-7-oxabicyclo[2.2.1]heptane was treated with benzyl chloride to yield the desired product, b.p. 140°–150° C. (0.1 mm).

EMBODIMENT 65

1,4-Dimethyl-5-nitro-7-oxabicyclo[2.2.1]hept-2-ene

A 25.6 g portion of nitroethylene was dissolved in ethyl ether and dried ($Na_2SO_4$), and after filtering and rinsing with ether, the filtrate was made up to 250 ml of solution. This nitroethylene-ether solution was added to a stirred, cooled solution of 42.2 g of 2,5-dimethylfuran in 150 ml of ethyl ether in the presence of 0.4 g of hydroquinone as polymerization inhibitor. The reaction mixture was refrigerated for several days, stirred at room temperature for 24 hours, treated with charcoal, filtered through celite and stripped to yield 53.3 g of the desired product as an amber oil.

EMBODIMENT 66

1,4-Dimethyl-2-nitro-7-oxabicyclo[2.2.1]heptane 5.5 g of 1,4-dimethyl-5-nitro-7-oxabicyclo[2.2.1]hept-2-ene was placed in a ½ liter Parr bomb with 50 ml of ethanol and 10% palladium on powdered charcoal catalyst. The bomb was charged with hydrogen gas under 50 lb pressure. After using 3 lb of hydrogen gas, the reaction mixture was removed from the bomb, filtered to remove the catalyst, and stripped. The residue taken up in ether, was washed with water, dried ($MgSO_4$), filtered and stripped to yield 4.8 g of the desired product as a brownish oil.

EMBODIMENT 67

1,4-Dimethyl-7-oxabicyclo[2.2.1]heptan-2-one

To 900 ml of 0.1N potassium hydroxide was added with stirring 5.0 g of 1,4-dimethyl-2-nitro-7-oxabicyclo[2.2.1]heptane. To this mixture was added 125 ml of 2M $MgSO_4$ solution and sufficient water to bring the total volume to 2.5 liters, followed dropwise at 0°–5° C. by a solution of 4.5 g of potassium permanganate in 125 ml of water. After stirring for 1 hour, the resulting mixture was filtered through celite. The filtrate was decolorized with sodium bisulfite and extracted with methylene chloride. The extract was dried ($MgSO_4$), filtered and stripped to give 3.3 g of a pale yellow oil. This procedure was repeated to yield 3.2 g of a pale yellow oil. These products were combined and distilled to yield 5.8 g of the desired product as a colorless oil.

EMBODIMENT 68

(±)-2-endo-Hydroxy-1,4-dimethyl-7-oxabicyclo[2.2.1]heptane

To a solution of 2.3 g of 1,4-dimethyl-7-oxabicyclo[2.2.1]heptan-2-one in 20 ml of dry tetrahydrofuran was added dropwise 16 ml of boron hydride in tetrahydrofuran under nitrogen atmosphere and at 0°–5° C. The resulting mixture was stirred at 0° C. for 10 minutes, quenched in water, extracted with methylene chloride, dried ($MgSO_4$), and stripped to give 2.0 g of pale yellow oil. The reaction was repeated to yield 1.0 g of pale yellow oil. The combined products was distilled at 102°–105° C. (4 mm) to give 1.6 g of the desired product as a colorless oil.

EMBODIMENT 69

(±)-2-endo-Benzyloxy-1,4-dimethyl-7-oxabicyclo[2.2.1]heptane

To a mixture of 0.6 g of sodium hydride in 10 ml of dimethylformamide under nitrogen was added 1.6 g of (±)-2-endo-hydroxy-1,4-dimethyl-7-oxabicyclo[2.2.1]heptane in 5 ml of dimethylformamide. After the evolution of hydrogen ceased, 2.1 g of benzyl chloride in 5 ml of dimethylformamide was added dropwise. The reaction mixture was stirred overnight, quenched in water, and extracted with pentane. The extract was washed with water, dried ($MgSO_4$), and stripped to yield 2.9 g of pale yellow oil (A). Chromatographic separation of this oil on silica gel using ethyl acetate-methylene chloride (1:6) eluent yielded 0.8 g of yellow oil (B) and 0.3 g of yellow oil (C). Fraction (B) was rechromatographed to yield 0.5 g of yellow oil (D) and 0.1 g of yellow oil (E). Fraction (D) was further chromatographed with pentane-methylene chloride (3:1) as eluent to yield two principal fractions: 0.2 g of yellow oil (E) and 0.2 g of yellow oil (F). The fractions (E) and (F) were confirmed to be the desired product.

EMBODIMENT 70

(±)-2-exo-(3-Fluorobenzyloxy)-4-isopropyl-1-methyl-7-oxabicyclo[2.2.1]heptane

By procedures similar to those described in Embodiment 3, (±)-2-exo-hydroxy-4-isopropyl-1-methyl-7-oxabicyclo[2.2.1]heptane was treated with 3-fluorobenzyl chloride to yield the desired product, b.p. 103°–104° C. (0.1 mm).

EMBODIMENT 71

(±)-2-exo-(2-Furanylmethoxy)-4-isopropyl-1-methyl-7-oxabicyclo[2.2.1]heptane

By procedures similar to those described in Embodiment 3, (±)-2-exo-hydroxy-4-isopropyl-1-methyl-7-oxabicyclo[2.2.1]heptane was treated with 2-furanylmethyl chloride to yield the desired product, b.p. 94°–95° C. (0.2 mm).

EMBODIMENT 72

(±)-2-exo-(2-Fluorobenzyloxy)-4-(1-chloro-1-methylethyl)-1-methyl-7-oxabicyclo[2.2.1]heptane By procedures similar to Embodiments 3, 7 and 51, (±)-2-exo-hydroxy-4-(1-chloro-1-methylethyl)-1-methyl-7-oxabicyclo[2.2.1]heptane was treated with 2-fluorobenzyl chloride to yield the desired product, b.p. 133°–134° C. (0.2 mm).

EMBODIMENT 73

(±)-2-exo-(2-Methylbenzyloxy)-4-(1-chloro-1-methylethyl)-1-methyl-7-oxabicyclo[2.2.1]heptane By procedures similar to Embodiments 3, 7 and 51, (±)-2-exo-hydroxy-4-(1-chloro-1-methylethyl)-1-methyl-7-oxabicyclo[2.2.1]heptane was treated with 2-methylbenzyl chloride to yield the desired product, b.p. 128°–130° C. (0.1 mm).

EMBODIMENT 74

(±)-2-exo-(2-Fluorobenzyloxy)-4-ethyl-1-methyl-7-oxabicyclo[2.2.1]heptane

By procedures similar to Embodiments 4–7, (±)-2-exo-hydroxy-4-ethyl-1-methyl-7-oxabicyclo[2.2.1]heptane was prepared from 4-ethyl-3-cyclohexen-1-one and then treated with 2-fluorobenzyl chloride to yield the desired product, b.p. 95°–97° C., (0.1 mm).

EMBODIMENT 75 alpha,alpha-Diethyl-4-methyl-3-cyclohexene-1-methanol

To 9.4 g of magnesium stirred in 350 ml of diethyl ether was added 60.4 g of iodoethane over 30 minutes to produce a mildly refluxing reaction mixture. The reaction mixture was refluxed for an additional hour, and then 23 g of the methyl ester of 4-methyl-3-cyclohexene-1-carboxylic acid in 20 ml of diethyl ether was added dropwise while maintaining gentle reflux. The reaction mixture was refluxed for an additional ½ hour, quenched with water, and extracted with diethyl ether; the ether extract was washed with saturated NaCl solution, dried (MgSO₄), and stripped to yield an oil, which upon distillation gave 23.2 g of product, b.p. 90° C. (1 mm).

EMBODIMENT 76

1-Methyl-3,3-diethyl-2-oxabicyclo[2.2.1]octan-6-exo-ol

To a stirred solution of 102 g of alpha,alpha-diethyl-4-methyl-3-cyclohexene-1-methanol in 750 ml methylene chloride was added 125 g of 85% m-chloroperbenzoic acid portionwise over 1½ hours at 20°–23° C. The reaction mixture was stirred for an additional 1½ hours at 20° C., and washed successively with 40 ml aqueous potassium carbonate solution, 300 ml of 2N sodium hydroxide solution, and saturated sodium chloride solution. The organic phase was dried (MgSO₄) and stripped to yield 111 g of crude product.

EMBODIMENT 77

1-Methyl-3,3-diethyl-2-oxabicyclo[2.2.2]octan-6-one

To a stirred solution of 14.9 g of oxalyl chloride in 260 ml of methylene chloride was added a solution of dimethyl sulfoxide in 53 ml of methylene chloride dropwise over 15 minutes at −60° C. The reaction mixture was stirred 10 minutes at −60° C., and a solution of 21.1 g of 1-methyl-3,3-diethyl-2-oxabicyclo[2.2.2]octan-6-exo-ol in 106 ml of methylene chloride was added dropwise over 5 minutes at −60° C. The reaction mixture was stirred for 15 minutes and 53.8 g of triethylamine was added dropwise at −60° C. The resulting mixture was allowed to warm to room temperature, and then 320 ml of water was added. The resulting methylene chloride phase was separated, and washed successively with dilute hydrochloric acid, saturated sodium bicarbonate solution, and saturated sodium chloride solution. The organic phase was dried with MgSO₄ and stripped to yield 22 g of an oil. Distillation of the oil gave 16.3 g of product, b.p. 68°–75° C. (0.05–0.1 mm).

EMBODIMENT 78

1-Methyl-3,3-diethyl-2-oxabicyclo[2.2.2]octan-6-endo-ol

To a stirred solution of 21.3 g of the ketone of Embodiment 77 in a mixture of 85 ml 1,2-dimethoxyethane and 85 ml of tert-butanol at 20° C. was added portionwise over 15 minutes 4.1 g of sodium borohydride. The reaction mixture was maintained at a temperature of 20°–24° C. with a water bath during the addition, stirred at 20° C. for 2 hours, held in a refrigerator for two days, and poured into 150 ml of water. The organic phase was stripped of most of the solvent, and extracted with methylene chloride. The extract was washed with saturated sodium chloride solution, dried over MgSO₄, and stripped to give 21.9 g of crude product, mp 73°–78° C. Recrystallization from pentane gave 17.6 g of product, m.p. 82°–84° C.

EMBODIMENT 79

1-Methyl-3,3-diethyl-6-endo-(benzyloxy)-2-oxabicyclo[2.2.2]octane

A solution of 3.5 g of crude 1-methyl-3,3-diethyl-2-oxabicyclo-[2.2.2]octan-6-endo-ol in 25 ml of tetrahydrofuran was added dropwise to a slurry of 1.2 g of 47% sodium hydride (washed with pentane) at 20°–40° C., resulting in slow evolution of gas. The reaction mixture was heated at reflux for 2 hours, at which time gas evolution appeared to have ceased, then cooled to room temperature, and 0.7 g of tetrabutylammonium iodide was added followed by 3.9 g of benzyl bromide in 30 ml of tetrahydrofuran. The resulting mixture was stirred for 3 days at room temperature, quenched in water, and extracted with ether. The ether phase was washed with water and saturated sodium chloride solution, dried with MgSO₄, and stripped to give 5.5 g of oil. After distilling most of the low boiling materials, the remaining product was chromatographed on a silica gel column and eluted with methylene chloride-pentane (40–60%) to yield three fractions: 0.3 g, 1,2-diphenylethene, 1.1 g, primarily the desired endo-isomer-rich product, and 1.2 g, primarily the exo isomer of the desired product. Rechromatography of the second fraction yielded 0.7 g of pure endo form of the desired product.

EMBODIMENT 80

1-(4-Methyl-3-cyclohexen-1-yl)cyclopentan-1-ol

To a stirred suspension of 46.8 g of magnesium in 250 ml of tetrahydrofuran was added 182 g of 1,4-dibromobutane in 700 ml of dry tetrahydrofuran over 1 hour. The gently refluxing reaction mixture was maintained at reflux for 2 more hours and then cooled to room temperature. A solution of 100 g of the methyl ester of 4-methyl-3-cyclohexene-1-carboxylic acid in 20 ml of dry tetrahydrofuran was added at 20°-30° C. with cooling by an ice bath. The reaction mixture was stirred at room temperature for 2 days, and the excess Grignard reagent was decomposed by careful addition of dilute sulfuric acid. Most of the tetrahydrofuran was evaporated, and the reaction product was extracted with ether. The ether phase was washed successively with water and saturated NaCl solution, dried with $MgSO_4$, and stripped to give 120 g of crude product as an oil. Multiple redistillation of the oil gave 32 g of product b.p. 90°-92° C. (0.5 mm).

EMBODIMENT 81

1-Methyl-3,3-tetramethylene-2-oxabicyclo[2.2.2]octan-6-exo-ol

To 32 g of 1-(4-methyl-3-cyclohexen-1-yl)cyclopentan-1-ol in 40 ml of methylene chloride was added portionwise 39 g of 85% m-chloroperbenzoic acid at 20°-24° C., maintained by occasional ice bath cooling. The reaction mixture was then stirred at room temperature overnight. After addition of 1 g of p-toluenesulfonic acid, the reaction mixture was refluxed for 2 hours, cooled to room temperature, washed successively with 200 ml of aqueous potassium carbonate, 200 ml of 2N sodium hydroxide solution, and saturated sodium chloride solution, dried with $MgSO_4$, and stripped to yield 31 g of product as an oil.

EMBODIMENT 82

1-Methyl-3,3-tetramethylene-2-oxabicyclo[2.2.2]octan-6-one 22.1 g of oxalyl chloride was stirred in 375 ml of methylene chloride, and 29.7 g of dimethyl sulfoxide in 75 ml of methylene chloride was added over five minutes while maintaining the temperature at −60° C. The mixture was stirred for 10 minutes and 31 g of the product of Embodiment 81 above, in 160 ml of methylene chloride was added over five minutes while maintaining the temperature at −60° C. The reaction mixture was stirred for 15 minutes and 80 g of triethylamine was added over ten minutes at −60° C. The reaction mixture was allowed to warm to room temperature, and then 475 ml of water was added. The resulting methylene chloride phase was separated, and washed successively with dilute hydrochloric acid, saturated sodium bicarbonate solution, and saturated sodium chloride solution. The organic phase was dried with $MgSO_4$, and stripped to yield 31 g of a amber oil. Distillation of the oil gave 12.3 g of product, b.p. 93°-98° C. (1 mm).

EMBODIMENT 83

1-Methyl-3,3-tetramethylene-2-oxabicyclo[2.2.2]octan-6-ol

To a solution of 12.3 g of 1-methyl-3,3-tetramethylene-2-oxabicyclo[2.2.2]octan-6-one in 50 ml dimethylformamide and 50 ml tertbutyl alcohol was added 2.4 g of sodium borohydride portionwise over 10 minutes while maintaining the temperature at 20° C. with water cooling. The reaction mixture was stirred at room temperature for 5 hours, stored overnight under refrigeration, then quenched in 90 ml of water, stripped of solvents and extracted with methylene chloride. The organic phase was washed with saturated sodium chloride solution, dried with $MgSO_4$, and stripped to yield 12 g of oil. Distillation of the oil gave 10.4 g of product, b.p. 93°-8° C. (0.4 mm) as a mixture of exo and endo isomers.

EMBODIMENT 84

6-endo-Benzyloxy-1-methyl-3,3-tetramethylene-2-oxabicyclo[2.2.2]octane

To a stirred suspension of 1.2 g of 60% sodium hydride (hexane washed) in 30 ml of N,N-dimethylacetamide was added a solution of 4.9 g of the above mixture (1-methyl-3,3-tetramethylene-2-oxabicyclo[2.2.2]octan-6-ol) in 20 ml of dimethylacetamide at room temperature. This mixture was stirred for 1½ hours at 20° C., heated at 70°-80° C. for 1 hour, and cooled to room temperature, and then 5.2 g of benzyl bromide was added. The reaction mixture was stirred at room temperature for 1½ hours, at 50°-60° C. for 1 hour, and then at room temperature for 2 days, quenched in 300 ml of water, and extracted three times with 100 ml portions of methylene chloride. The combined extracts was washed successively with 300 ml of water and saturated sodium chloride solution, dried with $MgSO_4$, and stripped to give 6.2 g of oil. The oil was chromatographed on a silica gel dry column and eluted first with 65% hexane—35% methylene chloride and then with 30% hexane—70% methylene chloride chloride to give 1.5 g of the desired endo product and 1.7 g of the exo isomer.

EMBODIMENT 85

(±)-1,3,3-Trimethyl-2-oxabicyclo[2.2.2]octan-6-exo-ol

To a stirred solution of 30.8 g of (±)-alpha-terpineol in 300 ml of methylene chloride kept below 10° C. was added portionwise 43.0 g of 85% m-chloroperbenzoic acid. After 3 hours, 0.5 g of p-toluenesulfonic acid was added, and reaction was allowed to continue overnight at 5°-15° C. The resulting reaction mixture was washed with aqueous potassium carbonate, dried, and Claisen distilled to give 14.3 g of product b.p. 68°-75° C. (1 mm) and 12.6 of by-product, b.p. 75°-85° C. (1 mm). Redistillation of the product through a micro Vigreaux column gave 7.9 g of 90-95% purity product, b.p. 85°-95° C. (3 mm). A heart cut was recrystallized from pentane to give the product with m.p. 64°-66° C.

EMBODIMENT 86

(+)-alpha-Terpineol

Followiwng a procedure described in Matsubara, et al., *Chem. Abstr.*, 84:165069b (1976), 64.5 g of dichloroacetic acid was added dropwise over 20 minutes at 5°-6° C. to a magnetically stirred mixture of 68.0 g of (+)-alpha-pinene ([alpha]$_D$+47.1°) and 9.0 g of water. after stirring overnight at 5°-30° C. (ice allowed to melt slowly), the mixture was extracted with 400 ml of methylene chloride. The extract was washed successively with water, aqueous potassium carbonate solution and water, dried and Claisen distilled at 4 mm to give 11.2 g of forecut, b.p. 40°-71° C. and 47.5 g of the desired (+)-alpha-terpineol, b.p. 71°-83° C. Redistillation through a micro Vigreaux column gave 40.5 g of (+)-alpha-terpineol with [alpha]$_D$+79.3° (CHCl$_3$), b.p. 58°-60° C. (1 mm).

EMBODIMENT 87

(+)-1,3,3-Trimethyl-2-oxabicyclo[2.2.2]octan-6-exo-ol

To a stirred solution of 112 g of m-chloroperbenzoic acid in 500 ml of methylene chloride was added dropwise at 30°-35° over 1.5 hours a solution of 77 g of (+)-alpha-terpineol ([alpha]$_D$+77.1° (CHCl$_3$)) in 75 ml of methylene chloride. After stirring overnight at 25° C., the mixture was washed successively with one-fourth saturated potassium carbonate, saturated sodium sulfite and 2N sodium hydroxide. The dried methylene chloride solution was vacuum-concentrated (water aspirator) at 90° C. to a residue of 73 g. This was distilled through a micro Vigreaux column at 5 mm to give 42.3 of crude product, b.p. 95°-107° C. Recrystallization from 150 ml of pentane at −10° C. gave 10.2 g of product, m.p. 90°-93° C.; [alpha]$_D$+24.2° (CHCl$_3$).

EMBODIMENT 88

(+)-1,3,3-Trimethyl-2-oxabicyclo[2.2.2]octan-6-one

To a stirred solution of 8.7 g of (+)-1,3,3-trimethyl-2-oxabicyclo[2.2.2]octan-6-exo-ol in 250 ml of acetone was added 60 ml of water followed by 21.0 g of N-bromoacetamide. When the latter had dissolved within 1 minute, the reaction mixture was immediately cooled to less than 10° C. and stored overnight in a refrigerator. The orange-colored solution was poured with stirring into 200 ml of water containing 38 g of sodium sulfite. After vacuum concentration at 50°-55° C. to remove most of the acetone, the residue was treated with solid ammonium sulfate and extracted with four 125 ml portions of methylene chloride. The combined methylene chloride extract was washed with 100 ml of water, dried, and concentrated to a residue of 7.6 g. Recrystalization from 200 ml of pentane gave 6.0 g of product, m.p. 40°-48° C., [alpha]$_D$+74.3° (CHCl$_3$).

EMBODIMENT 89

(−)-1,3,3-Trimethyl-6-endo-(benzyloxy)-2-oxabicyclo[2.2.2]octane

To a stirred solution of 11.7 g of (+)-1,3,3-trimethyl-2-oxabicyclo[2.2.2]octan-6-one, [alpha]$_D$+71.7° (CHCl$_3$), in 110 ml of tert-butyl alcohol was added 2.7 g of sodium borohydride. After 3 hours at 25° C., the mixture was diluted with water and extracted 3 times with methylene chloride. The combined methylene chloride extract was washed, dried and concentrated to a constant weight of 11.1 g of white solid, 70:30 mixture of endo:exo alcohol corresponding to Embodiment 87. This solid was dissolved in 125 ml of N,N-dimethylacetamide, treated with 4.1 g of 50% sodium hydride (washed with hexane) and warmed with stirring from 25° to 90° C. over about 1 hour. The reaction mixture was cooled to 25° C. and treated with 9.5 g of benzyl chloride at 25°-30° C. When the reaction was no longer exothermic, heat was applied to bring the temperature to 50°-55° C. for 15 minutes. The mixture was cooled, poured into 400 ml of water, and extracted three times with methylene chloride. The combined methylene chloride extract was washed, dried and concentrated to a crude product containing a 70:30 ratio of endo-exo isomers by GLC analysis. Micro Vigreaux distillation at 0.2 mm gave the following:

| Cut | b.p., °C. | Weight, grams |
|---|---|---|
| 1 | 100–104 | 6.5 |
| 2 | 104–111 | 2.6 |
| 3 | 111–112 | 3.1 |
| Residue | | 1.1 |

Cuts 2 and 3 were combined and recrystallized from 5 ml of pentane at −10° C. to give 1.6 g of product, m.p. 48°-50° C., [alpha]$_D$−75.4° (CHCl$_3$).

EMBODIMENTS 90–115

Following procedures similar to Embodiments 75–89 above, additional endo-rich compounds were prepared as set forth in Table II below.

TABLE II

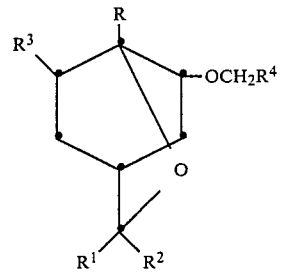

| Embodiment | R | R$^1$ | R$^2$ | R$^3$ | R$^4$ | b.p., °C. (mm) |
|---|---|---|---|---|---|---|
| 90 | CH$_3$ | CH$_3$ | CH$_3$ | H | 2-fluorophenyl | 112–118 (0.1) |
| 91 | CH$_3$ | CH$_3$ | CH$_3$ | H | 2-chlorophenyl | 129–134 (0.2) |
| 92 | CH$_3$ | CH$_3$ | CH$_3$ | H | 2-methylphenyl | 108–112 (0.15) |
| 93 | CH$_3$ | CH$_3$ | CH$_3$ | H | 2,6-dichlorophenyl | m.p. 100–102 |
| 94 | CH$_3$ | CH$_3$ | CH$_3$ | H | 2-pyridinyl | 112–113 (0.15) |
| 95 | CH$_3$ | C$_2$H$_5$ | C$_2$H$_5$ | H | 2,6-dichlorophenyl | m.p. 118–119 |
| 96 | CH$_3$ | C$_2$H$_5$ | C$_2$H$_5$ | H | 2-chlorophenyl | LIQUID* |
| 97 | CH$_3$ | C$_2$H$_5$ | C$_2$H$_5$ | H | 2-fluorophenyl | LIQUID* |
| 98 | CH$_3$ | C$_2$H$_5$ | C$_2$H$_5$ | H | 2-methylphenyl | LIQUID* |
| 99 | CH$_3$ | C$_2$H$_5$ | C$_2$H$_5$ | H | 2-pyridinyl | LIQUID* |
| 100 | CH$_3$ | —(CH$_2$)$_4$— | | H | 2-fluorophenyl | LIQUID* |
| 101 | CH$_3$ | CH$_3$ | CH$_3$ | H | 2,6-difluorophenyl | 106–110 (0.15) |
| 102 | CH$_3$ | —(CH$_2$)$_5$— | | H | phenyl | LIQUID* |
| 103 | CH$_3$ | —(CH$_2$)$_5$— | | H | 2-fluorophenyl | LIQUID* |
| 104 | CH$_3$ | —(CH$_2$)$_4$— | | H | 2-methylphenyl | LIQUID* |
| 105 | CH$_3$ | —(CH$_2$)$_5$— | | H | 2-methylphenyl | LIQUID* |
| 106 | CH$_3$ | C$_2$H$_5$ | C$_2$H$_5$ | H | 2,5-dimethylphenyl | LIQUID* |
| 107 | CH$_3$ | CH$_3$ | CH$_3$ | H | 2-methoxyphenyl | 128–130 (0.15) |
| 108 | CH$_3$ | C$_2$H$_5$ | C$_2$H$_5$ | H | 2,4-dimethylphenyl | LIQUID* |
| 109 | CH$_3$ | C$_2$H$_5$ | C$_2$H$_5$ | H | 2,6-difluorophenyl | LIQUID* |
| 110 | CH$_3$ | C$_2$H$_5$ | C$_2$H$_5$ | H | 2,6-dimethylphenyl | m.p. 68–70 |
| 111 | CH$_3$ | C$_2$H$_5$ | C$_2$H$_5$ | H | 2-ethylphenyl | LIQUID* |
| 112 | CH$_3$ | CH$_3$ | CH$_3$ | H | phenyl | 95 (0.1) |
| 113 | CH$_3$ | CH$_3$ | CH$_3$ | H | ethynyl | 92–97 (2.5) |
| 114 | CH$_3$ | CH$_3$ | CH$_3$ | H | 2-ethylphenyl | 113–115 (0.05) |
| 115 | CH$_3$ | CH$_3$ | CH$_3$ | H | 2-methylphenyl | 108–112 (0.15) |

*Isolated by column chromatography; boiling point not determined.

EMBODIMENT 116

1,3,3-Trimethyl-6-endo-7-syn-bis(benzyloxy)-2-oxabicyclo[2.2.2]octane

To a stirred solution of 2.5 g of 1,3,3-trimethyl-2-oxabicyclo[2.2.2]octane-6-endo-7-syn-diol (Tetrahedron, 27, 753 (1971)) in 50 ml of N,N-dimethylacetamide was added 0.7 g of 50% sodium hydride. After one hour at 25°-85° C., the mixture was cooled and treated with 1.7 g of benzyl chloride. After 30 min at 50°-60°

C., the mixture was cooled and poured into water. Extraction with methylene chloride, followed by Claisen distillation, gave 1.2 g of 1,3,3-trimethyl-7-endo-(benzyloxy)-2-oxabicyclo[2.2.2]octan-6-syn-ol, b.p. 135°–150° C. (0.2 mm). The residue from the distillation was recrystallized from hexane to give 0.6 g of the desired product, m.p. 99°–101° C.

EMBODIMENT 117

1,3,3-Trimethyl-6-syn-methoxy-7-endo-(benzyloxy)-2-oxabicyclo[2.2.2]octane

By procedures similar to those used in Embodiment 116 above, 1,3,3-trimethyl-7-endo-(benzyloxy)-2-oxabicyclo[2.2.2]octan-6-syn-ol was treated with methyl iodide in the presence of sodium hydride to yield the desired ether product, b.p. 130°–150° C. (0.1 mm).

EMBODIMENT 118

($\pm$)-2-Oxo-1-methyl-4-isopropyl-7-oxabicyclo[2.2.1]heptane

To a stirred solution of 4.5 g of oxalyl chloride in 70 ml of methylene chloride held at $-65°$ to $-60°$ C. was added dropwise over 5–10 minutes a solution of 6.6 g of dimethyl sulfoxide in 15 ml of methylene chloride. After an additional 10 minutes, there was added dropwise at $-60°$ C. a solution of 5.4 g of ($\pm$)-2-exo-hydroxy-1-methyl-4-isopropyl-7-oxabicyclo[2.2.1]heptane in 25 ml of methylene chrloride. After 15 minutes, 16.2 g of triethylamine was added dropwise at the same temperature. The cooling bath was removed and the mixture was allowed to warm slowly to 10° C. One hundred ml of water was added and stirring was continued for 20 minutes at 25° C. The organic layer was separated and the aqueous layer was extracted twice with 50 ml portions of methylene chloride. The combined methylene chloride solutions were dried and distilled to give 4.4 g of the desired product, b.p. 90°–102° C. (14 mm).

EMBODIMENT 119

($\pm$)-2-endo-Hydroxy-1-methyl-4-isopropyl-7-oxabicyclo[2.2.1]heptane

To a stirred solution of 6.2 g of ($\pm$)-2-oxo-1-methyl-4-isopropyl-7-oxabicyclo[2.2.1]heptane in 60 ml of t-butanol was added 1.4 g of sodium borohydride. After 6 hours at 25° C., the mixture was diluted with water and extracted with four 100 ml portions of methylene chloride. The combined methylene chloride extracts were washed, dried and concentrated to a residue of 6.2 g. The residue was chromatographed using a 1:4:20 ratio of tetrahydrofuran-ethyl acetate-hexane as eluent to yield 3.3 g of 80% pure ($\pm$)-2-endo-1-methyl-4-isopropyl-7-oxabicyclo[2.2.1]heptane containing 20% of the corresponding exo-isomer.

EMBODIMENT 120

($\pm$)-2-endo-2-(Benzyloxy)-1-methyl-4-isopropyl-7-oxabicyclo[2.2.1]heptane

By procedures similar to those described in Embodiment 3, ($\pm$)-2-endo-hydroxy-1-methyl-4-isopropyl-7-oxabicyclo[2.2.1]heptane was treated with benzyl chloride to yield the desired product, b.p. 103° C. (0.15 mm).

EMBODIMENT 121

($\pm$)-2-exo-(Benzyloxy)-1-methyl-7-oxabicyclo[2.2.1]heptane

By procedures similar to those described in Embodiment 3, ($\pm$)-2-exo-hydroxy-1-methyl-7-oxabicyclo[2.2.1]heptane was prepared by treatment of 4-methyl-3-cyclohexen-1-one with sodium borohydride followed by epoxidation-cyclization and ether formation to yield the desired product, b.p. 100°–101° C. (0.2 mm).

EMBODIMENT 122

($\pm$)-2-exo-(Benzyloxy)-1-methyl-4-(allyl)-7-oxabicyclo[2.2.1]heptane ($\pm$)-2-exo-hydroxy-1-methyl-4-(allyl)-7-oxabicyclo[2.2.1]heptane (prepared by treating 4-methyl-3-cyclohexen-1-one with allyl magnesium bromide followed by epoxidation-cyclization) was treated with benzyl chloride by procedures similar to Embodiment 3 above to yield the desired product, b.p. 109°–115° C. (0.1 mm).

EMBODIMENT 123

($\pm$)-2-exo-(2-Fluorobenzyloxy)-1-methyl-4-phenyl-7-oxabicyclo[2.2.1]heptane

By procedures similar to those described in Embodiment 3, ($\pm$)-2-exo-hydroxy-1-methyl-4-phenyl-7-oxabicyclo[2.2.1]heptane, was treated with 2-fluorobenzyl chloride to yield the desired product as an oil.

EMBODIMENT 124

($\pm$)-2-exo-(2-Methylbenzyloxy)-1-methyl-4-phenyl-7-oxabicyclo[2.2.1]heptane

By procedures similar to those described in Embodiments 1–7, ($\pm$)-2-exo-hydroxy-1-methyl-4-phenyl-7-oxabicyclo[2.2.1]heptane was treated with 2-methylbenzyl chloride to yield the desired product as an

EMBODIMENTS 125–162

Following procedures similar to those described for Embodiments 1–3, 8–16, 29, 33, 35–41, 44, 61, 62, 70–71 and 118–120, the 1-methyl-4-isopropyl-7-oxabicyclo[2.2.1]heptan-2-ol ethers listed in Table III were prepared.

TABLE III

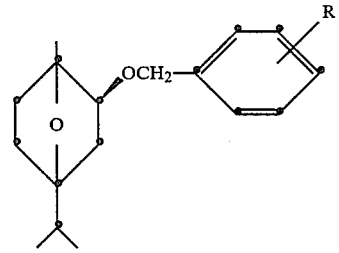

| Embodiment | R | b.p., °C. (mm) |
|---|---|---|
| 124 | 3-Cl | 128–135 (0.15) |
| 125 | 4-Cl | 128–134 (0.15) |
| 126 | 3,4-Cl$_2$ | 140–149 (0.15) |
| 127 | 2,4-Cl$_2$ | 138–150 (0.15) |

TABLE III-continued

[Structure: 7-oxabicyclo[2.2.1]heptane with OCH₂-phenyl-R substituent]

| Embodiment | R | b.p., °C. (mm) |
|---|---|---|
| 128 | —OCH₂-naphthyl | 150–164 (0.15) |
| 129 | 3-CF₃ | 112–117 (0.15) |
| 130 | 3-CH₃ | 115–122 (0.15) |
| 131 | 4-CH₃ | 117–124 (0.15) |
| 132 | 2-OCH₃ | 130–137 (0.15) |
| 133 | 4-OCH₃ | 126–134 (0.15) |
| 134 | 2,5-Cl₂ | 129–137 (0.1) |
| 135 | 2-F, 6-Cl | 116–124 (0.1) |
| 136 | 3-OCH₃ | 126–131 (0.1) |
| 137 | 3,5-Cl₂ | 132–137 (0.1) |
| 138 | 2,6-(CH₃)₂ | 111–115 (0.1) |
| 139 | 2-Br | 128–135 (0.1) |
| 140 | 2-CF₃ | 105–110 (0.1) |
| 141 | 4-CF₃ | 107–113 (0.1) |
| 142 | 3-NO₂ | 150–153 (0.1) |
| 143 | 2,6-F₂ | 115–120 (0.2) |
| 144 | 2-CN | 140–148 (0.15) |
| 145 | 2-CONH₂ | 180–184 (0.2) |
| 146 | 2,6-(OCH₃)₂ | 147–150 (0.25) |
| 147 | 2-COOH | m.p. 96–108 |
| 148 | 2-OC₂H₅ | 132–137 (0.15) |
| 149 | 2-N(CH₃)C(O)CH₃ | 154–163 (0.2) |
| 150 | 2-CH₂NH₂ | 138–140 (0.1) |
| 151 | 2-NHCH₃ | 130 (0.1) |
| 152 | 2-N(Me)Et | 130–140 (0.15) |
| 153 | 2-CH₂NHC(O)CH₃ | 194–197 (0.2) |
| 154 | 2-SCH₃ | 143–146 (0.15) |
| 155 | 2-S(O)CH₃ } 2 Isomers | m.p. 108–110 |
| 156 | 2-S(O)CH₃ | |
| 157 | 2-OCH₂Ph | 173–175 (0.1) |
| 158 | 2-OH | 137–138 (0.1) |
| 159 | [pyrimidinyl] | 115–125 (0.1) |
| 160 | CN | 103–105 (1.0) |
| 161 | [pyridazinyl N=N] | mp. 105–108 |
| 162 | [isoxazolyl-CH₃] | 121–123 (0.2) |

EMBODIMENT 163

(±)-2-exo-Benzyloxy-1-phenyl-4-methyl-7-oxabicyclo[2.2.1]heptane

Following procedures similar to those described for Embodiment 3, (±)-2-exo-benzyloxy-1-phenyl-4-methyl-7-oxabicyclo[2.2.1]heptane was prepared by treating the corresponding alcohol with benzyl chloride to yield the desired product, b.p. 125°–128° C. (0.1 mm).

EMBODIMENTS 164–166

The 4-(1-chloro-1-methylethyl) ether compounds of Embodiments 51, 72 and 73 were each respectively treated with 1.1 molar equivalents of sodium hydride in N,N-dimethylacetamide at 80° C. for 2 hours to give the dehydrochlorinated products set forth in Table IV below.

TABLE IV

[Structure: 7-oxabicyclo[2.2.1]heptane with R₁, R₂ substituents and OCH₂-phenyl-R₃]

| Embodiment | R₁ | R₂ | R₃ | b.p., °C. (mm) |
|---|---|---|---|---|
| 164 | CH₃ | —C(CH₃)=CH₂ | 2-CH₃ | 110–114 (0.1) |
| 165 | CH₃ | —C(CH₃)=CH₂ | 2-F | 105 (0.1) |
| 166 | CH₃ | —C(CH₃)=CH₂ | H | 110–114 (0.1) |

EMBODIMENT 167

2-Acetoxy-2-cyano-1,4,5,6-tetramethyl-7-oxabicyclo[2.2.1]hept-5-ene

A mixture of 6.2 g tetramethylfuran and 5.6 g of alpha-acetoxyacrylonitrile was allowed to stand for 4 days. After stabilization at 25° C. and 0.1 mm there was obtained 11.4 g of a mushy solid. This was stirred for 0.5 hour with 50 ml of pentane and filtered to give 7.1 g of product, m.p. 72°–84° C. Recrystallization from ether-pentane (1:2) gave 4.6 g of the desired product, m.p. 87°–88° C.

In another experiment, 27.8 g of tetramethylfuran and 24.9 g of nitrile were allowed to stand for one week. A solid product (A) weighing 39.9 g was obtained by decantation. It was used as such for conversion to the ketone in the following Embodiment 168.

EMBODIMENT 168

1,4,5,6-Tetramethyl-7-oxabicyclo[2.2.1]hept-5-en-2-one

To a stirred solution of 20.4 g of sodium hydroxide in 400 ml of ethanol was added 39.9 g of crude product of the second experiment of Embodiment 167 above. After 24 hours, the mixture was poured into 1 liter of water and extracted with five 200 ml portions of methylene chloride. The combined methylene chloride extracts were washed, dried, concentrated, and Claisen distilled to give 23.7 g of the desired product, b.p. 63° C. (2 mm).

EMBODIMENT 169

1,4,5,6-Tetramethyl-7-oxabicyclo[2.2.1]hept-5-en-2-ol

To a stirred solution of 10.3 g of the ketone of Embodiment 168 above in 75 ml of t-butanol held at 25° C. was added 2.3 g of sodium borohydride. After 6 hours, the mixture was diluted with three volumes of water and extracted three times with methylene chloride. The combined methylene chloride extracts were washed, dried and vacuum concentrated to a residue of 9.8 g (A) of the desired alcohol as a mixture of the endo and exo alcohols.

EMBODIMENT 170

2-Benzyloxy-1,4,5,6-tetramethyl-7-oxabicyclo[2.2.1]hept-5-ene

The mixture of endo and exo alcohol product from Embodiment 169 above was dissolved in 100 ml of dimethylacetamide, treated with 2.9 g of 60% sodium hydride, and warmed to 80° C. over a period of 0.5 hr. After cooling to 25° C., a 9.1 g portion of benzyl chloride was added and the mixture was held at 50°-60° C. for 0.5 hr. Workup as above afforded a residue of 15.8 g. GLC analysis indicated a 76:24 ratio of endo:exo isomers.

Distillation of the residue at 1.0 mm using a micro Vigreaux column afforded the following cuts, cuts 2-5 being the desired ether product.

| Embodiment | Distillation Cuts | b.p., °C. | Wt, g | GLC Analysis % Endo | % Exo |
|---|---|---|---|---|---|
| 170 | 1 | 35–122 | 1.4 | — | — |
| 170 (a) | 2 | 122–128 | 7.5 | 91 | 7 |
| 170 (b) | 3 | 128–135 | 4.2 | 82 | 17 |
| 170 (c) | 4 | 135–138 | 1.1 | 55 | 44 |
| 170 (d) | 5 | <125 (<1 mm) | 2.0 | 15 | 85 |

EMBODIMENT 171

2-Benzyloxy-1,4,5,6-tetramethyl-7-oxabicyclo[2.2.1]heptane (a) To a 500 ml Parr hydrogenation vessel were charged 0.9 g of the distillation cut 5 from Embodiment 170 (d) above, 50 ml of ethanol, 0.3 g of 5% palladium on carbon and 2 ml of triethylamine. After shaking at 25° C. for 4 hours, hydrogen absorption ceased. The catalyst was removed by filtration through filter aid, and the filtrate was vacuum-concentrated to give 0.8 g of 2-exo-benzyloxy-1,4,5,6-tetramethyl-7-oxabicyclo[2.2.1]heptane as a colorless oil, b.p. 135 (0.1 mm).

(b) In a similar manner, the endo ether was prepared from the distillation cut 2 from Embodiment 170 (a) above, and had a b.p. of 97°-99° C. (0.15 mm).

EMBODIMENT 172

1,4,5,6-Tetramethyl-7-oxabicyclo[2.2.1]hept-5-en-2,3-cis-diol, Cyclic Carbonate (exo and endo)

(a) A mixture of 4.8 g of vinylene carbonate and 7.0 g of tetramethylfuran were allowed to warm overnight on the steam bath. The resulting dark solution was distilled at 45° C. and 0.1 mm to give 9.1 g of a semi-solid mixture of isomers. The mixture was stirred 5 hours with 100 ml of diethyl ether and filtered to give 1.9 g of 1,4,5,6-tetramethyl-7-oxabicyclo[2.2.1]hept-5-en-2,3-cis-exo-diol cyclic carbonate, m.p. 164°–165° C.

(b) The filtrate from this isolation was stored overnight at −15° C. to give 2.7 g of the desired cis-endo-diol cyclic carbonate, m.p. 98°–112° C. Recrystallization from 30 ml of diethyl ether gave the analytical sample, m.p. 103°–110° C.

EMBODIMENT 173

1,4,5,6-Tetramethyl-7-oxabicyclo[2.2.1]hept-5-en-2,3-cis-exo-diol

To a stirred solution of 0.6 g of the cis-exo-diol cyclic carbonate of Embodiment 172 (a) above in 15 ml of ethanol was added a solution of 0.6 g of sodium hydroxide in 5 ml of water. After 18 hours at 25° C., the mixture was filtered to remove 0.3 g of sodium carbonate and the filtrate was treated with solid carbonate dioxide and vacuum-concentrated at 60° C. The residue was boiled with ethyl acetate, and filtered hot, and the filtrate was concentrated to a residue of 0.4 g, m.p. 142°–145° C. The analytical sample was prepared by recrystallization from acetone-pentane, m.p. 144°–145° C.

EMBODIMENT 174

2-exo-Benzyloxy-1,4,5,6-tetramethyl-7-oxabicyclo[2.2.1]hept-5-en-3-exo-ol

To a stirred mixture of 4.7 g of the cis-exo-diol of Embodiment 173 above and 75 ml of dimethylformamide was added portionwise at 25° C. 1.1 g of 60% sodium hydride (hexane washed). When hydrogen evolution was slow, the solution was cooled to 10° C. and treated with 3.4 g of benzyl chloride. After 2 hours at 10°–25° C., the mixture was poured into water and extracted twice with methylene chloride. The combined methylene chloride was washed, dried, concentrated and micro-Claisen-distilled to give 4.6 g of the desired ether product, b.p. 130°–135° C. (0.1 mm).

EMBODIMENT 175

2-exo-Benzyloxy-3-exo-methoxy-1,4,5,6-tetramethyl-7-oxabicyclo[2.2.1]hept-5-ene

To a stirred mixture of 3.6 g of the ether of Embodiment 174 above and 50 ml of dimethylformamide was added 0.6 g of 60% sodium hydride (hexane-washed). Heat was applied to raise the temperature to 80° C. over a 1 hour period. After cooling to 20° C., 3 ml of methyl iodide was added. This caused a temperature rise to 35° C. Stirring was continued at ambient temperature for 0.5 hr, and the solution was processed as above to give 3.0 g of the desired ether product, b.p. 120° C. (0.1 mm).

EMBODIMENT 176

1,4,5,6-Tetramethyl-7-oxabicyclo[2.2.1]heptane-2,3-cis-exo-diol Cyclic Carbonate A 6.7 g portion of the unsaturated-cis-exo-diol cyclic carbonate of Embodiment 172 (a) above was shaken with hydrogen at 50 psig using 75 ml of absolute ethanol as solvent and 2.0 g of 5% palladium on carbon as catalyst. Hydrogenation was complete in 0.5 hr. Vacuum concentration gave a mixture of solid product and catalyst. This was treated with hot acetone and filtered to remove the catalyst. Chilling of the filtrate gave 4.1 g of the desired product, m.p. 162°–166° C. The analytical sample melted at 166°–168° C.

EMBODIMENT 177

1,4,5,6-Tetramethyl-7-oxabicyclo[2.2.1]heptane-2,3-cis-exo-diol

A solution of 2.5 g of the cyclic carbonate of Embodiment 176 above in 50 ml of ethanol was treated with a solution of 2.0 g of sodium hydroxide in 15 ml of water to give 2.1 g of the desired product, m.p. 179°–183° C. without recrystallization.

EMBODIMENT 178

2-exo-Benzyloxy-2-exo-methoxy-1,4,5,6-tetramethyl-7-oxabicyclo[2.2.1]heptane

To a stirred solution of 1.7 g of the diol of Embodiment 177 above in 25 ml of dimethylacetamide was added 0.37 g of 60% sodium hydride. After 0.5 hr at 25° C., hydrogen evolution was slow. The mixture was cooled to 10° C. and treated with 1.15 g of benzyl chloride. After 0.5 hr at 10°–25° C. and 0.5 hr at 45°–50° C., the mixture was poured into water and extracted three times with hexane. The combined hexane extracts were washed, dried and vacuum concentrated to constant weight. This residue was subjected to the above procedure, except that an excess of methyl iodide was substituted for benzyl chloride. Workup as above, followed by micro-Claisen distillation, gave 1.9 g of the desired product, b.p. 123°–133° C. (0.2 mm).

EMBODIMENT 179

2-exo-Benzyloxy-5,6-epoxy-3-exo-methoxy-1,4,5,6-tetramethyl-7-oxabicyclo[2.2.1]heptane To a cold, stirred solution of 1.3 g of the ether of Embodiment 175 above in 25 ml of methylene chloride was added 1.0 g of 85% m-chloroperbenzoic acid. After 2 hours at 5°–25° C., the mixture was washed with dilute potassium carbonate containing dilute sodium sulfite, dried and concentrated under vacuum at 75° C. to a constant weight of 1.3 g of the desired ether product.

EMBODIMENT 180

4-Methyl-3-cyclohexen-1-one

A mixture of 352 g of 1-methoxy-4-methyl-1,4-cyclohexadiene (85% purity), 1350 ml of diethyl ether, 28 g of oxalic acid and 900 ml of water was stirred mechanically for 21 hours at 25° C. The aqueous layer was separated and extracted twice with ether. The combined ether solutions were washed with sodium bicarbonate, dried, concentrated and Claisen-distilled to give 250 g of 4-methyl-3-cyclohexen-1-one, b.p. 63°–65° C. (13 mm).

EMBODIMENT 181

2,2,4-Trimethyl-3-cyclohexen-1-one

To a 500 ml 3-neck, round-bottom flask were charged 37.5 g of 88% purity 4-methyl-3-cyclohexen-1-one, 100 ml of ether, 89.5 g of methyl iodide and 0.3 g of methyltrioctylammonium chloride. This mixture was stirred mechanically at ambient temperature and treated with 30 g of granular sodium hydroxide. After 20 minutes at gentle reflux (no cooling used), heat was applied to maintain the reflux for 2 hours longer. The cooled mixture was diluted with ether and treated with water to dissolve the suspended salts. The ether was separated and the aqueous layer was extracted with ether. The combined ether extracts were washed, dried, concentrated and Claisen-distilled to give 36.5 g of the desired product, b.p. 60° C. (10 mm).

EMBODIMENT 182

2,2,4-Trimethyl-3-cyclohexen-1-ol

To a stirred solution of 27.6 g of the ketone of Embodiment 181 above in 250 ml of ethanol was added portionwise 7.6 g of sodium borohydride. A cooling bath was used to hold the temperature at 25°–30° C. After 2 hours the mixture was poured into water and extracted three times with methylene chloride. The combined methylene chloride extracts were washed, dried, and concentrated at 25° C. and 0.1 mm to give 27.7 g of the desired product.

EMBODIMENT 183 cis-3,4-Epoxy-2,2,4-trimethylcyclohexanol

A solution of 27.7 g of the alcohol of Embodiment 182 above in 250 ml of methylene chloride was treated with 1.0 g of vanadium(IV) bis(2,4-pentanedioate) oxide and 22.0 g of 90% tert-butylhydroperoxide. After stirring overnight at 25° C., the mixture was washed with 1N sodium hydroxide, dried and Claisen-distilled to give 23.7 g of the desired product, b.p. 58°–61° C. (1 mm).

EMBODIMENT 184

1,3,3-Trimethyl-7-oxabicyclo[2.2.1]heptan-2-exo-ol

To a stirred solution of 20.0 g of the epoxy-alcohol of Embodiment 183 above in 200 ml of methylene chloride held at 25° C. was added dropwise over 20 min a solution of 0.4 g of p-toluenesulfonic acid in 5 ml of glyme. After 1 hour longer, the solution was washed with dilute potassium carbonate, dried, concentrated, and Claisen-distilled to give 11.1 g, b.p. 55°–77° C. (1.0–0.1 mm). This was redistilled through a micro Vigreaux column to give 2.8 g of the desired product, b.p. 77°–80° C. (3.0 mm).

EMBODIMENT 185

2-exo-Benzyloxy-1,3,3-trimethyl-7-oxabicyclo[2.2.1]heptane

A stirred solution of 2.2 g of the product of Embodiment 184 above in 30 ml of N,N-dimethylacetamide was treated with 0.8 g of 50% sodium hydride and held at 80°–85° C. for 0.5 hr. The mixture was cooled to 25° C. and 2.0 g of benzyl chloride was added. An exothermic reaction carried the temperature to 40°–45° C. Heat was applied to hold the temperature at 50°–55° C. for 0.5 hr. The cooled solution was poured into water and extracted twice with hexane. The combined hexane extracts were washed, dried, concentrated and micro-Claisen-distilled to give 2.3 g of the desired product, b.p. 97°–99° C. (0.1 mm).

EMBODIMENT 186

1,2,2,4-Tetramethyl-3-cyclohexen-1-ol

To a stirred solution of 80 ml of 2.9M methyl magnesium chloride (in tetrahydrofuran) mixed with 200 ml of dry tetrahydrofuran was added dropwise at 25°–30° C. a solution of 27.6 g of ketone of Embodiment 181 above in 30 ml of tetrahydrofuran. After 1 hour longer at 25° C. and 1 hour at 45°–50° C., the mixture was cooled and treated carefully with 50 ml of saturated ammonium sulfate. The mixture was extracted twice with diethyl ether, and the combined ether extracts were dried, concentrated and distilled through a micro Vigreaux column to give 12.5 g (A), b.p. 115°–125° C. (100 mm), which was mainly unchanged ketone starting material and 11.1 g (B), b.p. 125°–115° C. (100–50 mm), which was the desired product of 81% purity. The final cut of 2.0 g (C), b.p. 115°–120° C. (50–20 mm) was the desired product of 87% purity.

EMBODIMENT 187

1,3,3,4-Tetramethyl-7-oxabicyclo[2.2.2]heptan-2-exo-ol

To a stirred solution of 11.1 g of 81% purity 1,2,2,4-tetramethyl-3-cyclohexan-1-ol and vanadium(IV) bis(2,4-pentanedioate)oxide in 100 ml of methylene chloride was added 8.0 g of 90% tert-butyl hydroperoxide. The exothermic reaction produced a gentle reflux within 10 minutes. After 1.5 hours longer at reflux, the reaction mixture was cooled, dried with magnesium sulfate, stirred at 25° C., and treated dropwise over 15 minutes with a solution of 0.25 g of p-toluenesulfonic acid in 3.2 ml of glyme. After 1.5 hours, the solution was washed with dilute sodium carbonate, dried, concentrated, and Claisen-distilled to give 8.5 g of 66% purity (GLC) product, b.p. 60°–80° C. (10–1 mm). Recrystallization from concentrated pentane solution at −15° C. gave 2.8 g of the desired product, m.p. 58°–62° C.

EMBODIMENT 188

2-exo-Benzyloxy-1,3,3,4-tetramethyl-7-oxabicyclo[2.2.1]heptane

Following procedures similar to those described in Embodiment 185, the desired product was prepared by treating the exo-alcohol of Embodiment 187 above with benzyl chloride to yield the ether, b.p. 95°–100° C. (0.2 mm).

EMBODIMENT 189

2,2,4,6,6-Pentamethyl-3-cyclohexen-1-one

To a stirred solution of 27.6 g of the ketone of Embodiment 181 above and 62.5 g of methyl iodide in 350 ml of tetrahydrofuran was added portionwise with cooling at 25°–35° C. 20.2 g of 50% sodium hydride. The reaction was completed by refluxing for an hour longer.

The cooled mixture was filtered and the filter cake was washed with tetrahydrofuran. The filtrate was concentrated to low volume and poured into water. Three extractions with methylene chloride, followed by washing, drying, concentration and Claisen-distillation, gave 25.6 g of the desired product.

EMBODIMENT 190

2-exo-Benzyloxy-1,3,3,4,5,5-hexamethyl-7-oxabicyclo[2.2.1]heptane

Following procedures described in Embodiments 181–188, the desired product was prepared by treating the ketone of Embodiment 189 above with methyl magnesium chloride to yield the corresponding alcohol which was epoxidized and cyclized to the oxabicycloalkanol and then treated with benzyl chloride to yield the desired product, b.p. 110°–115° C. (0.1 mm).

EMBODIMENT 191

2-endo-Hydroxy-1,2-dimethyl-4-isopropyl-7-oxabicyclo[2.2.1]heptane

To a stirred mixture of 32 ml of 2.9M methyl magnesium chloride and 75 ml of dry tetrahydrofuran was added dropwise at 20°–25° C. a solution of 12.6 g of the ketone of Embodiment 118 above in 25 ml of tetrahydrofuran. The reaction was completed by refluxing for 1 hour. To the cooled mixture was added dropwise 75 ml of water at 15°–25° C. The mixture was extracted twice with 100 ml portions of diethyl ether and the combined ether extracts were dried and distilled to give 9.9 g of the desired product, b.p. 85° C. (4 mm).

EMBODIMENT 192

2-endo-Benzyloxy-1,2-dimethyl-4-isopropyl-7-oxabicyclo[2.2.1]heptane

To a stirred solution of 3.7 g of alcohol of Embodiment 191 above in 25 ml of N,N-dimethylacetamide was added 0.9 g of 60% sodium hydride. The mixture was warmed to 80°–85° C. and held there until hydrogen evolution ceased. After cooling to 25° C., 2.8 g of benzyl chloride was added and the mixture was again held at 80° C. for 2 hours. The cooled mixture was poured into water and extracted twice with methylene chloride. After washing and drying, the combined methylene chloride extracts were concentrated and micro Claisen-distilled to give 3.2 g of the desired product, b.p. 106°–110° C. (0.15 mm).

EMBODIMENT 193

1-(Ethoxycarbonylmethyl)-4-methyl-3-cyclohexen-1-ol

To a stirred mixture of 26.0 g of zinc dust (washed twice with 10% hydrochloric acid, then successively with water, acetone and ether, and dried overnight at 60° C. in a vacuum oven), 2.0 g of iodine and 40 ml of benzene was added rapidly at 65°–75° C. a solution of 22.0 g of 4-methyl-3-cyclohexen-1-one of Embodiment 180 above and 62.6 g of ethyl bromoacetate in 400 ml of benzene. After 5 hours at reflux the mixture was cooled to <10° C. and treated dropwise with 300 ml of 10% acetic acid. After 15 minutes, the layers were separated and the aqueous layer was extracted twice with 150 ml of benzene. The combined organic layers were washed successively with water, sodium bicarbonate solution and water. After drying and concentration, Claisen distillation gave 33.0 g of the desired product, b.p. 82°–84° C. (0.5 mm).

EMBODIMENT 194

4-(Ethoxycarbonylmethyl)-2-exo-hydroxy-1-methyl-7-oxabicyclo[2.2.1]heptane

To a stirred, refluxing solution of 46.2 g of alcohol of Embodiment 193 above and 1.2 g of vanadium(IV) bis(2,4-pentanedionate)oxide in 400 ml of methylene chloride was added dropwise 25.3 g of 90% tert-butyl hydroperoxide. After 2 hours longer at reflux, the solution was cooled, dried over magnesium sulfate, and filtered through Celite. The stirred filtrate was treated with 12 ml of glyme containing 1.0 g of p-toluenesulfonic acid. After 18 hours at 25° C., the mixture was washed with dilute carbonate and dried. Vacuum-concentration at 50° C. gave 52.3 g of dark amber oil. GLC analysis indicated the presence of 56% of desired product. Purification via HPLC using ethyl acetate as eluent gave 16.8 g of the desired product as an oil.

EMBODIMENT 195

2-exo-Benzyloxy-4-(benzyloxycarbonylmethyl)-1-methyl-7-oxabicyclo[2.2.1]heptane

To a stirred solution of 4.3 g of alcohol of Embodiment 194 above in 15 ml of ethanol was added a solution of 0.9 g of sodium hydroxide in 3 ml of water. After 24 hours at 25° C., the mixture was vacuum-concentrated at 30° C. (<1 mm). The residue was dissolved in 30 ml of N,N-dimethylacetamide and treated with 1.0 g of 50% sodium hydride. After 6 hours at 25° C., 5.5 g of benzyl chloride was added, and stirring was continued for 4 days. The mixture was poured into water, extracted 3 times with methylene chloride, and the combined methylene chloride extracts were washed, dried and concentrated to a residue of 8.1 g. This oil was purified by column chromatography to give 2.6 g of desired product as an oil.

EMBODIMENT 196

2-exo-Benzyloxy-4-carboxymethyl-1-methyl-7-oxabicyclo[2.2.1]heptane

To a stirred solution of 3.1 g of ether of Embodiment 195 above in 15 ml of ethanol was added a solution of 0.6 g of sodium hydroxide in 2.5 ml of water. After 19 hours at 25° C., the mixture was acidified to Congo Red paper using 6N hydrochloric acid. After dilution with 150 ml of methylene chloride, the organic layer was washed twice with 25 ml portions of water. The dried methylene chloride solution was concentrated to a residue of 2.8 g. This was purified by preparative plate chromatography to give 1.7 g of the desired product as an oil.

EMBODIMENT 197

3,4-cis-Epoxy-1-isopropyl-4-methylcyclohexan-1-ol

To a solution of 30.8 g of (+)-terpinen-4-ol in 250 ml of toluene containing 1.0 g of vanadium(IV) bis(],4-pentanedioate)oxide held at 45° C. was added 22.0 g of 90% tert-butyl hydroperoxide. Cooling was used to maintain the reaction temperature at 45°–50° C. for several minutes. After 2 hours longer at the same temperature, the mixture was cooled, washed with 1N sodium hydroxide, dried, and Claisen-distilled to give 30.6 g of the desired product, b.p. 75° C. (2 mm). The NMR spectrum was the same as that reported in the literature.

EMBODIMENT 198

2-exo-Hydroxy-1-methyl-4-isopropyl-oxabicyclo[2.2.1-]heptane

Following procedures similar to those described in Embodiment 1 above, the epoxy-alcohol of Embodiment 197 above was treated with p-toluenesulfonic acid to give the desired product.

EMBODIMENT 199

$\alpha,\alpha,\alpha',\alpha'$-Tetrabromoacetone

Bromine (160 g) was added dropwise over 1.5 hours to an ice-cold mixture of acetone (14.5 g) and 48% aqueous hydrobromic acid (25 ml). The mixture was allowed to warm to 23° C., held for 16 hours, and diluted with water (200 ml). The heavy organic layer was separated and dissolved in diethyl ether. The ethereal layer was washed with saturated aqueous bicarbonate and brine, and then dried over sodium sulfate. Evaporative removal of solvent produced 82.09 g of a yellow oil containing a 7:1 mixture of the desired product and $\alpha,\alpha,\alpha'$-tribromoacetone, respectively. Fractional distillation through a short Vigreaux provided 56.9 g of the desired product as a light tan, low-melting solid.

EMBODIMENT 200

2,4-Dibromo-1,5-dimethyl-8-oxabicyclo[3.2.1]oct-6-en-3-one

A mixture of zinc/silver couple (2.23 g) and 2,5-dimethylfuran (25 ml) in dry tetrahydrofuran (35 ml) was placed in a 100 ml three-necked flask and cooled at $-10°$ C. A solution of $\alpha,\alpha,\alpha',\alpha'$-tetrabromoacetone in dry tetrahydrofuran (15 ml) was added dropwise over a period of 3 hours with stirring, and the resulting mixture was allowed to warm to room temperature with stirring for an additional 16.5 hours. The insoluble materials were removed by filtration and the filtrate was concentrated. The resulting tarry, brown residue was eluted through a florisil column with diethyl ether to give an orange solid. Further purification by flash-column chromatography produced the desired product (3.58 g) as a colorless solid, m.p. 115°–20° C.

EMBODIMENT 201

1,5-Dimethyl-8-oxabicyclo[3.2.1]oct-6-en-3-one

To a stirred slurry of 2,4-dibromo-1,5-dimethyl-8-oxabicyclo[3.2.1]oct-6-en-3-one (18.0 g) in a saturated methanolic solution of ammonium chloride (514 ml) was added portionwise zinc/copper couple (51 g) over 30 minutes at 23° C. The suspension was stirred for an additional 2 hours and filtered. The filtrate was diluted with a saturated $Na_2H_2$-ethylenediaminetetraacetic acid solution (400 ml). Extraction with methylene chloride (5×100 ml) and drying ($MgSO_4$) produced, upon evaporative removal of solvent, the desired ketone (9.0 g). Bulb-to-bulb distillation <80° C. and 0.5 mm afforded the desired product (7.3 g) as colorless crystals, m.p. 62°–63° C.

EMBODIMENT 202

1,5-Dimethyl-8-oxabicyclo[3.2.1]oct-6-en-3-ol

To a stirred suspension of lithium aluminum hydride (4.6 g of a 57% oil suspension) in dry diethyl ether (300 ml) was added a solution of 1,5-dimethyl-8-oxabicyclo[3.2.1]oct-6-en-3-one (10.0 g) in diethyl ether (50 ml) over 0.5 hour at 20° C. The reaction mixture was held for 2 hours at 20° C., cooled to 0° C., and washed successively with water (2.5 ml), 15% aqueous sodium hydroxide (2.5 ml) and water (7.5 ml), and filtered. The filter cake was washed with diethyl ether, and the combined ether filtrates were dried ($MgSO_4$), filtered and concentrated to give 13.0 g of oil. The oil was eluted through a column of florisil first with hexane and then diethyl ether. The ether fractions were combined and concentrated to give the desired product (10.0 g) as a 66:34 mixture of epimers.

EMBODIMENT 203

1,5-Dimethyl-8-oxabicyclo[3.2.1]oct-6-en-3-yl p-Toluenesulfonate para-Toluenesulfonyl chloride (15.5 g,) was added portionwise over 20 minutes to an ice-cold stirred solution of 1,5-dimethyl-8-oxabicyclo[3.2.1]oct-6-en-3-ol (10.0 g,) in dry pyridine (75 ml). The reaction mixture was stirred at 0° C. for 0.5 hour, allowed to stand in a refrigerator (0° C.) for 72 hours, and poured into a mixture of 80 ml concentrated hydrochloric acid and 100 g of ice. After stirring for 10 minutes, the precipitated solid was filtered. The collected solid dissolved methylene chloride was dried (MgSO4), filtered and concentrated to give 17.6 g (88%) of the desired product, m.p. 75°–77° C., as a 70:30 mixture of epimers.

EMBODIMENT 204

1,5-Dimethyl-8-oxabicyclo[3.2.1]octan-6-exo-ol

A stirred, ice-cold solution of 1,5-dimethyl-8-oxabicyclo[3.2.1]oct-6-ene-3-yl p-toluenesulfonate of Embodiment 203 (6.16 g) in dry tetrahydrofuran (80 ml) was treated with a 1M solution of Super Hydride in tetrahydrofuran (80 ml) dropwise over 30 minutes. The mixture was allowed to warm slowly to room temperature and then heated at reflux overnight. The reaction mixture was cooled to 0° C. and treated over 5 minutes with ethyl iodide (4.8 ml). After warming to 23° C. and holding for 1 hour at 23° C., the mixture was recooled to 0° C. To the resulting mixture containing 1,5-dimethyl-8-oxabicyclo[3.2.1]hept-6-ene as an intermediate, a 1M solution of borane in tetrahydrofuran (40 ml) was added over a 20 minute period. The mixture was then allowed to warm to 23° C. and held for an additional 3.5 hours to effect hydroboration. Subsequent oxidation was accomplished in the following manner: The mixture was cooled to 0° C. and water (24 ml) was slowly added, followed by dropwise addition of a 3N aqueous sodium hydroxide solution (32 ml), and then a 30% hydrogen peroxide solution (32 ml). After warming to 23° C., the mixture was maintained at this temperature overnight and subsequently warmed to 40° C. for 1 hour to complete the oxidation step. Aqueous workup was followed by flash column chromatography (SiO2) to give the desired product (1.68 g) as a water-white oil.

EMBODIMENT 205

6-exo-(2-Methylbenzyloxy)-1,5-dimethyl-8-oxabicyclo[3.2.1]octan-6-ol

A stirred solution of 1,5-dimethyl-8-oxabicyclo[3.2.1]octan-6-ol (0.2 g) in dry N,N-dimethylacetamide (3 ml) was treated at 23° C. with sodium hydride (92 mg of a 50% oil dispersion). The mixture was heated at 90° C. until hydrogen evolution ceased (1 hour) and then allowed to cool to room temperature. 2-Methylbenzyl chloride (198 mg) was added and the mixture was heated to 70° C. After reaction for 1.5 hours at 70° C. and 12 hours at 23° C., the mixture was partitioned between hexane and water. The hexane layer was washed with brine, dried over magnesium sulfate, and concentrated to a yellow oil (368 mg). This crude material was purified by column chromatography (SiO2, 25% ether-hexane) to provide the desired product (258 mg) as a water-white oil.

EMBODIMENT 206

6-exo-(2-Fluorobenzyloxy)-1,5-dimethyl-8-oxabicyclo[3.2.1]octane

A stirred solution of 1,5-dimethyl-8-oxabicyclo[3.2.1]octan-6-exo-ol (0.8 g) in dry dimethylacetamide (12 ml) was treated at 23° C. with sodium hydride (0.37 g of a 50% oil dispersion). The mixture was heated at 95° C. until hydrogen evolution ceased (0.5 hours) and then allowed to cool to ambient temperature. 2-Fluorobenzyl chloride (1.06 g) was then added over ca 2 minutes and the mixture was warmed to 80° C. After reaction at 80° C. for 0.5 hour and recooling to 23° C., the mixture was partitioned between hexane-water (5:1). The hexane layer was washed with brine, dried over magnesium sulfate, and concentrated to a yellow oil (1.6 g). This crude material was purified by column chromatography (SiO2; hexane; 25% ether-hexane) to produce the desired product (875 mg) as a water-white oil.

EMBODIMENT 207

1-Acetyl-2-(2-propen-2-yl)cyclopropanecarboxylic Acid, Ethyl Ester

Ethyl acetoacetate (125.8 g) in 400 ml of toluene was added dropwise to a suspension of sodium hydride (68.3 g of a 60% oil dispersion washed with pentane) in 1 L of toluene under an N2 blanket at −6° C. to 2° C. After 20 minutes, 1,4-dibromo-2-methyl-2-butene (220.6 g) in 300 ml of toluene was added dropwise at −2° C. to 0° C. The reaction mixture was allowed to warm to ambient temperature and after 22 hours, was diluted with water and extracted with ethyl acetate (thrice). The combined organic extracts were washed with water, brine, dried and concentrated in vacuuo. GLC of the crude material indicated 77% of the two desired isomers. The isomers were separated by flash chromatography using 7.5% ethyl acetate in hexane, giving ca 90% pure isomers.

In one instance the initial work-up from a second similar experiment was separated on a preparative HPLC (silica gel hexane-EtOAc gradient). A set of fractions was distilled to give the lower $R_f$ isomer as a colorless liquid, b.p. 50° C. at 0.08 mmHg.

A less polar set of fractions was distilled to give the higher $R_f$ isomer as a colorless liquid, b.p. 50° C. at 0.08 mm.

EMBODIMENT 208

3-Methyl-1-(1-oxoethyl)-3-cyclopentene-1-carboxylic Acid, Ethyl Ester

The product mixture of isomers from Embodiment 207 above was passed neat under nitrogen at about 40 drops per minute through a pyrolysis column packed with glass helicies (previously washed with ammonium hydroxide, acetone and hexane) and heated at 500° C. The pyrolysate was collected in heptane cooled by a dry ice bath. The heptane was removed in vacuuo and the residue was dissolved in diethyl ether, washed twice with 5% sodium hydroxide, brine, dried (Na2SO4), concentrated in vacuuo, and kugelrohr distilled at 80° C. (0.08 mm) to give a crude product. This crude pyrolysis product was separated twice on a silica gel preparative HPLC with ethyl acetate-hexane as eluent. The major component was distilled to give the desired product as a colorless liquid, b.p. 85° C. (1.3 mm).

EMBODIMENT 209

1-(1-Methyl-1-cyclopenten-4-yl)ethanone

A solution of potassium hydroxide (4.03 g) in water (20 ml) was added in one portion to a solution of 1.00 g the product of Embodiment 208 above in MeOH (5 ml). The reaction was warmed to reflux for 20 minutes, diluted with water and extracted with diethyl ether three times. The combined extracts were washed with brine, dried (Na2SO4) and concentrated in vacuuo. The crude material was vacuum distilled to about 90% purity and carried to the next step.

In another similar experiment the distillation gave the desired product, b.p. 80° C. (27 mm) as a colorless liquid.

EMBODIMENT 210 alpha,alpha,3-Trimethyl-3-cyclopentene-1-methanol

A solution of the crude product of Embodiment 209 above in 40 ml of tetrahydrofuran was added to 24 ml methylmagnesium bromide in diethyl ether at −50° C. to −10° C. under nitrogen. The reaction mixture was kept at −20° C., and after 2 hours was diluted with cold saturated ammonium chloride. The solution was extracted with diethyl ether three times, and the combined extracts were washed with brine, dried (MgSO4) and concentrated in vacuo. The residue was separated by flash silica gel chromatography using about 2.4 L of a 40/2/8 hexane/tetrahydrofuran/ethyl acetate mixture. A small portion of the fraction containing the desired product was distilled to give 0.26 g of the desired product as a colorless liquid, b.p. 50° C. (0.6 mm).

EMBODIMENT 211

1,3,3-Trimethyl-2-oxabicyclo[2.2.1]heptan-6-exo-ol

A solution of 0.26 g of the product of Embodiment 210 above in 4 ml of chloroform was added dropwise to refluxing 40% peracetic acid under a nitrogen blanket. After one-half hour, the solution was cooled, diluted with methylene chloride, washed with 25% potassium carbonate, saturated sodium chloride, dried (MgSO4) and concentrated in vacuo. The mixture was separated on a silica gel preparative HPLC using hexane-ethyl acetate as eluent to give 0.44 g of the desired product as a yellow liquid.

EMBODIMENT 212

1,3,3-Trimethyl-2-oxabicyclo[2.2.1]heptan-6-one

To a solution of 3.96 g of oxalyl chloride in 36 ml of methylene chloride was added a solution of 5.11 g of dimethyl sulfoxide in 12 ml of methylene chloride at −60° C. to −70° C. under nitrogen. After 10 minutes, 4.44 g of crude 1,3,3-trimethyl-2-oxabicyclo[2.2.1]heptan-6-exo-ol (Embodiment 211) in 12 ml methylene chloride was added dropwise at −60° C. After 15 minutes, 14.3 g of triethylamine was added at −70° C. to −50° C. The reaction was allowed to warm to −20° and diluted with water. THe CH2Cl2 phase was separated, and the aqueous phase was saturated with sodium chloride and extracted twice with methylene chloride. The combined organic phases were dried (MgSO4) and concentrated in vacuo. The residue was separated by silica gel flash chromatography using 2 L of 40/2/8 hexane/tetrahydrofuran/ethyl acetate and 2 L of 33/2/15 hexane/tetrahydrofuran/ethyl acetate mixture as eluents. One set of fractions gave 2.08 g of the desired product as a yellow liquid.

EMBODIMENT 213 endo-1,3,3-Trimethyl-2-oxabicyclo[2.2.1]heptan-6-ol

To a solution of 16 ml of lithium tri-sec-butylborohydride in tetrahydrofuran was added 2.05 g of the ketone of Embodiment 212 in 10 ml dry tetrahydrofuran at −70° C. to −62° C. under nitrogen. The reaction mixture was stirred for 1 hour at −70° C. and then 1 hour at ambient temperature. To the mixture was successively added 1.1 ml of water, 2.4 ml of ethanol, 13.3 ml of 10% sodium hydroxide and 5.8 ml of 30% hydrogen peroxide. After 1 hour, the reaction mixture was saturated with potassium carbonate and extracted with diethyl ether three times. The combined extracts were dried (MgSO4) and concentrated in vacuo to give 1.56 g of the desired product as a yellow liquid.

EMBODIMENT 214 endo-1,3,3-Trimethyl-6-(2-fluorobenzyloxy)-2-oxabicyclo[2.2.1]heptane

A solution of 0.50 g of the endo-alcohol of Embodiment 213 in 5 ml of dimethylformamide was added to a 60% oil dispersion of 0.17 g of sodium hydride (previously washed with pentane) in 2 ml of dimethylformamide at 10° C. under nitrogen. After 45 minutes, 0.73 g of 2-fluorobenzyl bromide in 2 ml of dimethylformamide was added, and after 13.5 hours, a trace of potassium iodide. After 15 hours, more, the reaction mixture was diluted with brine, dried (MgSO4) and concentrated in vacuo. The residue was purified by silica gel flash chromatography using 1 L of 90/4/6 hexane/tetrahydrofuran/ethyl acetate as eluent and vacuum distilled on a kugelrohr apparatus to give 0.41 g of the desired product as a colorless liquid, b.p. 85° C. at 0.05 mm.

EMBODIMENT 215 endo-1,3,3-Trimethyl-6-(2-methylbenzyloxy)-2-oxabicyclo[2.2.1]heptane

Following procedures similar to Embodiment 214 above, 0.50 g of the endo-alcohol of Embodiment 213 above was treated with 0.20 g of 2-methylbenzyl bromide to yield the desired product as a colorless liquid, b.p. 100° C. at 0.06 mm.

EMBODIMENT 216 endo-1,3,3-Trimethyl-6-benzyloxy-2-oxabicyclo[2.2.1]heptane

Following procedures similar to those of Embodiment 214 above, 0.31 g of the endo-alcohol of Embodiment 213 above was treated with 0.41 g of benzyl bromide to yield the desired product as a colorless liquid, b.p. 70° C. at 0.05 mm.

EMBODIMENT 217

(+)-2-exo-Hydroxy-1-methyl-4-isopropyl-7-oxabicyclo[2.2.1]heptane

The procedure of Embodiment 1 was repeated using (−)-terpinen-4-ol ($[\alpha]_D-28°$ (CHCl3)). The distilled product was recrystallized from hexane to give the subject material having m.p. 83°-85° C. and $[\alpha]_D+0.4°$ (CHCl3).

EMBODIMENT 218

(−)-2-exo-(2-Methylbenzyloxy)-1-methyl-4-isopropyl-7-oxabicyclo[2.2.1]heptane

To a stirred solution of 2.6 g of (+)-2-exo-hydroxy-1-methyl-4-isopropyl-7-oxabicyclo[2.2.1]heptane of Embodiment 217 above in 20 ml of N,N-dimethylacetamide was added 0.8 g of 50% sodium hydride (washed with hexane). After 1 hour at 60° C., the mixture was cooled to 25° C., treated with 2.3 g of 2-methylbenzyl chloride, and allowed to stir overnight at ambient temperature. After 0.5 hour at 50° C., the mixture was cooled, poured into water and extracted twice with hexane. The combined extracts were washed, dried, concentrated and Claisen-distilled to give 3.5 g of the subject compound, b.p. 114°-116° C. (0.1 mm); $[\alpha]_D-73°$ (CHCl3).

EMBODIMENT 219

(±)-2-exo-(2-Methylbenzyloxy)-1-methyl-4-isopropyl-7-oxabicyclo[2.2.1]heptane

A 12 l flask was charged under nitrogen with 264 g of 50% sodium hydride (previously washed with hexane) followed by 3 l of dry dimethylformamide. The resulting mixture was heated to 60° C. and a solution of 850 g of (±)-2-exo-hydroxy-1-methyl-4-isopropyl-7-oxabicyclo[2.2.1]heptane in 1.5 l of dimethylformamide was added over 3 hours while maintaining the reaction mixture at 60°–70° C. Then the reaction mixture was cooled to 20° C. and 730.6 g of 2-methylbenzyl chloride was added over 1½ hours while cooling the reaction mixture to 20°–25° C. The reaction mixture was stirred at room temperature for 16 hours. The resulting mixture was poured into 20 l of water, acidified with concentrated hydrochloric acid and extracted three times with 3.5 l of hexane. The combined extracts were back-washed with 3 l of water, dried (MgSO$_4$), filtered and evaporated to dryness to yield 1280 g of the desired product.

EMBODIMENT 220

(±)-2-exo-Benzyloxy-1-methyl-4-acetyl-7-oxabicyclo[2.2.1]heptane

To a stirred mixture of 15.1 g of the ether of Embodiment 166 above, 150 ml of ether and 150 ml of water were added 30 ml of 2% osmium tetroxide in t-butanol. After 15 minutes, 27.2 g of sodium metaperiodate was added and the reaction was continued at reflux for 18 hours. The ether layer was separated and the aqueous layer was extracted with ether. The combined ether extracts were washed, dried, concentrated, and Claisen-distilled to give 11.1 g of the desired product, b.p. 120° C. (0.1 mm).

EMBODIMENT 221

(±)-2-exo-Benzyloxy-1-methyl-4-carboxy-7-oxabicyclo[2.2.1]heptane

To a stirred solution of 8.4 g of the ether of Embodiment 220 above in 240 ml of dioxane held at 10°–15° C. was added a solution of 6.5 ml of bromine in 160 ml of water containing 42 g of potassium hydroxide. The mixture was stirred for 18 hours at 10°–25° C. and then poured into 300 ml of one-fourth saturated sodium bisulfite. This mixture was first extracted with 300 ml of ether and then acidified with 110 ml of 6N hydrochloric acid. The acidic product was extracted into three 250 ml portions of ether. The combined latter extracts were washed, dried and concentrated at 40° C. and <1 mm to give 8.8 g of crude product. Recrystallization from ether-pentene gave 6.5 g of the desired product, m.p. 93°–95° C.

EMBODIMENT 222

(±)-2-exo-Benzyloxy-1-methyl-4-carbamoyl-7-oxabicyclo[2.2.1]heptane

The product of Embodiment 221 above was converted to the acid chloride and the latter was treated with ammonia to give the desired product, m.p. 122°–123° C.

EMBODIMENT 223

(±)-2-exo-Benzyloxy-1-methyl-4-cyano-7-oxabicyclo[2.2.1]heptane

The ether of Embodiment 222 above was treated with acetic anhydride and pyridine to give the desired product, recovered as an oil.

EMBODIMENTS 224–229

Following procedures similar to those described for Embodiment 3, the ethers set forth in Table V below were prepared.

TABLE V

| Embodiment | R | b.p., °C. (mm) |
|---|---|---|
| 224 | 2-CH$_2$N(CH$_3$)$_2$ | 132–135 (0.1) |
| 225 | 4-Br | 140–143 (0.1) |
| 226 | 4-CN | 142–145 (0.1) |
| 227 | 2-OH | 137–138 (0.1) |
| 228 | 2-CH$_2$N$^+$(CH$_3$)$_3$I$^-$ | amorphous solid |
| 229 | 2-I | 141–144 (0.2) |

EMBODIMENT 230

(±)-2-exo-(Cyclohexylmethoxy-1-methyl-4-isopropyl-7-oxabicyclo[2.2.1]heptane

A 7.8 g sample of the product of Embodiment 3 above was dissolved in 40 ml of methanol containing 0.5 ml of acetic acid and treated with 1.5 g of 5% rhodium on alumina. This was shaken at 25° C. with hydrogen at an initial pressure of 50 psig. After 4 hours, the catalyst was removed by filtration through Celite and the filtrate was distilled to give 7.4 g of the desired product, b.p. 97°–101° C. (0.1 mm), 100% pure by GC/MS analysis.

Examples of Herbicidal Activity

In the following examples, the species of plants that were tested were:
Barnyardgrass (watergrass)—*Enchinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnsongrass—*Sorghum halepense*

EMBODIMENT A

The preemergence (soil) herbicidal activity of compounds of the invention was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyard grass and cress seeds contained one milligram of the test compound per tube, and contained 0.1 milligram of the test compound per each tube containing the seeds of the other plants. The dosages were approximately twenty and two pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |
| 7 | Plant badly damaged, but recovery expected to live |
| 6 | Moderate plant damage, but complete recovery expected |
| 5 | Intermediate damage (probably unacceptable damage for crop plants) |
| 3–4 | Observable damage |
| 1–2 | Plant slightly affected, possibly by the chemical, |

-continued

| Rating | Meaning |
| --- | --- |
|  | possibly due to biological variability |
| 0 | No visible effect |

The postemergence (foliar) herbicidal activity of Compounds of the Invention was evaluated by spraying 10-day-old large crabgrass plants, 13-day-old redroot pigweed plants, 6-day-old Johnsongrass plants, 9-day-old velvetleaf plants, 9-day-old yellow foxtail plants and 9-day-old sicklepod plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days and the effect of the test compound was then evaluated visually, the results being rated on the 0 to 9 scale described above.

Results of the preemergence and postemergence herbicidal activity tests conducted on the compounds of the invention are set forth in Table V below.

TABLE VI

| | Preemergence | | | | | | Postemergence | | | | | |
| --- | --- | --- | --- | --- | --- | --- | --- | --- | --- | --- | --- | --- |
| Embodiment | Barnyard Grass | Garden Cress | Downy Brome | Velvet Leaf | Yellow Foxtail | Sicklepod | Crab Grass | Pig Weed | Johnson-grass | Velvet Leaf | Yellow Foxtail | Sicklepod |
| 3 | 9 | 7 | 9 | 7 | 9 | 7 | 8 | 6 | 8 | 5 | 9 | 4 |
| 35 | 9 | 7 | 9 | 6 | 8 | 5 | 7 | 7 | 4 | 3 | 4 | 2 |
| 120 | 9 | 7 | 9 | 7 | 8 | 3 | 8 | 5 | 4 | 3 | 7 | 3 |
| 9 | 9 | 6 | 9 | 6 | 9 | 6 | 8 | 4 | 4 | 6 | 8 | 4 |
| 10 | 9 | 7 | 9 | 7 | 8 | 6 | 8 | 6 | 6 | 6 | 7 | 6 |
| 14 | 9 | 8 | 9 | 7 | 9 | 7 | 8 | 4 | 7 | 5 | 8 | 3 |
| 39 | 9 | 7 | 9 | 6 | 8 | 3 | 6 | 5 | 0 | 3 | 2 | 2 |
| 15 | 9 | 8 | 9 | 7 | 8 | 7 | 8 | 7 | 8 | 6 | 8 | 6 |
| 16 | 8 | 7 | 8 | 7 | 9 | 6 | 8 | 5 | 3 | 6 | 8 | 3 |
| 13 | 9 | 7 | 9 | 7 | 9 | 5 | 9 | 5 | 3 | 4 | 8 | 3 |
| 11 | 9 | 7 | 9 | 7 | 8 | 6 | 3 | 2 | 0 | 0 | 0 | 0 |
| 38 | 8 | 7 | 6 | 5 | 0 | 2 | 3 | 2 | 0 | 3 | 2 | 2 |
| 12 | 9 | 7 | 9 | 7 | 8 | 4 | 7 | 5 | 3 | 5 | 3 | 2 |
| 7 | 9 | 7 | 9 | 7 | 8 | 7 | 7 | 4 | 6 | 5 | 8 | 3 |
| 18 | 9 | 7 | 9 | 7 | 8 | 7 | 8 | 3 | 6 | 6 | 9 | 2 |
| 19 | 9 | 7 | 9 | 7 | 8 | 7 | 8 | 6 | 5 | 4 | 9 | 2 |
| 21 | 9 | 7 | 9 | 7 | 9 | 7 | 8 | 5 | 0 | 4 | 2 | 2 |
| 20 | 9 | 7 | 9 | 7 | 8 | 7 | 8 | 6 | 5 | 6 | 8 | 6 |
| 17 | 9 | 8 | 9 | 7 | 9 | 7 | 4 | 4 | 0 | 3 | 2 | 2 |
| 22 | 9 | 8 | 9 | 7 | 8 | 7 | 6 | 5 | 3 | 2 | 6 | 2 |
| 23 | 9 | 7 | 9 | 7 | 8 | 6 | 7 | 6 | 2 | 3 | 5 | 3 |
| 24 | 9 | 7 | 9 | 7 | 8 | 8 | 7 | 5 | 2 | 4 | 7 | 2 |
| 25 | 9 | 7 | 9 | 7 | 8 | 7 | 8 | 5 | 4 | 4 | 7 | 3 |
| 26 | 9 | 7 | 9 | 7 | 9 | 7 | 7 | 6 | 3 | 6 | 5 | 3 |
| 28 | 9 | 7 | 9 | 7 | 8 | 7 | 7 | 6 | 4 | 7 | 7 | 4 |
| 27 | 9 | 7 | 9 | 7 | 9 | 6 | 8 | 7 | 5 | 7 | 7 | 3 |
| 58 | 9 | 7 | 9 | 5 | 8 | 5 | 2 | 2 | 1 | 2 | 1 | 1 |
| 30 | 9 | 7 | 9 | 7 | 8 | 6 | 3 | 2 | 0 | 2 | 0 | 2 |
| 31 | 9 | 7 | 9 | 7 | 8 | 7 | 6 | 3 | 0 | 4 | 2 | 2 |
| 32 | 9 | 6 | 8 | 5 | 8 | 4 | 8 | 5 | 6 | 6 | 8 | 3 |
| 33 | 9 | 7 | 9 | 7 | 8 | 6 | 8 | 5 | 3 | 7 | 7 | 2 |
| 34 | 9 | 7 | 9 | 7 | 8 | 7 | 7 | 4 | 3 | 6 | 4 | 5 |
| 59 | 9 | 7 | 9 | 7 | 8 | 5 | 7 | 3 | 0 | 2 | 0 | 0 |
| 60 | 9 | 7 | 9 | 6 | 8 | 3 | 8 | 6 | 2 | 3 | 2 | 3 |
| 56 | 9 | 7 | 9 | 7 | 9 | 5 | 4 | 3 | 4 | 3 | 2 | 2 |
| 40 | 9 | 7 | 9 | 5 | 8 | 3 | 7 | 6 | 6 | 4 | 7 | 4 |
| 29 | 9 | 7 | 9 | 7 | 8 | 4 | 8 | 6 | 8 | 6 | 7 | 3 |
| 54 | 8 | 7 | 9 | 7 | 7 | 3 | 6 | 6 | 3 | 6 | 2 | 0 |
| 41 | 9 | 7 | 9 | 7 | 8 | 6 | 9 | 7 | 8 | 5 | 7 | 3 |
| 43 | 9 | 7 | 8 | 7 | 8 | 5 | 2 | 2 | 2 | 7 | 7 | 3 |
| 51 | 9 | 7 | 9 | 6 | 8 | 5 | 9 | 3 | 8 | 6 | 8 | 2 |
| 47 | 7 | 3 | 5 | 2 | 5 | 2 | 5 | 5 | 2 | 5 | 0 | 2 |
| 42 | 9 | 7 | 9 | 6 | 9 | 6 | 8 | 6 | 4 | 6 | 7 | 3 |
| 49 | 8 | 3 | 4 | 3 | 7 | 3 | 2 | 2 | 0 | 2 | 0 | 2 |
| 61 | 9 | 7 | 9 | 5 | 5 | 2 | 2 | 0 | 0 | 2 | 0 | 2 |
| 62 | 9 | 7 | 9 | 7 | 8 | 2 | 8 | 6 | 8 | 6 | 7 | 3 |

TABLE VI-continued
HERBICIDAL ACTIVITY

| | | | | | | | | | | | |
|---|---|---|---|---|---|---|---|---|---|---|---|
| 121 | 9 | 7 | 9 | 7 | 8 | 7 | 8 | 5 | 0 | 3 | 7 | 3 |
| 64 | 8 | 7 | 3 | 3 | 0 | 0 | 8 | 7 | 0 | 2 | — | 0 |
| 70 | 9 | 7 | 9 | 6 | 8 | 3 | 8 | 4 | 5 | 4 | 7 | 4 |
| 71 | 9 | 6 | 9 | 6 | 8 | 6 | 7 | 2 | 5 | 4 | 6 | 2 |
| 72 | 9 | 6 | 9 | 6 | 8 | 6 | 8 | 3 | 7 | 6 | 7 | 2 |
| 73 | 9 | 6 | 9 | 6 | 8 | 6 | 8 | 6 | 5 | 6 | 7 | 3 |
| 74 | 9 | 7 | 9 | 6 | 8 | 6 | 8 | 7 | 4 | 3 | 8 | 4 |
| 8 | 9 | 8 | 9 | 7 | 9 | 7 | 8 | 7 | 5 | 4 | 7 | 2 |
| 122 | 9 | 7 | 9 | 7 | 8 | 6 | 7 | 6 | 0 | 4 | 6 | 2 |
| 36 | 8 | 7 | 9 | 7 | 8 | 6 | 3 | 2 | 0 | 2 | 0 | 2 |
| 44 | 8 | 7 | 8 | 6 | 8 | 5 | 6 | 2 | 2 | 3 | 2 | 2 |
| 63 | 9 | 7 | 7 | 7 | 8 | 6 | 8 | 6 | 7 | 6 | 8 | 6 |
| 123 | 9 | 6 | 9 | 5 | 7 | 5 | 8 | 7 | 7 | 6 | — | 6 |
| 124 | 7 | 6 | 8 | 4 | 7 | 4 | 8 | 7 | 7 | 6 | — | 5 |

| | Preemergence (Soil) | | | | | | Postemergence (Foliar) | | | | | |
|---|---|---|---|---|---|---|---|---|---|---|---|---|
| Embodiment | Barnyard Grass | Garden Cress | Downy Brome | Velvet Leaf | Yellow Foxtail | Sicklepod | Crab Grass | Pig Weed | Johnson Grass | Velvet Leaf | Yellow Foxtail | Sicklepod |
| 90 | 9 | 7 | 9 | 6 | 8 | 6 | 8 | 3 | 3 | 3 | 7 | 5 |
| 91 | 9 | 6 | 9 | 6 | 8 | 5 | 8 | 4 | 3 | 5 | 5 | 5 |
| 92 | 9 | 7 | 9 | 6 | 8 | 6 | 8 | 6 | 3 | 6 | 7 | 4 |
| 93 | 8 | 6 | 9 | 6 | 7 | 3 | 8 | 7 | 5 | 7 | 7 | 7 |
| 94 | 9 | 7 | 9 | 5 | 8 | 6 | 6 | 4 | 0 | 5 | 3 | 3 |
| 101 | 9 | 7 | 9 | 7 | 8 | 7 | 8 | 5 | 6 | 4 | 7 | 7 |
| 107 | 9 | 7 | 6 | 6 | 8 | 5 | 7 | 3 | 0 | 3 | 0 | 0 |
| 79 | 9 | 5 | 9 | 3 | 8 | 0 | 9 | 4 | 5 | 6 | 8 | 7 |
| 89 | 9 | 7 | 9 | 5 | 8 | 6 | 6 | 5 | 0 | 2 | 5 | 3 |
| 96 | 8 | 0 | 9 | 0 | 6 | 0 | 8 | 6 | 6 | 7 | 8 | 3 |
| 97 | 9 | 7 | 9 | 2 | 8 | 3 | 8 | 7 | 6 | 6 | 7 | 6 |
| 98 | 9 | 7 | 9 | 0 | 8 | 3 | 8 | 7 | 3 | 6 | 7 | 3 |
| 99 | 9 | 7 | 9 | 4 | 8 | 4 | 8 | 7 | 0 | 4 | 3 | 6 |
| 84 | 9 | 6 | 9 | 5 | 8 | 3 | 9 | 7 | 7 | 6 | 7 | 3 |
| 100 | 9 | 6 | 9 | 5 | 8 | 3 | 8 | 6 | 5 | 4 | 7 | 2 |
| 104 | 8 | 6 | 6 | 4 | 8 | 2 | 8 | 7 | 7 | 6 | 7 | 5 |
| 102 | 9 | 7 | 8 | 5 | 8 | 5 | 9 | 7 | 7 | 6 | 8 | 7 |
| 103 | 9 | 7 | 9 | 2 | 8 | 3 | 8 | 7 | 7 | 6 | 8 | 7 |
| 105 | 8 | 6 | 5 | 2 | 4 | 2 | 9 | 7 | 8 | 6 | 8 | 7 |
| 108 | 7 | 2 | 3 | 0 | 4 | 0 | 7 | 7 | 4 | 4 | 8 | 5 |
| 109 | 9 | 7 | 9 | 5 | 8 | 5 | 8 | 6 | 6 | 3 | 8 | 6 |
| 95 | 5 | 0 | 4 | 0 | 3 | 0 | 8 | 4 | 2 | 6 | 8 | 7 |
| 112 | 9 | 6 | 9 | 5 | 9 | 6 | 5 | 5 | 3 | 0 | 2 | 2 |
| 111 | 8 | 3 | 7 | 2 | 8 | 3 | 8 | 5 | 4 | 3 | 5 | 7 |
| 113 | 9 | 7 | 9 | 3 | 8 | 4 | 0 | 0 | 0 | 0 | 0 | 0 |
| 115 | 9 | 7 | 8 | 6 | 8 | 4 | 7 | 4 | 0 | 3 | 3 | 2 |
| 114 | 9 | 7 | 9 | 6 | 8 | 4 | 8 | 5 | 5 | 6 | 8 | 4 |
| 166 | 9 | 7 | 9 | 6 | 8 | 6 | 9 | 4 | 5 | 4 | 7 | 5 |
| 124 | 9 | 6 | 7 | 5 | 7 | 0 | 7 | 3 | 3 | 5 | 7 | 4 |
| 125 | 8 | 6 | 8 | 5 | 5 | 2 | 8 | 4 | 6 | 6 | 7 | 3 |
| 126 | 0 | 0 | 0 | 0 | 0 | 0 | 7 | 3 | 3 | 4 | 7 | 0 |
| 127 | 6 | 0 | 3 | 0 | 0 | 0 | 7 | 3 | 5 | 5 | 7 | 2 |
| 128 | 6 | 5 | 4 | 3 | 4 | 2 | 7 | 4 | 3 | 6 | 7 | 3 |
| 129 | 7 | 2 | 0 | 0 | 0 | 0 | 3 | 0 | 2 | 2 | 3 | 0 |
| 130 | 9 | 6 | 8 | 6 | 8 | 5 | 7 | 4 | 6 | 5 | 7 | 4 |
| 131 | 9 | 6 | 7 | 5 | 6 | 5 | 8 | 3 | 7 | 5 | 8 | 3 |
| 132 | 9 | 6 | 9 | 6 | 8 | 3 | 9 | 6 | 7 | 6 | 7 | 4 |
| 133 | 8 | 5 | 5 | 5 | 5 | 2 | 7 | 4 | 2 | 3 | 2 | 3 |
| 134 | 6 | 8 | 5 | 0 | 5 | 0 | 8 | 5 | 6 | 4 | 7 | 2 |
| 135 | 9 | 7 | 9 | 6 | 8 | 6 | 8 | 7 | 6 | 6 | 8 | 6 |
| 136 | 8 | 7 | 7 | 6 | 6 | 4 | 8 | 6 | 3 | 3 | 5 | 5 |
| 137 | 0 | 0 | 0 | 0 | 0 | 0 | 7 | 3 | 3 | 2 | 3 | 2 |
| 139 | 9 | 7 | 8 | 6 | 8 | 2 | 9 | 7 | 6 | 6 | 7 | 3 |
| 140 | 9 | 9 | 8 | 5 | 7 | 2 | 8 | 3 | 3 | 3 | 7 | 4 |
| 141 | 3 | 2 | 0 | 0 | 0 | 2 | 3 | 3 | 2 | 2 | 0 | 2 |
| 138 | 8 | 7 | 9 | 6 | 8 | 6 | 7 | 4 | 3 | 6 | 7 | 2 |
| 143 | 9 | 7 | 9 | 6 | 8 | 6 | 8 | 3 | 6 | 5 | 7 | 2 |
| 159 | 9 | 7 | 9 | 6 | 8 | 4 | 2 | 3 | 1 | 2 | 0 | 2 |
| 164 | 9 | 7 | 9 | 6 | 8 | 5 | 8 | 3 | 7 | 6 | 7 | 2 |
| 165 | 9 | 7 | 9 | 6 | 8 | 5 | 9 | 3 | 7 | 6 | 7 | 2 |
| 144 | 9 | 7 | 9 | 6 | 8 | 0 | 7 | 3 | 2 | 5 | 7 | 2 |
| 160 | 2 | 7 | 0 | 0 | 0 | 0 | 0 | 0 | 0 | 0 | 0 | 0 |
| 163 | 5 | 0 | 0 | 0 | 0 | 0 | 4 | 3 | 2 | 3 | 0 | 2 |
| 145 | 9 | 7 | 4 | 6 | 6 | 3 | 1 | 3 | 0 | 2 | 1 | 2 |
| 146 | 9 | 7 | 6 | 4 | 6 | 3 | 3 | 4 | 0 | 3 | 0 | 3 |
| 147 | 9 | 7 | 0 | 0 | 0 | 0 | 0 | 2 | 0 | 0 | 0 | 0 |
| 161 | 3 | 3 | 0 | 0 | 0 | 0 | 1 | 2 | 1 | 0 | 0 | 0 |
| 175 | 9 | 3 | 7 | 0 | 6 | 0 | 3 | 4 | 0 | 2 | 0 | 0 |
| 174 | 5 | 3 | 0 | 2 | 0 | 0 | 0 | 3 | 0 | 0 | 0 | 0 |
| 192 | 9 | 7 | 8 | 4 | 8 | 4 | 3 | 0 | 0 | 0 | 0 | 0 |
| 178 | 9 | 7 | 6 | 2 | 6 | 4 | 2 | 2 | 0 | 2 | 0 | 2 |
| 179 | 8 | 7 | 0 | 0 | 0 | 0 | 1 | 2 | 0 | 0 | 0 | 0 |
| 170a | 7 | 3 | 0 | 2 | 0 | 2 | 2 | 6 | 0 | 0 | 0 | 0 |

TABLE VI-continued

HERBICIDAL ACTIVITY

| | | | | | | | | | | | | |
|---|---|---|---|---|---|---|---|---|---|---|---|---|
| 170d | 8 | 3 | 7 | 2 | 4 | 4 | 3 | 5 | 1 | 2 | 2 | 3 |
| 171a | 9 | 7 | 8 | 4 | 7 | 0 | 6 | 4 | 1 | 3 | 1 | 2 |
| 171b | 7 | 4 | 5 | 0 | 0 | 0 | 2 | 3 | 0 | 2 | 0 | 2 |
| 148 | 9 | 8 | 4 | 0 | 6 | 0 | 4 | 0 | 0 | 0 | 0 | 0 |
| 149 | 9 | 6 | 0 | 0 | 0 | 0 | 0 | 0 | 4 | 0 | 0 | 0 |
| 150 | 0 | 3 | 0 | 3 | 0 | 2 | 2 | 3 | 0 | 2 | 0 | 0 |
| 151 | 8 | 6 | 7 | 2 | 3 | 2 | 4 | 3 | 1 | 3 | 1 | 3 |
| 152 | 7 | 2 | 3 | 2 | 3 | 0 | 3 | 3 | 2 | 3 | 1 | 2 |
| 153 | 7 | 5 | 0 | 0 | 0 | 0 | 0 | 3 | 0 | 2 | 0 | 0 |
| 154 | 9 | 6 | 6 | 5 | 7 | 2 | 7 | 4 | 3 | 3 | 6 | 2 |
| 185 | 9 | 7 | 9 | 2 | 7 | 4 | 3 | 5 | 0 | 0 | 0 | 0 |
| 188 | 9 | 3 | 4 | 0 | 3 | 0 | 0 | 0 | 0 | 0 | 0 | 0 |
| 162 | 9 | 6 | 8 | 2 | 8 | 2 | 4 | 3 | 3 | 5 | 1 | 2 |
| 195 | 7 | 3 | 3 | 3 | 0 | 5 | 2 | 5 | 1 | 3 | 0 | 2 |
| 155 | 8 | 5 | 2 | 3 | 1 | 2 | 2 | 3 | 2 | 3 | 1 | 2 |
| 156 | 7 | 6 | 2 | 3 | 2 | 2 | 2 | 8 | 0 | 3 | 0 | 2 |
| 142 | 7 | 5 | 5 | 3 | 0 | 3 | 3 | 3 | 0 | 3 | 0 | 3 |
| 206 | 9 | 7 | 9 | 3 | 9 | — | 7 | 5 | 2 | 2 | 2 | 2 |
| 205 | 9 | 7 | 8 | 6 | 8 | 4 | 7 | 5 | 2 | 4 | 6 | 4 |
| 215 | 9 | 7 | 9 | 7 | 8 | 7 | 7 | 5 | 3 | 3 | 0 | 0 |
| 216 | 9 | 7 | 9 | 7 | 8 | 7 | 7 | 6 | 0 | 6 | 0 | 2 |
| 217 | 9 | 7 | 9 | 7 | 7 | 7 | 8 | 3 | 4 | 4 | 0 | 0 |

— indicates "no test".

We claim:

1. A compound of the formula Ig

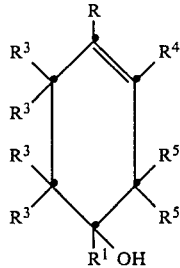

wherein

R is a hydrogen atom; or a straight-chain alkyl group containing from 1 to 6 carbon atoms;

$R^1$ is a hydrogen atom; an alkyl group containing from 1 to 6 carbon atoms; an alkyl group containing from 1 to 6 carbon atoms substituted by 1 to 3 halogen atoms, each having an atomic number of from 9 to 35, inclusive, a hydroxy group, a cyano group or an alkoxy group containing from 1 to 4 carbon atoms, a $C_{1-6}$ alkylthio group, a $C_{6-10}$ arylthio group, a $C_{7-11}$ aralkylthio group, an azido group, a $C_{1-6}$ alkoxycarbonyl group, a hydroxycarbonyl group, a phosphoryl group, a phosphoryloxy group, a carbamoyl group or a thiocarbamoyl group substituted by hydrogen or 1 or 2 alkyl groups containing from 1 to 6 carbon atoms; an aryl or aralkyl group, each containing from 6 to 10 carbon atoms, and 1 or 2 carbons in the alkyl portion; an aryl or aralkyl group containing from 6 to 10 carbon atoms, and 1 to 2 carbons in the alkyl portion, ring-substituted by one or more substituents independently selected from a halogen atom, each having an atomic number of from 9 to 35, inclusive, an alkyl or alkoxy group containing from 1 to 2 carbon atoms, or an alkyl or alkoxy group containing from 1 to 2 carbon atoms substituted by one or more halogen atoms, each having an atomic number of from 9 or 17; $R^1$ is a group —$CO_2R^6$ or —$CON(R^6)_2$ in which $R^6$ is a hydrogen atom, or an alkyl group containing from 1 to 6 carbon atoms;

each $R^3$ is independently selected from a hydrogen atom; a chlorine atom; a bromine atom; an alkyl group containing from 1 to 4 carbon atoms; an alkyl group containing from 1 to 4 carbon atoms substituted by 1 to 3 halogen atoms, each having an atomic number of from 9 to 35, inclusive; or two of $R^3$ when located on adjacent carbon atoms together form an epoxide ring or a carbon-carbon bond;

$R^4$ is a hydrogen atom; an alkyl group containing from 1 to 4 carbon atoms; or an alkyl group containing from 1 to 4 carbon atoms substituted by 1 to 3 halogen atoms having an atomic number of from 9 to 35, inclusive;

each $R^5$ is independently selected from a hydrogen atom; an alkyl group containing from 1 to 4 carbon atoms; an alkyl group containing 1 to 4 carbon atoms substituted by 1 to 3 halogen atoms having an atomic number of from 9 to 35, inclusive; or a hydroxy group;

and stereoisomeric forms or mixtures thereof, with the proviso that R and $R^1$ are not both hydrogen atoms and when R is methyl $R^3$, $R^4$ and $R^5$ all are hydrogen atoms, then $R^1$ is other than isopropyl.

2. A compound according to claim 1 wherein R and $R^1$ each independently is a hydrogen atom or an alkyl group containing from 1 to 3 carbon atoms.

3. A compound according to claim 1 wherein each $R^3$ is a hydrogen atom or an alkyl group containing 1 or 2 carbon atoms.

4. A compound according to claim 1 wherein $R^4$ is a hydrogen atom.

5. A compound according to claim 1 wherein each $R^5$ is a hydrogen atom or an alkyl group containing 1 or 2 carbon atoms.

6. A compound according to claim 1 wherein each $R^3$, $R^4$ and $R^5$ is a hydrogen atom.

7. A compound according to claim 6 wherein R is a methyl or ethyl group and $R^1$ is a methyl or ethyl group.

8. A compound according to claim 1 wherein R and $R^1$ each is an alkyl group containing from 1 to 3 carbon atoms or $R^1$ is an alkyl group containing 1 to 3 carbon atoms substituted by halogen.

9. A compound according to claim 8 of formula Id wherein R and $R^1$ each is an ethyl group or R is a methyl group and $R^1$ is 1-chloro-1-methylethyl group and $R^3$, $R^4$ and $R^5$ each is a hydrogen atom.

10. A compound according to claim 1 wherein R is a methyl group; $R^1$ is a 1-cyano-1-methylethyl group; and $R^3$, $R^4$ and $R^5$ is a hydrogen atom.

* * * * *